US010820885B2

(12) United States Patent
Cohen et al.

(10) Patent No.: US 10,820,885 B2
(45) Date of Patent: Nov. 3, 2020

(54) APPARATUS AND METHODS FOR DETECTION OF A REMOVABLE CAP ON AN ULTRASOUND PROBE

(71) Applicant: C. R. Bard, Inc., Murray Hill, NJ (US)

(72) Inventors: Benjamin A. Cohen, Tempe, AZ (US); Jeremy B. Cox, Salt Lake City, UT (US); Jeanette E. Southard, Park City, UT (US); Shayne Messerly, Kaysville, UT (US); Jay A. Muse, Salt Lake City, UT (US); Kevin W. Stinger, Kaysville, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 1351 days.

(21) Appl. No.: 13/918,707

(22) Filed: Jun. 14, 2013

(65) Prior Publication Data
US 2013/0338503 A1 Dec. 19, 2013

Related U.S. Application Data

(60) Provisional application No. 61/660,201, filed on Jun. 15, 2012.

(51) Int. Cl.
A61B 8/00 (2006.01)
A61B 8/08 (2006.01)

(52) U.S. Cl.
CPC ............ A61B 8/4411 (2013.01); A61B 8/429 (2013.01); A61B 8/4281 (2013.01); A61B 8/5292 (2013.01); A61B 8/585 (2013.01); A61B 8/0841 (2013.01); A61B 8/4438 (2013.01)

(58) Field of Classification Search
CPC ... A61B 8/4411; A61B 8/4281; A61B 8/5292; A61B 8/585; A61B 8/4438
See application file for complete search history.

(56) References Cited

U.S. PATENT DOCUMENTS 3,133,244 A 5/1964 Wojtulewicz
3,297,020 A 1/1967 Mathiesen
(Continued)

FOREIGN PATENT DOCUMENTS

AU 642647 11/1990
AU 1860597 B2 6/1999
(Continued)

OTHER PUBLICATIONS

Egelhof, Petra, Effects of Somatostatin on Portal Blood Flow and Portal Vein Pressure in Patients with Portal Hypertension due to Liver Cirrhosis Invasive Monitoring during TIPSS Procedures, Dissertation submitted to: Technical University of Munich, Faculty of Medicine, May 13, 2002; Date of examination: Feb. 26, 2003.
(Continued)

Primary Examiner — Joseph M Santos Rodriguez
(74) Attorney, Agent, or Firm — Rutan & Tucker LLP

(57) ABSTRACT

An ultrasound imaging device including the ability to determine when a component, such as a removable probe cap, is attached to a portion of an ultrasound probe. Such a cap is employed in one embodiment to act as a spacer component to provide a standoff for the probe head. Detection of probe cap attachment to the ultrasound probe enables the resultant ultrasound image to be adjusted automatically by the ultrasound imaging system. In one embodiment, an ultrasound imaging system comprises an ultrasound probe, a cap or other component that is attachable to the probe, and a component attachment detection system for detecting attachment of the component to the probe. Once the cap is detected, an aspect of an ultrasound image produced by the imaging system is modified, such as cropping the image to remove undesired portions of the cap, such as the spacer component.

20 Claims, 18 Drawing Sheets

(56) References Cited

U.S. PATENT DOCUMENTS

| | | |
|---|---|---|
| 3,625,200 A | 12/1971 | Muller |
| 3,674,014 A | 7/1972 | Tillander et al. |
| 3,817,241 A | 6/1974 | Grausz |
| 3,847,157 A | 11/1974 | Caillouette et al. |
| 3,868,565 A | 2/1975 | Kuipers |
| 3,902,501 A | 9/1975 | Citron et al. |
| 3,995,623 A | 12/1976 | Blake et al. |
| 4,003,369 A | 1/1977 | Heilman et al. |
| 4,063,561 A | 12/1977 | McKenna |
| 4,072,146 A | 2/1978 | Howes |
| 4,114,601 A | 9/1978 | Abels |
| 4,149,535 A | 4/1979 | Volder et al. |
| 4,173,228 A | 11/1979 | Steenwyk et al. |
| 4,175,566 A | 11/1979 | Millar |
| 4,181,120 A | 1/1980 | Kunii et al. |
| 4,224,949 A | 9/1980 | Scott et al. |
| 4,244,362 A | 1/1981 | Anderson |
| 4,246,792 A | 1/1981 | Matzuk |
| 4,289,139 A | 9/1981 | Enjoji et al. |
| 4,317,078 A | 2/1982 | Weed et al. |
| 4,327,722 A | 5/1982 | Groshong et al. |
| 4,362,166 A | 12/1982 | Furler et al. |
| 4,365,639 A | 12/1982 | Goldreyer |
| 4,380,237 A | 4/1983 | Newbower |
| 4,402,324 A | 9/1983 | Lindgren et al. |
| 4,407,294 A | 10/1983 | Vilkomerson |
| 4,429,693 A | 2/1984 | Blake et al. |
| 4,431,005 A | 2/1984 | McCormick |
| 4,431,214 A | 2/1984 | Buffington |
| 4,445,501 A | 5/1984 | Bresler |
| 4,459,854 A | 7/1984 | Richardson et al. |
| 4,469,106 A | 9/1984 | Harui |
| 4,483,343 A | 11/1984 | Beyer et al. |
| 4,491,137 A | 1/1985 | Jingu |
| 4,565,201 A | 1/1986 | Lass |
| 4,572,198 A | 2/1986 | Codrington |
| 4,577,634 A | 3/1986 | Gessman |
| 4,582,067 A | 4/1986 | Silverstein et al. |
| 4,588,394 A | 5/1986 | Schulte et al. |
| 4,593,687 A | 6/1986 | Gray |
| 4,593,699 A | 6/1986 | Poncy et al. |
| 4,595,012 A | 6/1986 | Webler et al. |
| 4,601,706 A | 7/1986 | Aillon |
| 4,608,989 A | 9/1986 | Drue |
| 4,608,992 A | 9/1986 | Hakim et al. |
| 4,619,247 A | 10/1986 | Inoue et al. |
| 4,622,644 A | 11/1986 | Hansen |
| 4,644,960 A | 2/1987 | Johans |
| 4,652,820 A | 3/1987 | Maresca |
| 4,665,925 A | 5/1987 | Millar |
| 4,667,230 A | 5/1987 | Arakawa et al. |
| 4,674,518 A | 6/1987 | Salo |
| 4,676,249 A | 6/1987 | Arenas et al. |
| 4,681,106 A | 7/1987 | Kensey et al. |
| 4,681,117 A | 7/1987 | Brodman et al. |
| 4,688,578 A | 8/1987 | Takano et al. |
| 4,692,148 A | 9/1987 | Kantrowitz et al. |
| 4,697,595 A | 10/1987 | Breyer et al. |
| 4,700,997 A | 10/1987 | Strand |
| 4,706,681 A | 11/1987 | Breyer et al. |
| 4,710,708 A | 12/1987 | Rorden et al. |
| 4,733,669 A | 3/1988 | Segal |
| 4,737,794 A | 4/1988 | Jones |
| 4,741,356 A | 5/1988 | Letzo et al. |
| 4,742,356 A | 5/1988 | Kuipers |
| 4,753,247 A | 6/1988 | Kirsner et al. |
| 4,770,185 A | 9/1988 | Silverstein et al. |
| 4,771,788 A | 9/1988 | Millar |
| 4,781,685 A | 11/1988 | Lehmann et al. |
| 4,784,646 A | 11/1988 | Feingold |
| 4,787,070 A | 11/1988 | Suzuki et al. |
| 4,787,396 A | 11/1988 | Pidorenko |
| 4,793,361 A | 12/1988 | DuFault |
| 4,794,930 A | 1/1989 | Machida et al. |
| 4,796,632 A | 1/1989 | Boyd et al. |
| 4,798,588 A | 1/1989 | Aillon |
| 4,798,598 A | 1/1989 | Bonello et al. |
| 4,809,681 A | 3/1989 | Kantrowitz et al. |
| 4,809,713 A | 3/1989 | Grayzel |
| 4,813,729 A | 3/1989 | Speckhart |
| 4,821,731 A | 4/1989 | Martinelli et al. |
| 4,836,214 A | 6/1989 | Sramek |
| 4,840,622 A | 6/1989 | Hardy |
| 4,849,692 A | 7/1989 | Blood |
| 4,850,358 A | 7/1989 | Millar |
| 4,852,580 A | 8/1989 | Wood |
| 4,856,317 A | 8/1989 | Pidorenko et al. |
| 4,856,529 A | 8/1989 | Segal |
| 4,860,757 A | 8/1989 | Lynch et al. |
| 4,867,169 A | 9/1989 | Machida et al. |
| 4,869,263 A | 9/1989 | Segal et al. |
| 4,869,718 A | 9/1989 | Brader |
| 4,887,606 A | 12/1989 | Yock et al. |
| 4,887,615 A | 12/1989 | Taylor |
| 4,889,128 A | 12/1989 | Millar |
| 4,899,756 A | 2/1990 | Sonek |
| 4,901,725 A | 2/1990 | Nappholz et al. |
| 4,905,698 A | 3/1990 | Strohl, Jr. et al. |
| 4,911,173 A | 3/1990 | Terwilliger |
| 4,911,174 A | 3/1990 | Pederson et al. |
| 4,924,870 A | 5/1990 | Wlodarczyk et al. |
| 4,943,770 A | 7/1990 | Ashley-Rollman et al. |
| 4,945,305 A | 7/1990 | Blood |
| 4,947,852 A | 8/1990 | Nassi et al. |
| 4,957,111 A | 9/1990 | Millar |
| 4,961,433 A | 10/1990 | Christian |
| 4,966,148 A | 10/1990 | Millar |
| 4,967,753 A | 11/1990 | Haase et al. |
| 4,977,886 A | 12/1990 | Takehana et al. |
| 4,989,608 A | 2/1991 | Ratner |
| 4,995,396 A | 2/1991 | Inaba et al. |
| 4,998,916 A | 3/1991 | Hammerslag et al. |
| 5,005,592 A | 4/1991 | Cartmell |
| 5,016,173 A | 5/1991 | Kenet et al. |
| 5,025,799 A | 6/1991 | Wilson |
| 5,029,585 A | 7/1991 | Lieber et al. |
| 5,040,548 A | 8/1991 | Yock |
| 5,042,486 A | 8/1991 | Pfeiler et al. |
| 5,045,071 A | 9/1991 | McCormick et al. |
| 5,046,497 A | 9/1991 | Millar |
| 5,050,607 A | 9/1991 | Bradley et al. |
| 5,057,095 A | 10/1991 | Fabian |
| 5,058,595 A | 10/1991 | Kern |
| 5,067,489 A | 11/1991 | Lind |
| 5,076,278 A | 12/1991 | Vilkomerson et al. |
| 5,076,279 A | 12/1991 | Arenson et al. |
| 5,078,140 A | 1/1992 | Kwoh |
| 5,078,148 A | 1/1992 | Nassi et al. |
| 5,078,149 A | 1/1992 | Katsumata et al. |
| 5,078,678 A | 1/1992 | Katims |
| 5,078,714 A | 1/1992 | Katims |
| 5,084,022 A | 1/1992 | Claude |
| 5,092,341 A | 3/1992 | Kelen |
| 5,099,845 A | 3/1992 | Besz et al. |
| 5,099,850 A | 3/1992 | Matsui et al. |
| 5,100,387 A | 3/1992 | Ng |
| 5,105,829 A | 4/1992 | Fabian et al. |
| 5,109,862 A | 5/1992 | Kelen et al. |
| 5,114,401 A | 5/1992 | Stuart et al. |
| 5,121,750 A | 6/1992 | Katims |
| D327,740 S | 7/1992 | Arioka et al. |
| 5,134,370 A | 7/1992 | Jefferts et al. |
| 5,144,955 A | 9/1992 | O'Hara |
| 5,158,086 A | 10/1992 | Brown et al. |
| 5,160,342 A | 11/1992 | Reger et al. |
| 5,161,536 A | 11/1992 | Vilkomerson et al. |
| 5,174,295 A | 12/1992 | Christian et al. |
| 5,184,601 A | 2/1993 | Putman |
| 5,190,045 A | 3/1993 | Frazin |
| 5,202,985 A | 4/1993 | Goyal |
| 5,211,165 A | 5/1993 | Dumoulin et al. |
| 5,211,636 A | 5/1993 | Mische |
| 5,212,988 A | 5/1993 | White et al. |
| 5,214,615 A | 5/1993 | Bauer et al. |

(56) References Cited

U.S. PATENT DOCUMENTS

| | | |
|---|---|---|
| 5,217,026 A | 6/1993 | Stoy et al. |
| 5,220,924 A | 6/1993 | Frazin |
| 5,235,987 A | 8/1993 | Wolfe |
| 5,239,464 A | 8/1993 | Blair et al. |
| 5,240,004 A | 8/1993 | Walinsky et al. |
| 5,243,995 A | 9/1993 | Maier |
| 5,246,007 A | 9/1993 | Frisbie et al. |
| 5,247,171 A | 9/1993 | Wlodarczyk et al. |
| 5,251,635 A | 10/1993 | Dumoulin et al. |
| 5,255,680 A | 10/1993 | Darrow et al. |
| 5,257,636 A | 11/1993 | White |
| 5,257,979 A | 11/1993 | Jagpal |
| 5,259,386 A | 11/1993 | Sharkawy |
| 5,261,409 A | 11/1993 | Dardel |
| 5,265,610 A | 11/1993 | Darrow et al. |
| 5,265,614 A | 11/1993 | Hayakawa et al. |
| 5,267,569 A | 12/1993 | Lienhard |
| 5,270,810 A | 12/1993 | Nishimura |
| 5,271,404 A | 12/1993 | Corl et al. |
| 5,273,025 A | 12/1993 | Sakiyama et al. |
| 5,273,042 A | 12/1993 | Lynch et al. |
| 5,274,551 A | 12/1993 | Corby, Jr. |
| 5,275,053 A | 1/1994 | Wlodarczyk et al. |
| 5,279,129 A | 1/1994 | Ito |
| 5,279,607 A | 1/1994 | Schentag et al. |
| 5,280,786 A | 1/1994 | Wlodarczyk et al. |
| 5,287,331 A | 2/1994 | Schindel et al. |
| 5,289,373 A | 2/1994 | Zarge et al. |
| 5,292,342 A | 3/1994 | Nelson et al. |
| 5,295,485 A | 3/1994 | Shinomura et al. |
| 5,307,072 A | 4/1994 | Jones, Jr. |
| 5,311,871 A | 5/1994 | Yock |
| 5,313,949 A | 5/1994 | Yock |
| 5,318,025 A | 6/1994 | Dumoulin et al. |
| 5,325,860 A | 7/1994 | Seward et al. |
| 5,325,873 A | 7/1994 | Hirschi et al. |
| 5,330,496 A | 7/1994 | Alferness |
| 5,331,966 A | 7/1994 | Bennett et al. |
| 5,333,614 A | 8/1994 | Feiring |
| 5,337,678 A | 8/1994 | Grout et al. |
| 5,341,807 A | 8/1994 | Nardella |
| 5,343,865 A | 9/1994 | Gardineer et al. |
| 5,345,940 A | 9/1994 | Seward et al. |
| 5,348,020 A | 9/1994 | Hutson |
| 5,350,352 A | 9/1994 | Buchholtz et al. |
| 5,357,961 A | 10/1994 | Fields et al. |
| 5,369,624 A | 11/1994 | Fukukita et al. |
| 5,375,596 A | 12/1994 | Twiss et al. |
| 5,376,083 A | 12/1994 | Mische |
| 5,377,678 A | 1/1995 | Dumoulin et al. |
| 5,385,053 A | 1/1995 | Wlodarczyk et al. |
| 5,390,675 A | 2/1995 | Sheehan et al. |
| 5,391,199 A | 2/1995 | Ben-Haim |
| 5,394,876 A | 3/1995 | Ma |
| 5,394,877 A | 3/1995 | Orr et al. |
| 5,395,366 A | 3/1995 | D'Andrea et al. |
| 5,398,683 A | 3/1995 | Edwards et al. |
| 5,398,691 A | 3/1995 | Martin et al. |
| 5,405,366 A | 4/1995 | Fox et al. |
| 5,411,485 A | 5/1995 | Tennican et al. |
| 5,413,107 A | 5/1995 | Oakley et al. |
| 5,422,478 A | 6/1995 | Wlodarczyk et al. |
| 5,425,367 A | 6/1995 | Shapiro et al. |
| 5,425,370 A | 6/1995 | Vilkomerson |
| 5,425,382 A | 6/1995 | Golden et al. |
| 5,427,114 A | 6/1995 | Colliver et al. |
| 5,429,132 A | 7/1995 | Guy et al. |
| 5,429,617 A | 7/1995 | Hammersmark et al. |
| 5,431,641 A | 7/1995 | Grozinger et al. |
| 5,433,729 A | 7/1995 | Adams et al. |
| 5,437,276 A | 8/1995 | Takada et al. |
| 5,437,277 A | 8/1995 | Dumoulin et al. |
| 5,438,873 A | 8/1995 | Wlodarczyk et al. |
| 5,443,066 A | 8/1995 | Dumoulin et al. |
| 5,443,489 A | 8/1995 | Ben-Haim |
| 5,445,150 A | 8/1995 | Dumoulin et al. |
| 5,450,846 A | 9/1995 | Goldreyer |
| 5,453,575 A | 9/1995 | O'Donnell et al. |
| 5,456,256 A | 10/1995 | Schneider |
| 5,456,718 A | 10/1995 | Szymaitis |
| 5,464,016 A | 11/1995 | Nicholas et al. |
| 5,469,851 A | 11/1995 | Lipschutz |
| 5,474,065 A | 12/1995 | Meathrel et al. |
| 5,476,090 A | 12/1995 | Kishi |
| 5,480,422 A | 1/1996 | Ben-Haim |
| 5,487,729 A | 1/1996 | Avellanet et al. |
| 5,490,522 A | 2/1996 | Dardel |
| 5,492,538 A | 2/1996 | Johlin, Jr. |
| 5,494,038 A | 2/1996 | Wang et al. |
| 5,500,012 A | 3/1996 | Brucker et al. |
| 5,505,205 A | 4/1996 | Solomon et al. |
| 5,509,822 A | 4/1996 | Negus et al. |
| 5,513,637 A | 5/1996 | Twiss et al. |
| 5,515,853 A | 5/1996 | Smith et al. |
| 5,522,878 A | 6/1996 | Montecalvo et al. |
| 5,526,812 A | 6/1996 | Dumoulin et al. |
| 5,531,664 A | 7/1996 | Adachi et al. |
| 5,540,033 A | 7/1996 | Fox et al. |
| 5,540,230 A | 7/1996 | Vilkomerson |
| 5,540,681 A | 7/1996 | Strul et al. |
| 5,542,938 A | 8/1996 | Avellanet et al. |
| 5,546,949 A | 8/1996 | Frazin et al. |
| 5,546,951 A | 8/1996 | Ben-Haim |
| 5,558,091 A | 9/1996 | Acker et al. |
| 5,568,809 A | 10/1996 | Ben-haim |
| 5,569,183 A | 10/1996 | Kieturakis |
| D375,450 S | 11/1996 | Bidwell et al. |
| 5,570,671 A | 11/1996 | Hickey |
| 5,575,291 A | 11/1996 | Hayakawa et al. |
| 5,583,286 A | 12/1996 | Matsuyama |
| 5,588,442 A | 12/1996 | Scovil et al. |
| 5,592,939 A | 1/1997 | Martinelli |
| 5,598,846 A | 2/1997 | Peszynski |
| 5,599,299 A | 2/1997 | Weaver et al. |
| 5,600,330 A | 2/1997 | Blood |
| 5,610,967 A | 3/1997 | Moorman et al. |
| 5,615,678 A | 4/1997 | Kirkham et al. |
| 5,617,864 A | 4/1997 | Stouffer et al. |
| 5,617,866 A | 4/1997 | Marian, Jr. |
| 5,622,169 A | 4/1997 | Golden et al. |
| 5,622,170 A | 4/1997 | Schulz |
| 5,622,184 A | 4/1997 | Ashby et al. |
| 5,623,931 A | 4/1997 | Wung et al. |
| 5,624,430 A | 4/1997 | Eton et al. |
| 5,626,554 A | 5/1997 | Ryaby et al. |
| 5,626,870 A | 5/1997 | Monshipouri et al. |
| 5,630,419 A | 5/1997 | Ranalletta |
| 5,640,960 A | 6/1997 | Jones et al. |
| 5,644,612 A | 7/1997 | Moorman et al. |
| 5,645,065 A | 7/1997 | Shapiro et al. |
| 5,651,047 A | 7/1997 | Moorman et al. |
| 5,654,864 A | 8/1997 | Ritter et al. |
| D383,968 S | 9/1997 | Bidwell et al. |
| 5,662,115 A | 9/1997 | Torp et al. |
| 5,665,477 A | 9/1997 | Meathrel et al. |
| 5,666,473 A | 9/1997 | Wallace |
| 5,666,958 A | 9/1997 | Rothenberg et al. |
| 5,668,888 A | 9/1997 | Doi et al. |
| 5,669,383 A | 9/1997 | Johnson |
| 5,669,388 A | 9/1997 | Vilkomerson |
| 5,676,159 A | 10/1997 | Navis |
| 5,676,673 A | 10/1997 | Ferre et al. |
| 5,691,898 A | 11/1997 | Rosenberg et al. |
| 5,694,945 A | 12/1997 | Ben-Haim |
| 5,695,479 A | 12/1997 | Jagpal |
| 5,697,377 A | 12/1997 | Wittkampf |
| 5,699,801 A | 12/1997 | Atalar et al. |
| 5,700,889 A | 12/1997 | Blair |
| 5,713,362 A | 2/1998 | Vilkomerson |
| 5,713,363 A | 2/1998 | Seward et al. |
| 5,713,946 A | 2/1998 | Ben-Haim |
| 5,715,817 A | 2/1998 | Stevens-Wright et al. |
| 5,716,389 A | 2/1998 | Walinsky et al. |
| 5,718,241 A | 2/1998 | Ben-Haim et al. |

(56) References Cited

U.S. PATENT DOCUMENTS

| | | |
|---|---|---|
| D391,838 S | 3/1998 | Bidwell et al. |
| 5,722,412 A | 3/1998 | Pflugrath et al. |
| 5,727,550 A | 3/1998 | Montecalvo |
| 5,727,552 A | 3/1998 | Ryan |
| 5,727,553 A | 3/1998 | Saad |
| 5,729,055 A | 3/1998 | Manning |
| 5,729,129 A | 3/1998 | Acker |
| 5,729,584 A | 3/1998 | Moorman et al. |
| 5,730,129 A | 3/1998 | Darrow et al. |
| 5,731,996 A | 3/1998 | Gilbert |
| 5,733,323 A | 3/1998 | Buck et al. |
| 5,738,096 A | 4/1998 | Ben-Haim |
| 5,738,099 A | 4/1998 | Chang |
| 5,740,808 A | 4/1998 | Panescu et al. |
| 5,742,394 A | 4/1998 | Hansen |
| 5,744,953 A | 4/1998 | Hansen |
| 5,748,767 A | 5/1998 | Raab |
| 5,749,835 A | 5/1998 | Glantz |
| 5,749,938 A | 5/1998 | Coombs |
| 5,751,785 A | 5/1998 | Moorman et al. |
| 5,752,513 A | 5/1998 | Acker et al. |
| 5,758,650 A | 6/1998 | Miller et al. |
| 5,762,064 A | 6/1998 | Polvani |
| 5,767,669 A | 6/1998 | Hansen et al. |
| 5,767,960 A | 6/1998 | Orman et al. |
| 5,769,786 A | 6/1998 | Wiegel |
| 5,769,843 A | 6/1998 | Abela et al. |
| 5,769,881 A | 6/1998 | Schroeppel et al. |
| 5,771,896 A | 6/1998 | Sliwa, Jr. et al. |
| 5,775,322 A | 7/1998 | Silverstein et al. |
| 5,775,332 A | 7/1998 | Goldman |
| 5,779,638 A | 7/1998 | Vesely et al. |
| 5,782,767 A | 7/1998 | Pretlow, III |
| 5,782,769 A | 7/1998 | Hwang et al. |
| 5,785,657 A | 7/1998 | Breyer et al. |
| 5,787,049 A | 7/1998 | Bates |
| 5,792,055 A | 8/1998 | McKinnon et al. |
| 5,795,297 A | 8/1998 | Daigle |
| 5,795,298 A | 8/1998 | Vesely et al. |
| 5,795,632 A | 8/1998 | Buchalter |
| 5,797,849 A | 8/1998 | Vesely et al. |
| 5,800,352 A | 9/1998 | Ferre et al. |
| 5,800,410 A | 9/1998 | Gawreluk |
| 5,800,497 A | 9/1998 | Bakels et al. |
| 5,803,089 A | 9/1998 | Ferre et al. |
| 5,810,733 A | 9/1998 | Van Creveld et al. |
| 5,816,245 A | 10/1998 | Manseur et al. |
| 5,817,022 A | 10/1998 | Vesely |
| 5,817,024 A | 10/1998 | Ogle et al. |
| 5,820,549 A | 10/1998 | Marian, Jr. |
| 5,824,031 A | 10/1998 | Cookston et al. |
| 5,829,444 A | 11/1998 | Ferre et al. |
| 5,830,145 A | 11/1998 | Tenhoff |
| 5,831,260 A | 11/1998 | Hansen |
| 5,833,608 A | 11/1998 | Acker |
| 5,833,622 A | 11/1998 | Meathrel et al. |
| 5,835,561 A | 11/1998 | Moorman et al. |
| 5,836,882 A | 11/1998 | Frazin |
| 5,836,990 A | 11/1998 | Li |
| 5,840,024 A | 11/1998 | Taniguchi et al. |
| 5,840,025 A | 11/1998 | Ben-Haim |
| 5,840,030 A | 11/1998 | Ferek-Petric et al. |
| 5,840,031 A | 11/1998 | Crowley |
| 5,842,986 A | 12/1998 | Avrin et al. |
| 5,843,076 A | 12/1998 | Webster, Jr. et al. |
| 5,843,153 A | 12/1998 | Johnston et al. |
| 5,844,140 A | 12/1998 | Seale |
| 5,846,198 A | 12/1998 | Killmann |
| 5,855,553 A | 1/1999 | Tajima et al. |
| 5,855,558 A | 1/1999 | Nakao et al. |
| 5,859,893 A | 1/1999 | Moorman et al. |
| 5,865,748 A | 2/1999 | Co et al. |
| 5,868,673 A | 2/1999 | Vesely |
| 5,873,822 A | 2/1999 | Ferre et al. |
| 5,876,328 A | 3/1999 | Fox et al. |
| 5,879,297 A | 3/1999 | Haynor et al. |
| 5,893,363 A | 4/1999 | Little et al. |
| 5,897,495 A | 4/1999 | Aida et al. |
| 5,899,860 A | 5/1999 | Pfeiffer et al. |
| 5,902,238 A | 5/1999 | Golden et al. |
| 5,907,487 A | 5/1999 | Rosenberg et al. |
| 5,908,385 A | 6/1999 | Chechelski et al. |
| 5,910,113 A | 6/1999 | Pruter |
| 5,910,120 A | 6/1999 | Kim et al. |
| 5,913,820 A | 6/1999 | Bladen et al. |
| 5,913,830 A | 6/1999 | Miles |
| 5,919,141 A | 7/1999 | Money et al. |
| 5,919,170 A | 7/1999 | Woessner |
| 5,928,145 A | 7/1999 | Ocali et al. |
| 5,929,607 A | 7/1999 | Rosenberg et al. |
| 5,931,786 A | 8/1999 | Whitmore, III et al. |
| 5,931,788 A | 8/1999 | Keen et al. |
| 5,931,818 A | 8/1999 | Werp et al. |
| 5,941,858 A | 8/1999 | Johnson |
| 5,941,889 A | 8/1999 | Cermak |
| 5,941,904 A | 8/1999 | Johnston et al. |
| 5,944,022 A | 8/1999 | Nardella et al. |
| 5,944,023 A | 8/1999 | Johnson et al. |
| 5,953,683 A | 9/1999 | Hansen et al. |
| 5,957,857 A | 9/1999 | Hartley |
| 5,961,923 A | 10/1999 | Nova et al. |
| 5,967,978 A | 10/1999 | Littmann et al. |
| 5,967,980 A | 10/1999 | Ferre et al. |
| 5,967,991 A | 10/1999 | Gardineer et al. |
| 5,969,722 A | 10/1999 | Palm |
| 5,978,705 A | 11/1999 | Kenknight et al. |
| 5,982,915 A | 11/1999 | Doi et al. |
| 5,983,126 A | 11/1999 | Wittkampf |
| 5,984,908 A | 11/1999 | Davis et al. |
| 5,991,693 A | 11/1999 | Zalewski |
| 5,997,473 A | 12/1999 | Taniguchi et al. |
| 5,997,481 A | 12/1999 | Adams et al. |
| 6,006,123 A | 12/1999 | Nguyen et al. |
| 6,011,988 A | 1/2000 | Lynch et al. |
| 6,014,473 A | 1/2000 | Hossack et al. |
| 6,014,580 A | 1/2000 | Blume et al. |
| 6,015,414 A | 1/2000 | Werp et al. |
| 6,017,496 A | 1/2000 | Nova et al. |
| 6,019,724 A | 2/2000 | Gronningsaeter et al. |
| 6,019,725 A | 2/2000 | Vesely et al. |
| 6,023,638 A | 2/2000 | Swanson |
| 6,026,312 A | 2/2000 | Shemwell et al. |
| 6,031,765 A | 2/2000 | Lee et al. |
| 6,032,070 A | 2/2000 | Flock et al. |
| 6,039,694 A | 3/2000 | Larson et al. |
| 6,050,718 A | 4/2000 | Schena et al. |
| 6,052,610 A | 4/2000 | Koch |
| 6,052,618 A | 4/2000 | Dahlke et al. |
| D424,693 S | 5/2000 | Pruter |
| 6,059,718 A | 5/2000 | Taniguchi et al. |
| 6,064,903 A | 5/2000 | Riechers et al. |
| 6,064,905 A | 5/2000 | Webster, Jr. et al. |
| 6,066,094 A | 5/2000 | Ben-Haim |
| 6,068,599 A | 5/2000 | Saito et al. |
| 6,073,043 A | 6/2000 | Schneider |
| 6,074,367 A | 6/2000 | Hubbell |
| 6,075,442 A | 6/2000 | Welch |
| 6,076,007 A | 6/2000 | England et al. |
| 6,082,366 A | 7/2000 | Andra et al. |
| 6,083,170 A | 7/2000 | Ben-Haim |
| 6,099,524 A | 8/2000 | Lipson et al. |
| 6,100,026 A | 8/2000 | Nova et al. |
| 6,102,044 A | 8/2000 | Naidyhorski |
| 6,106,472 A | 8/2000 | Chiang et al. |
| 6,107,699 A | 8/2000 | Swanson |
| 6,112,111 A | 8/2000 | Glantz |
| 6,113,504 A | 9/2000 | Kuesters |
| 6,113,547 A | 9/2000 | Catallo et al. |
| 6,115,624 A | 9/2000 | Lewis et al. |
| 6,117,085 A | 9/2000 | Picatli et al. |
| 6,120,445 A | 9/2000 | Grunwald |
| 6,126,608 A | 10/2000 | Kemme et al. |
| 6,128,174 A | 10/2000 | Ritter et al. |
| 6,129,668 A | 10/2000 | Haynor et al. |

(56) References Cited

U.S. PATENT DOCUMENTS

| | | |
|---|---|---|
| 6,132,378 A | 10/2000 | Marino |
| 6,132,379 A | 10/2000 | Patacsil et al. |
| 6,135,961 A | 10/2000 | Pflugrath et al. |
| 6,136,274 A | 10/2000 | Nova et al. |
| 6,138,681 A | 10/2000 | Chen et al. |
| 6,139,496 A | 10/2000 | Chen et al. |
| 6,139,502 A | 10/2000 | Fredriksen |
| 6,142,946 A | 11/2000 | Hwang et al. |
| 6,144,300 A | 11/2000 | Dames et al. |
| 6,148,823 A | 11/2000 | Hastings |
| 6,152,933 A | 11/2000 | Werp et al. |
| 6,157,853 A | 12/2000 | Blume et al. |
| 6,165,144 A | 12/2000 | Talish et al. |
| 6,166,496 A | 12/2000 | Lys et al. |
| 6,166,806 A | 12/2000 | Tjin |
| 6,167,765 B1 | 1/2001 | Weitzel |
| 6,172,499 B1 | 1/2001 | Ashe |
| 6,173,199 B1 | 1/2001 | Gabriel |
| 6,173,715 B1 | 1/2001 | Sinanan et al. |
| 6,175,756 B1 | 1/2001 | Ferre et al. |
| 6,176,829 B1 | 1/2001 | Vilkomerson |
| 6,193,743 B1 | 2/2001 | Brayton et al. |
| 6,200,305 B1 | 3/2001 | Berthiaume et al. |
| 6,203,498 B1 | 3/2001 | Bunce et al. |
| 6,203,499 B1 | 3/2001 | Imling et al. |
| 6,206,843 B1 | 3/2001 | Iger et al. |
| 6,208,884 B1 | 3/2001 | Kumar et al. |
| 6,211,626 B1 | 4/2001 | Lys et al. |
| 6,211,666 B1 | 4/2001 | Acker |
| 6,212,426 B1 | 4/2001 | Swanson |
| 6,216,027 B1 | 4/2001 | Willis et al. |
| 6,216,028 B1 | 4/2001 | Haynor et al. |
| 6,216,029 B1 | 4/2001 | Paltieli |
| 6,223,087 B1 | 4/2001 | Williams |
| 6,226,547 B1 | 5/2001 | Lockhart et al. |
| 6,230,046 B1 | 5/2001 | Crane et al. |
| 6,233,476 B1 | 5/2001 | Strommer et al. |
| 6,233,479 B1 | 5/2001 | Haddad et al. |
| 6,238,344 B1 | 5/2001 | Gamelsky et al. |
| 6,241,673 B1 | 6/2001 | Williams |
| 6,246,231 B1 | 6/2001 | Ashe |
| 6,246,898 B1 | 6/2001 | Vesely et al. |
| 6,248,072 B1 | 6/2001 | Murkin |
| 6,248,074 B1 | 6/2001 | Ohno et al. |
| 6,248,075 B1 | 6/2001 | McGee et al. |
| 6,251,073 B1 | 6/2001 | Imran et al. |
| 6,253,770 B1 | 7/2001 | Acker et al. |
| 6,259,941 B1 | 7/2001 | Chia et al. |
| 6,261,231 B1 | 7/2001 | Damphousse et al. |
| 6,263,230 B1 | 7/2001 | Haynor et al. |
| 6,266,550 B1 | 7/2001 | Selmon et al. |
| 6,266,551 B1 | 7/2001 | Osadchy et al. |
| 6,266,552 B1 | 7/2001 | Slettenmark |
| 6,266,563 B1 | 7/2001 | KenKnight et al. |
| 6,271,833 B1 | 8/2001 | Rosenberg et al. |
| 6,272,371 B1 | 8/2001 | Shlomo |
| 6,272,374 B1 | 8/2001 | Flock et al. |
| 6,275,258 B1 | 8/2001 | Chim |
| 6,275,724 B1 | 8/2001 | Dickinson et al. |
| 6,277,077 B1 | 8/2001 | Brisken et al. |
| 6,284,459 B1 | 9/2001 | Nova et al. |
| 6,285,898 B1 | 9/2001 | Ben-Haim |
| 6,288,704 B1 | 9/2001 | Flack et al. |
| 6,292,678 B1 | 9/2001 | Hall et al. |
| 6,292,680 B1 | 9/2001 | Somogyi et al. |
| 6,292,901 B1 | 9/2001 | Lys et al. |
| 6,293,955 B1 | 9/2001 | Houser et al. |
| 6,296,604 B1 | 10/2001 | Garibaldi et al. |
| 6,296,614 B1 | 10/2001 | Pruter |
| 6,298,261 B1 | 10/2001 | Rex |
| 6,304,768 B1 | 10/2001 | Blume et al. |
| 6,306,097 B1 | 10/2001 | Park et al. |
| 6,311,082 B1 | 10/2001 | Creighton, IV et al. |
| 6,315,709 B1 | 11/2001 | Garibaldi et al. |
| 6,315,727 B1 | 11/2001 | Coleman et al. |
| 6,319,668 B1 | 11/2001 | Nova et al. |
| 6,323,769 B1 | 11/2001 | Dames et al. |
| 6,323,770 B1 | 11/2001 | Dames et al. |
| 6,324,416 B1 | 11/2001 | Seibert |
| 6,325,540 B1 | 12/2001 | Lounsberry et al. |
| 6,325,762 B1 | 12/2001 | Tjin |
| 6,329,139 B1 | 12/2001 | Nova et al. |
| 6,329,916 B1 | 12/2001 | Dames et al. |
| 6,330,467 B1 | 12/2001 | Creighton, IV et al. |
| 6,332,089 B1 | 12/2001 | Acker et al. |
| 6,332,874 B1 | 12/2001 | Eliasen et al. |
| 6,340,588 B1 | 1/2002 | Nova et al. |
| 6,340,868 B1 | 1/2002 | Lys et al. |
| 6,341,231 B1 | 1/2002 | Ferre et al. |
| 6,346,081 B1 | 2/2002 | Vilkomerson |
| 6,348,911 B1 | 2/2002 | Rosenberg et al. |
| 6,350,160 B1 | 2/2002 | Feuersanger et al. |
| 6,352,363 B1 | 3/2002 | Munger et al. |
| 6,355,026 B1 | 3/2002 | Mick |
| 6,361,499 B1 | 3/2002 | Bates et al. |
| 6,364,823 B1 | 4/2002 | Garibaldi et al. |
| 6,364,839 B1 | 4/2002 | Little et al. |
| 6,366,804 B1 | 4/2002 | Mejia |
| 6,368,285 B1 | 4/2002 | Osadchy et al. |
| 6,370,411 B1 | 4/2002 | Osadchy et al. |
| 6,373,240 B1 | 4/2002 | Govari |
| 6,373,388 B1 | 4/2002 | Dames et al. |
| 6,374,134 B1 | 4/2002 | Bladen et al. |
| 6,374,670 B1 | 4/2002 | Spelman et al. |
| 6,375,606 B1 | 4/2002 | Garibaldi et al. |
| 6,375,639 B1 | 4/2002 | Duplessie et al. |
| 6,377,857 B1 | 4/2002 | Brayton et al. |
| 6,379,302 B1 | 4/2002 | Kessman et al. |
| 6,379,303 B1 | 4/2002 | Seitz et al. |
| 6,379,307 B1 | 4/2002 | Filly et al. |
| 6,381,485 B1 | 4/2002 | Hunter et al. |
| 6,383,139 B1 | 5/2002 | Hwang et al. |
| 6,385,472 B1 | 5/2002 | Hall et al. |
| 6,385,476 B1 | 5/2002 | Osadchy et al. |
| 6,398,736 B1 | 6/2002 | Seward |
| 6,401,723 B1 | 6/2002 | Garibaldi et al. |
| 6,406,442 B1 | 6/2002 | McFann et al. |
| 6,412,978 B1 | 7/2002 | Watanabe et al. |
| 6,412,980 B1 | 7/2002 | Lounsberry et al. |
| 6,416,475 B1 | 7/2002 | Hwang et al. |
| 6,417,839 B1 | 7/2002 | Odell |
| 6,418,332 B1 | 7/2002 | Mastrototaro et al. |
| 6,418,335 B2 | 7/2002 | Avrin et al. |
| 6,423,002 B1 | 7/2002 | Hossack |
| 6,423,050 B1 | 7/2002 | Twardowski |
| 6,427,079 B1 | 7/2002 | Schneider et al. |
| 6,428,551 B1 | 8/2002 | Hall et al. |
| 6,430,315 B1 | 8/2002 | Makram-Ebeid |
| 6,432,069 B1 | 8/2002 | Godo et al. |
| 6,436,050 B2 | 8/2002 | Garrison et al. |
| 6,438,411 B1 | 8/2002 | Guttman et al. |
| 6,442,416 B1 | 8/2002 | Schultz |
| 6,443,902 B1 | 9/2002 | Sasady |
| 6,443,907 B1 | 9/2002 | Mansy et al. |
| 6,445,943 B1 | 9/2002 | Ferre et al. |
| 6,459,919 B1 | 10/2002 | Lys et al. |
| 6,463,121 B1 | 10/2002 | Milnes |
| 6,473,167 B1 | 10/2002 | Odell |
| 6,474,341 B1 | 11/2002 | Hunter et al. |
| 6,475,146 B1 | 11/2002 | Frelburger et al. |
| 6,475,152 B1 | 11/2002 | Kelly, Jr. et al. |
| 6,475,223 B1 | 11/2002 | Werp et al. |
| 6,477,402 B1 | 11/2002 | Lynch et al. |
| 6,484,118 B1 | 11/2002 | Govari et al. |
| 6,485,426 B2 | 11/2002 | Sandhu |
| 6,487,916 B1 | 12/2002 | Gomm et al. |
| 6,491,671 B1 | 12/2002 | Larson, III et al. |
| 6,493,573 B1 | 12/2002 | Martinelli et al. |
| 6,496,715 B1 | 12/2002 | Lee et al. |
| 6,498,944 B1 | 12/2002 | Ben-Haim et al. |
| 6,500,141 B1 | 12/2002 | Irion et al. |
| 6,505,062 B1 | 1/2003 | Ritter et al. |
| 6,507,751 B2 | 1/2003 | Blume et al. |
| 6,508,802 B1 | 1/2003 | Rosengart et al. |

(56) References Cited

U.S. PATENT DOCUMENTS

| | | |
|---|---|---|
| 6,512,958 B1 | 1/2003 | Swoyer et al. |
| 6,514,249 B1 | 2/2003 | Maguire et al. |
| 6,515,657 B1 | 2/2003 | Zanelli |
| 6,516,212 B1 | 2/2003 | Bladen et al. |
| 6,516,231 B1 | 2/2003 | Flammang |
| 6,516,807 B1 | 2/2003 | Panescu et al. |
| 6,517,491 B1 | 2/2003 | Thiele et al. |
| 6,517,520 B2 | 2/2003 | Chang et al. |
| 6,522,906 B1 | 2/2003 | Salisbury, Jr. et al. |
| 6,522,907 B1 | 2/2003 | Bladen et al. |
| 6,522,909 B1 | 2/2003 | Garibaldi et al. |
| 6,524,303 B1 | 2/2003 | Garibaldi |
| 6,528,954 B1 | 3/2003 | Lys et al. |
| 6,528,991 B2 | 3/2003 | Ashe |
| 6,529,761 B2 | 3/2003 | Creighton, IV et al. |
| 6,530,887 B1 | 3/2003 | Gilbert et al. |
| 6,534,982 B1 | 3/2003 | Jakab |
| 6,535,625 B1 | 3/2003 | Chang et al. |
| 6,537,192 B1 | 3/2003 | Elliott et al. |
| 6,537,196 B1 | 3/2003 | Creighton, IV et al. |
| 6,538,634 B1 | 3/2003 | Chui et al. |
| 6,540,685 B1 | 4/2003 | Rhoads et al. |
| 6,540,699 B1 | 4/2003 | Smith et al. |
| 6,542,766 B2 | 4/2003 | Hall et al. |
| 6,544,251 B1 | 4/2003 | Crawford |
| 6,546,270 B1 | 4/2003 | Goldin et al. |
| 6,546,279 B1 | 4/2003 | Bova et al. |
| 6,546,787 B1 | 4/2003 | Schiller et al. |
| 6,549,794 B1 | 4/2003 | Nadeau, Jr. et al. |
| 6,552,841 B1 | 4/2003 | Lasser et al. |
| 6,556,858 B1 | 4/2003 | Zeman |
| 6,562,019 B1 | 5/2003 | Sell |
| 6,564,087 B1 | 5/2003 | Pitris et al. |
| 6,569,101 B2 | 5/2003 | Quistgaard et al. |
| 6,571,004 B1 | 5/2003 | Florent et al. |
| 6,574,518 B1 | 6/2003 | Lounsberry et al. |
| 6,575,908 B2 | 6/2003 | Barnes et al. |
| 6,577,080 B2 | 6/2003 | Lys et al. |
| 6,577,896 B2 | 6/2003 | Werner et al. |
| 6,584,343 B1 | 6/2003 | Ransbury et al. |
| 6,593,754 B1 | 7/2003 | Steber et al. |
| 6,593,884 B1 | 7/2003 | Gilboa et al. |
| 6,596,791 B2 | 7/2003 | Santar et al. |
| 6,597,943 B2 | 7/2003 | Taha et al. |
| 6,599,249 B1 | 7/2003 | Nordgren et al. |
| 6,607,488 B1 | 8/2003 | Jackson et al. |
| 6,610,058 B2 | 8/2003 | Flores |
| 6,611,141 B1 | 8/2003 | Schulz et al. |
| 6,615,071 B1 | 9/2003 | Casscells, III et al. |
| 6,615,155 B2 | 9/2003 | Gilboa |
| 6,618,612 B1 | 9/2003 | Acker et al. |
| 6,626,832 B1 | 9/2003 | Paltieli et al. |
| 6,626,834 B2 | 9/2003 | Dunne et al. |
| 6,626,902 B1 | 9/2003 | Kucharczyk et al. |
| 6,630,879 B1 | 10/2003 | Creighton, IV et al. |
| 6,635,027 B1 | 10/2003 | Cragg et al. |
| 6,645,148 B2 | 11/2003 | Nguyen-Dinh et al. |
| 6,648,875 B2 | 11/2003 | Simpson et al. |
| 6,649,914 B1 | 11/2003 | Moorman et al. |
| 6,652,506 B2 | 11/2003 | Bowe et al. |
| 6,662,034 B2 | 12/2003 | Segner et al. |
| 6,669,633 B2 | 12/2003 | Brodsky et al. |
| 6,672,308 B1 | 1/2004 | Gaspari |
| 6,677,752 B1 | 1/2004 | Creighton, IV et al. |
| 6,679,857 B1 | 1/2004 | Bastia et al. |
| 6,684,176 B2 | 1/2004 | Willins et al. |
| 6,685,644 B2 | 2/2004 | Seo |
| 6,687,531 B1 | 2/2004 | Ferre et al. |
| 6,689,119 B1 | 2/2004 | Di Caprio et al. |
| 6,690,963 B2 | 2/2004 | Ben-Haim et al. |
| 6,690,964 B2 | 2/2004 | Bieger et al. |
| 6,690,968 B2 | 2/2004 | Mejia |
| 6,694,167 B1 | 2/2004 | Ferre et al. |
| 6,695,786 B2 | 2/2004 | Wang et al. |
| 6,701,179 B1 | 3/2004 | Martinelli et al. |
| 6,701,918 B2 | 3/2004 | Fariss et al. |
| 6,702,749 B2 | 3/2004 | Paladini et al. |
| 6,702,804 B1 | 3/2004 | Ritter et al. |
| 6,704,590 B2 | 3/2004 | Haldeman |
| 6,709,390 B1 | 3/2004 | Marie Pop |
| 6,711,429 B1 | 3/2004 | Gilboa et al. |
| 6,711,431 B2 | 3/2004 | Sarin et al. |
| 6,719,698 B2 | 4/2004 | Manor et al. |
| 6,719,699 B2 | 4/2004 | Smith |
| 6,719,724 B1 | 4/2004 | Walker et al. |
| 6,719,756 B1 | 4/2004 | Muntermann |
| 6,720,745 B2 | 4/2004 | Lys et al. |
| 6,733,511 B2 | 5/2004 | Hall et al. |
| 6,736,782 B2 | 5/2004 | Pfeiffer et al. |
| 6,738,656 B1 | 5/2004 | Ferre et al. |
| 6,740,103 B2 | 5/2004 | Hall et al. |
| 6,743,177 B2 | 6/2004 | Ito et al. |
| 6,746,402 B2 | 6/2004 | Ustuner |
| 6,754,596 B2 | 6/2004 | Ashe |
| 6,755,789 B2 | 6/2004 | Stringer et al. |
| 6,755,816 B2 | 6/2004 | Ritter et al. |
| 6,757,557 B1 | 6/2004 | Bladen et al. |
| 6,763,261 B2 | 7/2004 | Casscells, III et al. |
| 6,764,449 B2 | 7/2004 | Lee et al. |
| 6,768,496 B2 | 7/2004 | Bieger et al. |
| 6,772,001 B2 | 8/2004 | Maschke et al. |
| 6,774,624 B2 | 8/2004 | Anderson et al. |
| 6,780,154 B2 | 8/2004 | Hunt et al. |
| 6,783,493 B2 | 8/2004 | Chiang et al. |
| 6,783,536 B2 | 8/2004 | Vilsmeier et al. |
| 6,784,660 B2 | 8/2004 | Ashe |
| 6,785,571 B2 | 8/2004 | Glossop et al. |
| 6,786,219 B2 | 9/2004 | Garibaldi et al. |
| 6,788,967 B2 | 9/2004 | Ben-Haim et al. |
| 6,794,667 B2 | 9/2004 | Noshi |
| 6,799,066 B2 | 9/2004 | Steines et al. |
| 6,814,704 B2 | 11/2004 | Weilandt |
| 6,815,651 B2 | 11/2004 | Odell |
| 6,816,266 B2 | 11/2004 | Varshneya et al. |
| 6,817,364 B2 | 11/2004 | Garibaldi |
| 6,832,199 B1 | 12/2004 | Kucek et al. |
| 6,834,201 B2 | 12/2004 | Gillies et al. |
| 6,844,713 B2 | 1/2005 | Steber et al. |
| 6,845,142 B2 | 1/2005 | Ohishi |
| 6,856,823 B2 | 2/2005 | Ashe |
| 6,860,422 B2 | 3/2005 | Hull et al. |
| 6,862,467 B2 | 3/2005 | Moore et al. |
| 6,869,390 B2 | 3/2005 | Elliott et al. |
| 6,869,401 B2 | 3/2005 | Gilbert et al. |
| 6,875,179 B2 | 4/2005 | Ferguson et al. |
| 6,879,160 B2 | 4/2005 | Jakab |
| 6,884,219 B1 | 4/2005 | Pruter |
| 6,889,091 B2 | 5/2005 | Hine et al. |
| 6,895,268 B1 | 5/2005 | Rahn et al. |
| 6,902,528 B1 | 6/2005 | Garibaldi et al. |
| 6,908,433 B1 | 6/2005 | Pruter |
| 6,911,026 B1 | 6/2005 | Hall et al. |
| 6,923,782 B2 | 8/2005 | O'Mahony et al. |
| 6,926,673 B2 | 8/2005 | Roberts et al. |
| 6,934,575 B2 | 8/2005 | Ferre et al. |
| 6,936,010 B2 | 8/2005 | Fang et al. |
| 6,940,379 B2 | 9/2005 | Creighton |
| 6,941,166 B2 | 9/2005 | MacAdam et al. |
| 6,947,788 B2 | 9/2005 | Gilboa et al. |
| 6,950,689 B1 | 9/2005 | Willis et al. |
| 6,953,754 B2 | 10/2005 | Machida et al. |
| 6,958,677 B1 | 10/2005 | Carter |
| 6,959,214 B2 | 10/2005 | Pape et al. |
| 6,962,566 B2 | 11/2005 | Quistgaard et al. |
| 6,968,846 B2 | 11/2005 | Viswanathan |
| 6,969,352 B2 | 11/2005 | Chiang et al. |
| 6,975,197 B2 | 12/2005 | Creighton, IV |
| 6,976,962 B2 | 12/2005 | Bullis |
| 6,976,987 B2 | 12/2005 | Flores |
| 6,980,843 B2 | 12/2005 | Eng et al. |
| 6,980,852 B2 | 12/2005 | Jersey-Willuhn et al. |
| 6,980,921 B2 | 12/2005 | Anderson et al. |
| 6,986,739 B2 | 1/2006 | Warren et al. |
| 6,999,821 B2 | 2/2006 | Jenney et al. |

(56) References Cited

U.S. PATENT DOCUMENTS

| | | |
|---|---|---|
| 7,001,355 B2 | 2/2006 | Nunomura et al. |
| 7,008,418 B2 | 3/2006 | Hall et al. |
| 7,010,338 B2 | 3/2006 | Ritter et al. |
| 7,015,393 B2 | 3/2006 | Weiner et al. |
| 7,017,584 B2 | 3/2006 | Garibaldi et al. |
| 7,019,610 B2 | 3/2006 | Creighton, IV et al. |
| 7,020,512 B2 | 3/2006 | Ritter et al. |
| D518,574 S | 4/2006 | Chaggares |
| 7,022,075 B2 | 4/2006 | Grunwald et al. |
| 7,022,082 B2 | 4/2006 | Sonek |
| 7,026,927 B2 | 4/2006 | Wright et al. |
| 7,027,634 B2 | 4/2006 | Odell |
| 7,028,387 B1 | 4/2006 | Huynh et al. |
| 7,029,446 B2 | 4/2006 | Wendelken et al. |
| 7,033,603 B2 | 4/2006 | Nelson et al. |
| D520,139 S | 5/2006 | Chaggares |
| D520,140 S | 5/2006 | Chaggares |
| 7,038,398 B1 | 5/2006 | Lys et al. |
| 7,038,657 B2 | 5/2006 | Rosenberg et al. |
| 7,043,293 B1 | 5/2006 | Baura |
| 7,054,228 B1 | 5/2006 | Hickling |
| 7,066,914 B2 | 6/2006 | Andersen |
| 7,066,924 B1 | 6/2006 | Garibaldi et al. |
| D525,363 S | 7/2006 | Chaggares |
| 7,070,565 B2 | 7/2006 | Vaezy et al. |
| 7,072,704 B2 | 7/2006 | Bucholz |
| 7,082,325 B2 | 7/2006 | Hashimshony et al. |
| 7,090,639 B2 | 8/2006 | Govari |
| 7,096,148 B2 | 8/2006 | Anderson et al. |
| 7,096,870 B2 | 8/2006 | Lamprich et al. |
| 7,098,907 B2 | 8/2006 | Houston et al. |
| 7,103,205 B2 | 9/2006 | Wang et al. |
| 7,104,980 B1 | 9/2006 | Laherty et al. |
| 7,106,043 B1 | 9/2006 | Da Silva et al. |
| 7,106,431 B2 | 9/2006 | Odell |
| 7,106,479 B2 | 9/2006 | Roy et al. |
| 7,107,105 B2 | 9/2006 | Bjorklund et al. |
| 7,132,804 B2 | 11/2006 | Lys et al. |
| 7,137,976 B2 | 11/2006 | Ritter et al. |
| 7,141,812 B2 | 11/2006 | Appleby et al. |
| 7,142,905 B2 | 11/2006 | Slayton et al. |
| 7,148,970 B2 | 12/2006 | de Boer |
| 7,153,291 B2 | 12/2006 | Bierman |
| 7,161,453 B2 | 1/2007 | Creighton, IV |
| 7,162,291 B1 | 1/2007 | Nachaliel |
| 7,167,738 B2 | 1/2007 | Schweikard et al. |
| 7,169,107 B2 | 1/2007 | Jersey-Willuhn et al. |
| 7,174,201 B2 | 2/2007 | Govari et al. |
| 7,175,646 B2 | 2/2007 | Brenneman et al. |
| 7,180,252 B2 | 2/2007 | Lys et al. |
| 7,184,820 B2 | 2/2007 | Jersey-Willuhn et al. |
| 7,189,198 B2 | 3/2007 | Harburn et al. |
| 7,190,819 B2 | 3/2007 | Viswanathan |
| 7,194,295 B2 | 3/2007 | Vilsmeier |
| 7,204,798 B2 | 4/2007 | Zdeblick et al. |
| 7,206,064 B2 | 4/2007 | Rogers et al. |
| 7,207,941 B2 | 4/2007 | Sharf |
| 7,211,082 B2 | 5/2007 | Hall et al. |
| 7,214,191 B2 | 5/2007 | Stringer et al. |
| 7,215,326 B2 | 5/2007 | Rosenberg |
| 7,221,104 B2 | 5/2007 | Lys et al. |
| 7,223,256 B2 | 5/2007 | Bierman |
| 7,229,400 B2 | 6/2007 | Elliott et al. |
| 7,231,243 B2 | 6/2007 | Tearney et al. |
| 7,236,157 B2 | 6/2007 | Schena et al. |
| 7,236,816 B2 | 6/2007 | Kumar et al. |
| 7,237,313 B2 | 7/2007 | Skujins et al. |
| 7,241,267 B2 | 7/2007 | Furia |
| 7,244,234 B2 | 7/2007 | Ridley et al. |
| 7,248,032 B1 | 7/2007 | Hular et al. |
| 7,248,914 B2 | 7/2007 | Hastings et al. |
| 7,264,584 B2 | 9/2007 | Ritter et al. |
| 7,270,662 B2 | 9/2007 | Visram et al. |
| 7,275,682 B2 | 10/2007 | Excoffier et al. |
| 7,276,044 B2 | 10/2007 | Ferry et al. |
| 7,286,034 B2 | 10/2007 | Creighton |
| 7,291,146 B2 | 11/2007 | Steinke et al. |
| 7,297,140 B2 | 11/2007 | Orlu et al. |
| 7,308,296 B2 | 12/2007 | Lys et al. |
| 7,310,150 B2 | 12/2007 | Guillermo et al. |
| 7,321,228 B2 | 1/2008 | Govari |
| 7,322,990 B1 | 1/2008 | Mark et al. |
| 7,342,058 B2 | 3/2008 | Peppmoller et al. |
| D566,284 S | 4/2008 | Kitayama et al. |
| 7,355,716 B2 | 4/2008 | de Boer et al. |
| 7,360,427 B2 | 4/2008 | Drinkwater et al. |
| 7,366,376 B2 | 4/2008 | Shishkov et al. |
| 7,366,562 B2 | 4/2008 | Dukesherer et al. |
| 7,366,563 B2 | 4/2008 | Kleen et al. |
| 7,373,271 B1 | 5/2008 | Schneider |
| 7,382,949 B2 | 6/2008 | Bouma et al. |
| 7,418,169 B2 | 8/2008 | Tearney et al. |
| 7,447,408 B2 | 11/2008 | Bouma et al. |
| 7,452,331 B1 | 11/2008 | Pruter |
| 7,452,358 B2 | 11/2008 | Stern et al. |
| D585,556 S | 1/2009 | Kosaku |
| 7,479,141 B2 | 1/2009 | Kleen et al. |
| 7,534,223 B2 | 5/2009 | Boutilette et al. |
| 7,538,859 B2 | 5/2009 | Tearney et al. |
| 7,547,282 B2 | 6/2009 | Lo et al. |
| 7,551,293 B2 | 6/2009 | Yelin et al. |
| D599,909 S | 9/2009 | Rinott et al. |
| 7,588,541 B2 | 9/2009 | Floyd et al. |
| D603,050 S | 10/2009 | Chen |
| 7,599,730 B2 | 10/2009 | Hunter et al. |
| 7,604,596 B2 | 10/2009 | Hwang et al. |
| D603,520 S | 11/2009 | Ninomiya et al. |
| 7,635,336 B1 | 12/2009 | Pruter |
| 7,637,163 B2 | 12/2009 | Fetzer et al. |
| 7,640,053 B2 | 12/2009 | Verin |
| 7,651,469 B2 | 1/2010 | Osborne et al. |
| 7,652,080 B2 | 1/2010 | Peppmoller et al. |
| D609,814 S | 2/2010 | Banryu |
| 7,665,893 B2 | 2/2010 | Buchalter |
| 7,668,583 B2 | 2/2010 | Fegert et al. |
| 7,670,294 B2 | 3/2010 | Kisen et al. |
| 7,686,766 B2 | 3/2010 | Quistgaard et al. |
| 7,691,066 B2 | 4/2010 | Kosaku |
| 7,699,782 B2 | 4/2010 | Angelsen et al. |
| 7,727,192 B2 | 6/2010 | Tokumoto et al. |
| 7,740,586 B2 | 6/2010 | Hwang et al. |
| 7,751,865 B2 | 7/2010 | Jascob et al. |
| 7,766,839 B2 | 8/2010 | Rogers et al. |
| 7,774,051 B2 | 8/2010 | Voth |
| 7,794,407 B2 | 9/2010 | Rothenberg |
| 7,798,970 B2 | 9/2010 | Lo et al. |
| 7,819,807 B2 | 10/2010 | Barnes et al. |
| 7,819,810 B2 | 10/2010 | Stringer et al. |
| 7,837,627 B1 | 11/2010 | Pruter |
| D629,526 S | 12/2010 | Ladwig et al. |
| D629,527 S | 12/2010 | Crunkilton |
| 7,846,103 B2 | 12/2010 | Cannon, Jr. et al. |
| 7,850,613 B2 | 12/2010 | Stribling |
| D630,756 S | 1/2011 | Kitayama |
| D630,757 S | 1/2011 | Kitayama |
| 7,909,815 B2 | 3/2011 | Whitmore, III et al. |
| 7,931,596 B2 | 4/2011 | Rachlin et al. |
| 7,976,469 B2 | 7/2011 | Bonde et al. |
| 7,998,073 B2 | 8/2011 | Roth et al. |
| 8,052,606 B2 | 11/2011 | Barnes et al. |
| 8,073,529 B2 | 12/2011 | Cermak et al. |
| 8,118,743 B2 | 2/2012 | Park et al. |
| 8,137,281 B2 | 3/2012 | Huang et al. |
| 8,147,408 B2 | 4/2012 | Bunce et al. |
| 8,216,146 B2 | 7/2012 | Hwang et al. |
| 8,257,264 B2 | 9/2012 | Park et al. |
| 8,353,840 B2 | 1/2013 | Pruter |
| 8,388,541 B2 | 3/2013 | Messerly et al. |
| 8,388,546 B2 | 3/2013 | Rothenberg |
| 8,430,889 B2 | 4/2013 | Zeng et al. |
| 8,437,833 B2 | 5/2013 | Silverstein |
| 8,449,531 B2 | 5/2013 | Whitmore, III et al. |
| D684,265 S | 6/2013 | Cadera |
| 8,478,382 B2 | 7/2013 | Burnside et al. |

(56) References Cited

U.S. PATENT DOCUMENTS

| | | |
|---|---|---|
| 8,496,592 B2 | 7/2013 | Ridley et al. |
| 8,496,593 B2 | 7/2013 | Park et al. |
| 8,512,256 B2 | 8/2013 | Rothenberg |
| 8,801,693 B2 | 8/2014 | He et al. |
| D724,745 S | 3/2015 | Orome et al. |
| D727,495 S | 4/2015 | Bown et al. |
| 10,022,147 B2 | 7/2018 | Lee |
| 10,639,008 B2 | 5/2020 | Lindekugel et al. |
| 2001/0053915 A1 | 12/2001 | Grossman |
| 2002/0019447 A1 | 2/2002 | Renn et al. |
| 2002/0022777 A1 | 2/2002 | Crieghton et al. |
| 2002/0032391 A1 | 3/2002 | McFann et al. |
| 2002/0038088 A1 | 3/2002 | Imran et al. |
| 2002/0055680 A1 | 5/2002 | Miele et al. |
| 2002/0082559 A1 | 6/2002 | Chang et al. |
| 2002/0097926 A1 | 7/2002 | Mochizuki |
| 2002/0113555 A1 | 8/2002 | Lys et al. |
| 2002/0114518 A1 | 8/2002 | Wilt |
| 2002/0120193 A1 | 8/2002 | Chiang et al. |
| 2002/0123679 A1 | 9/2002 | Dominguez |
| 2002/0128554 A1 | 9/2002 | Seward |
| 2002/0133079 A1 | 9/2002 | Sandhu |
| 2002/0151789 A1 | 10/2002 | Mansy et al. |
| 2002/0156363 A1 | 10/2002 | Hunter et al. |
| 2002/0156376 A1 | 10/2002 | Wang et al. |
| 2002/0165448 A1 | 11/2002 | Ben-Haim et al. |
| 2002/0165534 A1 | 11/2002 | Hayzelden et al. |
| 2002/0198568 A1 | 12/2002 | Hafer et al. |
| 2003/0002727 A1 | 1/2003 | MacMahon |
| 2003/0009132 A1 | 1/2003 | Schwartz et al. |
| 2003/0011359 A1 | 1/2003 | Ashe |
| 2003/0013966 A1 | 1/2003 | Barnes et al. |
| 2003/0018276 A1 | 1/2003 | Mansy et al. |
| 2003/0028113 A1 | 2/2003 | Gilbert et al. |
| 2003/0036696 A1 | 2/2003 | Willis et al. |
| 2003/0040671 A1 | 2/2003 | Somogyi et al. |
| 2003/0072805 A1 | 4/2003 | Miyazawa et al. |
| 2003/0073894 A1 | 4/2003 | Chiang et al. |
| 2003/0076281 A1 | 4/2003 | Morgan et al. |
| 2003/0083698 A1 | 5/2003 | Whitehurst et al. |
| 2003/0088195 A1 | 5/2003 | Vardi et al. |
| 2003/0100849 A1 | 5/2003 | Jang |
| 2003/0114742 A1 | 6/2003 | Lewkowicz et al. |
| 2003/0114777 A1 | 6/2003 | Griffin et al. |
| 2003/0120150 A1 | 6/2003 | Govari |
| 2003/0120154 A1 | 6/2003 | Sauer et al. |
| 2003/0139661 A1 | 7/2003 | Kimchy et al. |
| 2003/0139664 A1 | 7/2003 | Hunt et al. |
| 2003/0149328 A1 | 8/2003 | Elliott et al. |
| 2003/0149359 A1 | 8/2003 | Smith |
| 2003/0152290 A1 | 8/2003 | Odell |
| 2003/0158482 A1 | 8/2003 | Poland et al. |
| 2003/0160721 A1 | 8/2003 | Gilboa et al. |
| 2003/0163037 A1 | 8/2003 | Bladen et al. |
| 2003/0171681 A1 | 9/2003 | Weilandt |
| 2003/0171691 A1 | 9/2003 | Casscells et al. |
| 2003/0173953 A1 | 9/2003 | Ashe |
| 2003/0176787 A1 | 9/2003 | Gilbert et al. |
| 2003/0184544 A1 | 10/2003 | Prudent |
| 2003/0191392 A1 | 10/2003 | Haldeman |
| 2003/0191460 A1 | 10/2003 | Hobbs et al. |
| 2003/0195418 A1 | 10/2003 | Barnes et al. |
| 2003/0195420 A1 | 10/2003 | Mendlein et al. |
| 2003/0199746 A1 | 10/2003 | Fuimaono et al. |
| 2003/0208142 A1 | 11/2003 | Boudewijn et al. |
| 2003/0216639 A1 | 11/2003 | Gilboa et al. |
| 2003/0220557 A1 | 11/2003 | Cleary et al. |
| 2003/0220578 A1 | 11/2003 | Ho et al. |
| 2003/0229298 A1 | 12/2003 | Iwami et al. |
| 2003/0233042 A1 | 12/2003 | Ashe |
| 2004/0015070 A1 | 1/2004 | Liang et al. |
| 2004/0015079 A1 | 1/2004 | Berger et al. |
| 2004/0024301 A1 | 2/2004 | Hockett et al. |
| 2004/0030319 A1 | 2/2004 | Korkor et al. |
| 2004/0043688 A1 | 3/2004 | Soerens et al. |
| 2004/0054278 A1 | 3/2004 | Kimchy et al. |
| 2004/0059226 A1 | 3/2004 | Peszynski et al. |
| 2004/0082916 A1 | 4/2004 | Jenkins |
| 2004/0087877 A1 | 5/2004 | Besz et al. |
| 2004/0088136 A1 | 5/2004 | Ashe |
| 2004/0097803 A1 | 5/2004 | Panescu |
| 2004/0097804 A1 | 5/2004 | Sobe |
| 2004/0097805 A1 | 5/2004 | Verard et al. |
| 2004/0097806 A1 | 5/2004 | Hunter et al. |
| 2004/0116809 A1 | 6/2004 | Chow et al. |
| 2004/0127805 A1 | 7/2004 | MacAdam et al. |
| 2004/0131998 A1 | 7/2004 | Marom et al. |
| 2004/0133111 A1 | 7/2004 | Szczech et al. |
| 2004/0133130 A1 | 7/2004 | Ferry et al. |
| 2004/0135069 A1 | 7/2004 | Odell |
| 2004/0138564 A1 | 7/2004 | Hwang et al. |
| 2004/0138570 A1 | 7/2004 | Nita et al. |
| 2004/0147837 A1 | 7/2004 | Macaulay et al. |
| 2004/0150963 A1 | 8/2004 | Holmberg et al. |
| 2004/0152972 A1 | 8/2004 | Hunter |
| 2004/0155609 A1 | 8/2004 | Lys et al. |
| 2004/0158140 A1 | 8/2004 | Fuimaono et al. |
| 2004/0171924 A1 | 9/2004 | Mire et al. |
| 2004/0176688 A1 | 9/2004 | Haldeman |
| 2004/0186461 A1 | 9/2004 | DiMatteo |
| 2004/0199069 A1 | 10/2004 | Connelly et al. |
| 2004/0210289 A1 | 10/2004 | Wang et al. |
| 2004/0230271 A1 | 11/2004 | Wang et al. |
| 2004/0231065 A1 | 11/2004 | Daniel et al. |
| 2004/0234453 A1 | 11/2004 | Smith |
| 2004/0253365 A1 | 12/2004 | Warren et al. |
| 2004/0254470 A1 | 12/2004 | Drinkwater et al. |
| 2004/0260174 A1 | 12/2004 | Keene |
| 2004/0267086 A1 | 12/2004 | Anstadt et al. |
| 2005/0004450 A1 | 1/2005 | Ben-Haim et al. |
| 2005/0021019 A1 | 1/2005 | Hashimshony et al. |
| 2005/0033150 A1 | 2/2005 | Takahashi et al. |
| 2005/0033177 A1 | 2/2005 | Rogers et al. |
| 2005/0035014 A1 | 2/2005 | Cane |
| 2005/0038355 A1 | 2/2005 | Gellman et al. |
| 2005/0049486 A1 | 3/2005 | Urquhart et al. |
| 2005/0049510 A1 | 3/2005 | Haldeman et al. |
| 2005/0063194 A1 | 3/2005 | Lys et al. |
| 2005/0070788 A1 | 3/2005 | Wilson et al. |
| 2005/0075561 A1 | 4/2005 | Golden |
| 2005/0085716 A1 | 4/2005 | Hamm et al. |
| 2005/0085718 A1 | 4/2005 | Shahidi |
| 2005/0085720 A1 | 4/2005 | Jascob et al. |
| 2005/0101868 A1 | 5/2005 | Ridley et al. |
| 2005/0101869 A1 | 5/2005 | Burba et al. |
| 2005/0105081 A1 | 5/2005 | Odell |
| 2005/0105101 A1 | 5/2005 | Duling et al. |
| 2005/0112135 A1 | 5/2005 | Cormier et al. |
| 2005/0113669 A1 | 5/2005 | Helfer et al. |
| 2005/0113676 A1 | 5/2005 | Weiner et al. |
| 2005/0113700 A1 | 5/2005 | Yanagihara et al. |
| 2005/0113873 A1 | 5/2005 | Weiner et al. |
| 2005/0113874 A1 | 5/2005 | Connelly et al. |
| 2005/0113876 A1 | 5/2005 | Weiner et al. |
| 2005/0131291 A1 | 6/2005 | Floyd et al. |
| 2005/0149002 A1 | 7/2005 | Wang et al. |
| 2005/0151489 A1 | 7/2005 | Lys et al. |
| 2005/0154308 A1 | 7/2005 | Quistgaard et al. |
| 2005/0159644 A1 | 7/2005 | Takano |
| 2005/0159790 A1 | 7/2005 | Shalev |
| 2005/0165301 A1 | 7/2005 | Smith et al. |
| 2005/0165313 A1 | 7/2005 | Byron et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0182295 A1 | 8/2005 | Soper et al. |
| 2005/0203368 A1 | 9/2005 | Verin |
| 2005/0203396 A1 | 9/2005 | Angelsen et al. |
| 2005/0205081 A1 | 9/2005 | Barker et al. |
| 2005/0215901 A1 | 9/2005 | Anderson et al. |
| 2005/0215945 A1 | 9/2005 | Harris et al. |
| 2005/0222532 A1 | 10/2005 | Bertolero et al. |
| 2005/0228281 A1 | 10/2005 | Nefos |

(56) References Cited

U.S. PATENT DOCUMENTS

| | | |
|---|---|---|
| 2005/0240102 A1 | 10/2005 | Rachlin et al. |
| 2005/0256398 A1 | 11/2005 | Hastings et al. |
| 2005/0256541 A1 | 11/2005 | Stypulkowski |
| 2006/0015003 A1 | 1/2006 | Moaddes et al. |
| 2006/0025677 A1 | 2/2006 | Verard et al. |
| 2006/0025684 A1 | 2/2006 | Quistgaard et al. |
| 2006/0058633 A1 | 3/2006 | Hoshino et al. |
| 2006/0068074 A1 | 3/2006 | Stefandl |
| 2006/0084867 A1 | 4/2006 | Tremblay et al. |
| 2006/0116571 A1 | 6/2006 | Maschke et al. |
| 2006/0116578 A1 | 6/2006 | Grunwald et al. |
| 2006/0149134 A1 | 7/2006 | Soper et al. |
| 2006/0173329 A1 | 8/2006 | Irioka et al. |
| 2006/0173407 A1 | 8/2006 | Shaughnessy et al. |
| 2006/0176242 A1 | 8/2006 | Jaramaz et al. |
| 2006/0184074 A1 | 8/2006 | Vaezy et al. |
| 2006/0188487 A1 | 8/2006 | Thomas et al. |
| 2006/0206037 A1 | 9/2006 | Braxton |
| 2006/0211944 A1 | 9/2006 | Mauge et al. |
| 2006/0224188 A1 | 10/2006 | Libbus et al. |
| 2006/0247746 A1 | 11/2006 | Danek et al. |
| 2006/0264756 A1 | 11/2006 | Lo et al. |
| 2006/0276867 A1 | 12/2006 | Viswanathan |
| 2007/0010753 A1 | 1/2007 | MacAdam |
| 2007/0016007 A1 | 1/2007 | Govari et al. |
| 2007/0016013 A1 | 1/2007 | Camus |
| 2007/0016068 A1 | 1/2007 | Grunwald et al. |
| 2007/0016069 A1 | 1/2007 | Grunwald et al. |
| 2007/0016070 A1 | 1/2007 | Grunwald et al. |
| 2007/0016072 A1 | 1/2007 | Grunwald et al. |
| 2007/0049822 A1 | 3/2007 | Bunce et al. |
| 2007/0049846 A1 | 3/2007 | Bown et al. |
| 2007/0055141 A1 | 3/2007 | Kruger et al. |
| 2007/0055142 A1 | 3/2007 | Webler |
| 2007/0060992 A1 | 3/2007 | Pappone |
| 2007/0062544 A1 | 3/2007 | Rauk Bergstrom et al. |
| 2007/0073155 A1 | 3/2007 | Park et al. |
| 2007/0087038 A1 | 4/2007 | Richardson et al. |
| 2007/0093710 A1 | 4/2007 | Maschke |
| 2007/0100285 A1 | 5/2007 | Griffin et al. |
| 2007/0112282 A1 | 5/2007 | Skujins et al. |
| 2007/0123769 A1 | 5/2007 | Fuller et al. |
| 2007/0123805 A1 | 5/2007 | Shireman et al. |
| 2007/0129770 A1 | 6/2007 | Younis |
| 2007/0135803 A1 | 6/2007 | Belson |
| 2007/0135886 A1 | 6/2007 | Maschke |
| 2007/0156205 A1 | 7/2007 | Larson et al. |
| 2007/0161904 A1 | 7/2007 | Urbano |
| 2007/0161915 A1 | 7/2007 | Desai |
| 2007/0167738 A1 | 7/2007 | Timinger et al. |
| 2007/0167801 A1 | 7/2007 | Webler et al. |
| 2007/0167808 A1 | 7/2007 | Nozaki |
| 2007/0167817 A1 | 7/2007 | Huang et al. |
| 2007/0167997 A1 | 7/2007 | Forsberg et al. |
| 2007/0197905 A1 | 8/2007 | Timinger et al. |
| 2007/0208255 A1 | 9/2007 | Ridley et al. |
| 2007/0225589 A1 | 9/2007 | Viswanathan |
| 2007/0225610 A1 | 9/2007 | Mickley et al. |
| 2007/0232882 A1 | 10/2007 | Glossop et al. |
| 2007/0232910 A1 | 10/2007 | Hwang et al. |
| 2007/0238984 A1 | 10/2007 | Maschke et al. |
| 2007/0239018 A1 | 10/2007 | Fetzer et al. |
| 2007/0244413 A1 | 10/2007 | Biggins |
| 2007/0247454 A1 | 10/2007 | Rahn et al. |
| 2007/0249911 A1 | 10/2007 | Simon |
| 2007/0265526 A1 | 11/2007 | Govari et al. |
| 2007/0276241 A1 | 11/2007 | Park et al. |
| 2007/0280974 A1 | 12/2007 | Son et al. |
| 2007/0282196 A1 | 12/2007 | Birk et al. |
| 2007/0282197 A1 | 12/2007 | Bill et al. |
| 2007/0299352 A1 | 12/2007 | Harlev et al. |
| 2008/0008745 A1 | 1/2008 | Stinchcomb et al. |
| 2008/0009720 A1 | 1/2008 | Schefelker et al. |
| 2008/0009743 A1 | 1/2008 | Hayasaka |
| 2008/0015442 A1 | 1/2008 | Watson et al. |
| 2008/0027320 A1 | 1/2008 | Bolorforosh et al. |
| 2008/0045908 A1 | 2/2008 | Gould et al. |
| 2008/0051626 A1 | 2/2008 | Sato et al. |
| 2008/0081958 A1 | 4/2008 | Denison et al. |
| 2008/0082136 A1 | 4/2008 | Gaudiani |
| 2008/0097232 A1 | 4/2008 | Rothenberg |
| 2008/0108949 A1 | 5/2008 | Beasley et al. |
| 2008/0110261 A1 | 5/2008 | Randall et al. |
| 2008/0110263 A1 | 5/2008 | Klessel et al. |
| 2008/0110266 A1 | 5/2008 | Randall et al. |
| 2008/0112265 A1 | 5/2008 | Urbano et al. |
| 2008/0114095 A1 | 5/2008 | Peppmoller et al. |
| 2008/0114239 A1 | 5/2008 | Randall et al. |
| 2008/0114241 A1 | 5/2008 | Randall et al. |
| 2008/0114246 A1 | 5/2008 | Randall et al. |
| 2008/0114247 A1 | 5/2008 | Urbano et al. |
| 2008/0114248 A1 | 5/2008 | Urbano et al. |
| 2008/0114249 A1 | 5/2008 | Randall et al. |
| 2008/0114250 A1 | 5/2008 | Urbano et al. |
| 2008/0114251 A1 | 5/2008 | Weymer et al. |
| 2008/0114252 A1 | 5/2008 | Randall et al. |
| 2008/0114253 A1 | 5/2008 | Randall et al. |
| 2008/0114370 A1 | 5/2008 | Schoenefeld |
| 2008/0119737 A1 | 5/2008 | Urbano et al. |
| 2008/0125772 A1 | 5/2008 | Stone et al. |
| 2008/0139944 A1 | 6/2008 | Weymer et al. |
| 2008/0146939 A1 | 6/2008 | McMorrow et al. |
| 2008/0146940 A1 | 6/2008 | Jenkins et al. |
| 2008/0152204 A1 | 6/2008 | Huo et al. |
| 2008/0154100 A1 | 6/2008 | Thalmeier et al. |
| 2008/0166453 A1 | 7/2008 | Steele et al. |
| 2008/0171934 A1 | 7/2008 | Greenan et al. |
| 2008/0183075 A1 | 7/2008 | Govari et al. |
| 2008/0188747 A1 | 8/2008 | Randall et al. |
| 2008/0188750 A1 | 8/2008 | Randall et al. |
| 2008/0188752 A1 | 8/2008 | Randall et al. |
| 2008/0200754 A1 | 8/2008 | Buchalter |
| 2008/0208060 A1 | 8/2008 | Murkin |
| 2008/0228082 A1 | 9/2008 | Scheirer et al. |
| 2008/0255404 A1 | 10/2008 | Nogawa et al. |
| 2008/0255475 A1 | 10/2008 | Kondrosky et al. |
| 2008/0275765 A1 | 11/2008 | Kuchar |
| 2008/0281206 A1 | 11/2008 | Bartlett et al. |
| 2008/0319311 A1* | 12/2008 | Hamadeh ............... A61B 6/12 600/424 |
| 2009/0005675 A1 | 1/2009 | Grunwald et al. |
| 2009/0018497 A1 | 1/2009 | Birchard et al. |
| 2009/0018574 A1 | 1/2009 | Martin |
| 2009/0024018 A1 | 1/2009 | Boyden et al. |
| 2009/0036774 A1 | 2/2009 | Weng et al. |
| 2009/0036790 A1 | 2/2009 | Landesberg et al. |
| 2009/0043205 A1 | 2/2009 | Pelissier et al. |
| 2009/0076327 A1 | 3/2009 | Ohki |
| 2009/0082661 A1 | 3/2009 | Saladin et al. |
| 2009/0084382 A1 | 4/2009 | Jalde et al. |
| 2009/0101577 A1 | 4/2009 | Fulkerson et al. |
| 2009/0118612 A1 | 5/2009 | Grunwald et al. |
| 2009/0118706 A1 | 5/2009 | Schweikert et al. |
| 2009/0124901 A1 | 5/2009 | Fink et al. |
| 2009/0136099 A1 | 5/2009 | Boyden et al. |
| 2009/0143736 A1 | 6/2009 | Mittermeyer et al. |
| 2009/0149748 A1 | 6/2009 | Lenhardt et al. |
| 2009/0156926 A1 | 6/2009 | Messerly et al. |
| 2009/0163810 A1 | 6/2009 | Kanade et al. |
| 2009/0171217 A1 | 7/2009 | Kim et al. |
| 2009/0171219 A1 | 7/2009 | Uchibori |
| 2009/0177083 A1 | 7/2009 | Matsumura |
| 2009/0177090 A1 | 7/2009 | Grunwald et al. |
| 2009/0177092 A1 | 7/2009 | Riechers et al. |
| 2009/0203989 A1 | 8/2009 | Burnside et al. |
| 2009/0204113 A1 | 8/2009 | MacAdam et al. |
| 2009/0209950 A1 | 8/2009 | Starksen |
| 2009/0227952 A1 | 9/2009 | Blakstvedt et al. |
| 2009/0234328 A1 | 9/2009 | Cox et al. |
| 2009/0258171 A1 | 10/2009 | Uang |
| 2009/0259124 A1 | 10/2009 | Rothenberg |
| 2009/0262982 A1 | 10/2009 | Markowitz et al. |
| 2009/0270722 A1 | 10/2009 | Floyd et al. |
| 2009/0275828 A1 | 11/2009 | Shachar et al. |

(56) References Cited

U.S. PATENT DOCUMENTS

| | | |
|---|---|---|
| 2009/0275833 A1 | 11/2009 | Ikeda et al. |
| 2009/0297441 A1 | 12/2009 | Canham et al. |
| 2010/0004543 A1 | 1/2010 | Ahlund et al. |
| 2010/0004547 A1 | 1/2010 | Scholz et al. |
| 2010/0016726 A1 | 1/2010 | Meier |
| 2010/0036227 A1 | 2/2010 | Cox et al. |
| 2010/0049062 A1 | 2/2010 | Ziv |
| 2010/0055153 A1 | 3/2010 | Majmudar |
| 2010/0055184 A1 | 3/2010 | Zeitels et al. |
| 2010/0057157 A1 | 3/2010 | Govari et al. |
| 2010/0060472 A1 | 3/2010 | Kimura et al. |
| 2010/0083719 A1 | 4/2010 | Peppmoller et al. |
| 2010/0094116 A1 | 4/2010 | Silverstein |
| 2010/0106011 A1 | 4/2010 | Byrd et al. |
| 2010/0114573 A1 | 5/2010 | Huang et al. |
| 2010/0126149 A1 | 5/2010 | Kondou |
| 2010/0143119 A1 | 6/2010 | Kooliman et al. |
| 2010/0179429 A1 | 7/2010 | Ho et al. |
| 2010/0185097 A1 | 7/2010 | Hall |
| 2010/0198048 A1 | 8/2010 | Togawa |
| 2010/0204569 A1 | 8/2010 | Burnside et al. |
| 2010/0217116 A1 | 8/2010 | Eck et al. |
| 2010/0222663 A1 | 9/2010 | Wilder et al. |
| 2010/0222664 A1 | 9/2010 | Lemon et al. |
| 2010/0234733 A1 | 9/2010 | Wahlheim |
| 2010/0249598 A1 | 9/2010 | Smith et al. |
| 2010/0258033 A1 | 10/2010 | Yang et al. |
| 2010/0273895 A1 | 10/2010 | Stinchcomb et al. |
| 2010/0298702 A1 | 11/2010 | Rogers et al. |
| 2010/0312121 A1 | 12/2010 | Guan |
| 2010/0317981 A1 | 12/2010 | Grunwald |
| 2010/0318026 A1 | 12/2010 | Grunwald |
| 2010/0331712 A1 | 12/2010 | Rothenberg |
| 2011/0015527 A1 | 1/2011 | Heasty et al. |
| 2011/0015533 A1 | 1/2011 | Cox et al. |
| 2011/0040186 A1 | 2/2011 | Matsumura |
| 2011/0040187 A1 | 2/2011 | Matsumura |
| 2011/0040212 A1 | 2/2011 | Dietz et al. |
| 2011/0052694 A1 | 3/2011 | Stinchcomb et al. |
| 2011/0060215 A1 | 3/2011 | Tupin, Jr. et al. |
| 2011/0087107 A1 | 4/2011 | Lindekugel et al. |
| 2011/0087117 A1 | 4/2011 | Tremper et al. |
| 2011/0166451 A1 | 7/2011 | Blaivas et al. |
| 2011/0171286 A1 | 7/2011 | Cecile et al. |
| 2011/0196248 A1 | 8/2011 | Grunwald |
| 2011/0202123 A1 | 8/2011 | Bonutti |
| 2011/0278500 A1 | 11/2011 | Bergeron |
| 2011/0282188 A1 | 11/2011 | Burnside et al. |
| 2011/0295108 A1 | 12/2011 | Cox et al. |
| 2011/0313293 A1 | 12/2011 | Lindekugel et al. |
| 2012/0046562 A1 | 2/2012 | Powers et al. |
| 2012/0059270 A1 | 3/2012 | Grunwald |
| 2012/0095319 A1 | 4/2012 | Kondrosky et al. |
| 2012/0108950 A1 | 5/2012 | He et al. |
| 2012/0143029 A1 | 6/2012 | Silverstein et al. |
| 2012/0165679 A1 | 6/2012 | Orome et al. |
| 2012/0220854 A1 | 8/2012 | Messerly et al. |
| 2013/0006102 A1 | 1/2013 | Wilkes et al. |
| 2013/0060116 A1 | 3/2013 | Messerly et al. |
| 2013/0085391 A1 | 4/2013 | Matsumura et al. |
| 2013/0116571 A1 | 5/2013 | Cox et al. |
| 2013/0123597 A1 | 5/2013 | Rothenberg |
| 2013/0131704 A1 | 5/2013 | Pechoux |
| 2013/0245488 A1 | 9/2013 | Quinn et al. |
| 2013/0338503 A1 | 12/2013 | Cohen et al. |
| 2014/0180116 A1 | 6/2014 | Lindekugel et al. |
| 2015/0314104 A1 | 11/2015 | Almansouri et al. |
| 2020/0138409 A1 | 5/2020 | Lindekugel et al. |

FOREIGN PATENT DOCUMENTS

| | | |
|---|---|---|
| AU | 20009592 | 9/2000 |
| AU | 20015250 | 6/2001 |
| AU | 768362 B2 | 12/2003 |
| AU | 2001229024 B2 | 9/2005 |
| AU | 2001283703 B2 | 5/2006 |
| AU | 2006202149 | 6/2006 |
| AU | 2006904933 | 9/2006 |
| AU | 2006283022 B2 | 2/2012 |
| CA | 2420676 | 2/2002 |
| CN | 1175196 A | 3/1998 |
| CN | 1672649 A | 9/2005 |
| CN | 101390754 A | 3/2009 |
| CN | 102014757 A | 4/2011 |
| CN | 102209490 A | 10/2011 |
| CN | 102802514 A | 11/2012 |
| CN | 102821679 A | 12/2012 |
| CN | 103037761 A | 4/2013 |
| CN | 103037762 A | 4/2013 |
| CN | 103118591 A | 5/2013 |
| CN | 103228219 A | 7/2013 |
| DE | 4319033 C1 | 6/1994 |
| DE | 9404028 U1 | 8/1994 |
| EP | 0359697 | 3/1990 |
| EP | 0362821 | 4/1990 |
| EP | 0399536 A1 | 11/1990 |
| EP | 0815793 A2 | 1/1998 |
| EP | 0823261 A2 | 2/1998 |
| EP | 0928976 A2 | 7/1999 |
| EP | 1311226 A1 | 5/2003 |
| EP | 1504713 A1 | 2/2005 |
| EP | 2313143 A1 | 4/2011 |
| EP | 2440122 A1 | 4/2012 |
| EP | 2464407 A2 | 6/2012 |
| EP | 2482719 A1 | 8/2012 |
| EP | 2575610 A1 | 4/2013 |
| EP | 2575611 A1 | 4/2013 |
| EP | 2603145 A2 | 6/2013 |
| EP | 2605699 A2 | 6/2013 |
| FR | 2545349 | 11/1984 |
| JP | 01097440 | 4/1989 |
| JP | H02 13439 A | 1/1990 |
| JP | 03023853 A | 1/1991 |
| JP | 03173542 A | 7/1991 |
| JP | 4090741 | 8/1992 |
| JP | 9-503054 | 3/1997 |
| JP | 09-094298 A | 4/1997 |
| JP | 10043310 | 2/1998 |
| JP | 10290839 A | 11/1998 |
| JP | 11128237 A | 5/1999 |
| JP | 2001161683 | 6/2001 |
| JP | 2001340334 | 12/2001 |
| JP | 2003501127 A | 1/2003 |
| JP | 2003061752 A | 3/2003 |
| JP | 2003299654 | 10/2003 |
| JP | 2003334191 | 11/2003 |
| JP | 2002520893 | 2/2004 |
| JP | 2004505748 T | 2/2004 |
| JP | 2004515298 A | 5/2004 |
| JP | 2004 313271 A | 11/2004 |
| JP | 2006508744 A | 3/2006 |
| JP | 5010604 | 6/2012 |
| JP | 2012-529929 | 11/2012 |
| JP | 2013-518676 A | 5/2013 |
| JP | 2013-535301 A | 9/2013 |
| WO | 1991012836 A1 | 9/1991 |
| WO | 1992003090 | 3/1992 |
| WO | 1994003159 A1 | 2/1994 |
| WO | 1994004938 | 3/1994 |
| WO | 1996005768 A1 | 2/1996 |
| WO | 1996007352 A1 | 3/1996 |
| WO | 1996041119 | 12/1996 |
| WO | 1997029683 A1 | 8/1997 |
| WO | 1997043989 A1 | 11/1997 |
| WO | 1999016495 A1 | 4/1999 |
| WO | 1999049407 A1 | 9/1999 |
| WO | 2000019906 | 4/2000 |
| WO | 2000040155 | 7/2000 |
| WO | 2000074775 A1 | 12/2000 |
| WO | 2001076479 A1 | 10/2001 |
| WO | 2002015973 A1 | 2/2002 |
| WO | 2002025277 A1 | 3/2002 |
| WO | 2003061752 | 7/2003 |
| WO | 2003077759 A1 | 9/2003 |

(56) References Cited

FOREIGN PATENT DOCUMENTS

| | | |
|---|---|---|
| WO | 2004049970 A2 | 6/2004 |
| WO | 2005033524 A1 | 4/2005 |
| WO | 2005033574 A1 | 4/2005 |
| WO | 2005117690 A1 | 12/2005 |
| WO | 2006074509 A1 | 7/2006 |
| WO | 2006074510 A1 | 7/2006 |
| WO | 2006078677 A2 | 7/2006 |
| WO | 2006103661 A2 | 10/2006 |
| WO | 2006111056 A1 | 10/2006 |
| WO | 2007002541 A2 | 1/2007 |
| WO | 2007005976 A1 | 1/2007 |
| WO | 2007014447 A1 | 2/2007 |
| WO | 2007034196 A2 | 3/2007 |
| WO | 2007067324 A1 | 6/2007 |
| WO | 2007069168 A2 | 6/2007 |
| WO | 2007109123 A2 | 9/2007 |
| WO | 2007126536 A2 | 11/2007 |
| WO | 2007144894 A1 | 12/2007 |
| WO | 2008005480 A1 | 1/2008 |
| WO | 2008/024515 A2 | 2/2008 |
| WO | 2008024596 A2 | 2/2008 |
| WO | 2008028253 | 3/2008 |
| WO | 2008083111 | 7/2008 |
| WO | 2008118992 A1 | 10/2008 |
| WO | 2008126074 A2 | 10/2008 |
| WO | 2008131017 A2 | 10/2008 |
| WO | 2008136008 A2 | 11/2008 |
| WO | 2009002514 A2 | 12/2008 |
| WO | 2009009064 A1 | 1/2009 |
| WO | 2009057774 A1 | 5/2009 |
| WO | 2009070616 A2 | 6/2009 |
| WO | 2009100158 A1 | 8/2009 |
| WO | 2009123819 A2 | 10/2009 |
| WO | 2009126340 A1 | 10/2009 |
| WO | 2009129475 A1 | 10/2009 |
| WO | 2009129477 A1 | 10/2009 |
| WO | 2009134605 A2 | 11/2009 |
| WO | 2009137262 A2 | 11/2009 |
| WO | 2010002313 A1 | 1/2010 |
| WO | 2010018500 A1 | 2/2010 |
| WO | 2010022370 A1 | 2/2010 |
| WO | 2010027349 A1 | 3/2010 |
| WO | 2010027471 A2 | 3/2010 |
| WO | 2010030820 A1 | 3/2010 |
| WO | 2010132857 A1 | 11/2010 |
| WO | 2010143196 A1 | 12/2010 |
| WO | 2010144922 A1 | 12/2010 |
| WO | 2011019760 A2 | 2/2011 |
| WO | 2011041450 A1 | 4/2011 |
| WO | 2011044421 A1 | 4/2011 |
| WO | 2011051406 A1 | 5/2011 |
| WO | 2011064209 A1 | 6/2011 |
| WO | 2011084593 A2 | 7/2011 |
| WO | 2011097312 A1 | 8/2011 |
| WO | 2011128052 A2 | 10/2011 |
| WO | 2011150358 A1 | 12/2011 |
| WO | 2012021542 A2 | 2/2012 |
| WO | 2012024577 A2 | 2/2012 |
| WO | 2012058461 A1 | 5/2012 |
| WO | 2012060562 A2 | 5/2012 |
| WO | 2012083245 A1 | 6/2012 |
| WO | 2012088535 A1 | 6/2012 |
| WO | 2013006817 A1 | 1/2013 |
| WO | 2013070775 A1 | 5/2013 |
| WO | 2013188833 A2 | 12/2013 |
| WO | 2014134171 A1 | 9/2014 |

OTHER PUBLICATIONS

Engelhardt, W et al, ECG-Controlled Placement of Central Venous Catheters in Patients with Atrial Fibrillation, Anaesthesist, pp. 476-479, vol. 38 No. 9, Sep. 1989 (Abstract only).

Fearon, William F et al, Evaluating Intermediate Coronary Lesions in the Cardiac Catheterization Laboratory, vol. 4, No. 1, 7 pages, Reviews in Cardiovascular Medicine, 2003.

Felleiter P et al, Use of Electrocardiographic Placement Control of Central Venous Catheters in Austria, Acta Med Austriaca, pp. 109-113, vol. 26 No. 3, 1999 (Abstract only).

Forauer, AR et al, Change in Peripherally Inserted Central Catheter Tip Location with Abduction and Adduction of the Upper Extremity, J Vasc Interv Radiol, pp. 1315-1318, vol. 11 No. 10, Nov.-Dec. 2000.

Frassinelli, P et al, Utility of Chest Radiographs after Guidewire Exchanges of Central Venous Catheters, Crit Care Med, pp. 611-615, vol. 26 No. 3, Mar. 1998.

Frazin L et al, A Doppler Guided Retrograde Catheterization System, Cathet. Cardiovasc Diagn, pp. 41-50, May 1992.

French, PJ et al, Sensors for Catheter Applications, Sensors Update, vol. 13 Issue 1 pp. 107-153, Dec. 2003.

Gebauer, B et al, Ultrasound and Fluoroscopy-guided Implantation of Peripherally Inserted Central Venous Catheters (PICCs), ROFO, pp. 386-391, vol. 176 No. 3, Mar. 2004 (Abstract only).

Gebhard, et al., "The accuracy of Electrocardiogram-Controlled Central Line Placement." The International Anesthesia Research Society, vol. 104, No. 1 Jan. 2007.

Gjendemsjo, Anders, et al., Energy and Power, The Connexions Project, Version 1.2, Feb. 20, 2004.

Gladwin, MT et al, Cannulation of the Internal Jugular Vein: is postpocedural chest radiography always necessary?, Crit Care Med, 33 pages, Oct. 2000.

Gonzales, et al. "Peripherally Inserted Central Catheter Placement in Swine Using Magnet Detection." Journal of Intravenous Nursing, vol. 22, No. 3, May/Jun. 1999.

Greenall, M.J. et al, Cardiac Tamponade and Central Venous Catheters, British Medical Journal, pp. 595-597, Jun. 14, 1975.

Guillory, "Basic Principles of Technologies for Catheter Localization." C.R. Bard internal paper, Oct. 20, 2004.

Guth, AA, Routine Chest X-rays after Insertion of Implantable Long-Term Venous Catheters: Necessary or Not?, Am Surg, pp. 26-29, vol. 67 No. 1, Jan. 2001 (Abstract only).

Hill, Bradley et al, Abstract of article discussing Vasallova VPS as guide for placement of PICCs. 2009.

Hill, Bradley, Identifying the Caval-Atrial Junction Using Smart-Catheter Technology presentation, 22nd Annual Scientific Meeting of the AVA in Savannah, Georgia, Sep. 13, 2008.

Hoffman, Thomas et al, Simultaneous Measurement of Pulmonary Venous Flow by Intravascular Catheter Doppler Velocimetry and Transesophageal Doppler Echocardiography: Relation to Left Atrial Pressure and Left Atrial and Left Ventricular Function, pp. 239-249, J Am Coll Cardiol, Jul. 1995.

Hoffmann, et al. "New Procedure in Transesophageal Echocardiography: Multiplane Transesophageal Echocardiography and Transesophageal Stress Echocardiography." Herz, vol. 18, No. 5, pp. 269-277, Oct. 1993.

Iacopino, Domenico Gerardo et al, Intraoperative Microvascular Doppler Monitoring of Blood Flow within a Spinal Dural Arteriovenous Fistula: A Precious Surgical Tool, vol. 10, 5 pages, Neurosurg. Focus, Feb. 2001.

Joosting, Jean-Pierre, "Dual-interface RFID-compatible EEPROM enables remote access to electronic device parameters," EE Times, Mar. 8, 2010.

Kim, Ko et al, Positioning Internal Jugular Venous Catheters using the Right Third Intercostal Space in Children, Acta Anaesthesiol Scand, pp. 1284-1286, vol. 47 No. 10, Nov. 2003.

Kjelstrup T et al, Positioning of Central Venous Catheters using ECG, Tidssk Nor Laegeforen, pp. 599-601, vol. 111 No. 5, Feb. 1999 (Abstract only).

Kofler, Julia, et al., Epinephrine application via an endotracheal airway and via the Combitube in esophageal position, Critical Care Medicine: May 2000, vol. 28: Issue 5, pp. 1445-1449.

Konings, MK, et al., Development of an intravascular impedance catheter for detection of fatty lesions in arteries, IEEE Trans Med Imaging Aug. 1997; 16(4):439-46.

(56) References Cited

OTHER PUBLICATIONS

Kowalski, CM et al, Migration of Central Venous Catheters: Implications for Initial Catheter Tip Positioning, J Vasc Interv Radiol, pp. 443-447, vol. 8 No. 3, May-Jun. 1997.
Leowenthal, MR et al, The Peripherally Inserted Central Catheter (PICC): A Prospective Study of its Natural History after Fossa Insertion, Anaesth Intensive Care, pp. 21-24; vol. 30 No. 1, Feb. 2002.
Lepage Ronan et al. ECG Segmentation and P-wave Feature Extraction: Application to Patients Prone to Atrial Fibrillation, IEEE/EMBS Proceedings, 23rd Annual Conference, Istanbul, Turkey, Oct. 25-28, 2001.
Liu , Ji-Bin et al, Catheter-Based Intraluminceal Sonography, J Ultrasound Med, pp. 145-160, vol. 23, 2004.
Lucey, B et al, Routine Chest Radiographs after Central Line Insertion: Mandatory Postprocedural Evaluation or Unnecessary Waste of Resources?, Cardiovasc Intervent Radiol, pp. 381-384, vol. 22 No. 5, Sep.-Oct. 1999.
Lum, Phillip, A New Formula-Based Measurement Guide for Optimal Positioning of Central Venous Catheters, JAVA, vol. 9, No. 2, pp. 80-85, 2004.
Lynch, RE et al, A Procedure for Placing Pediatric Femoral Venous Catheter Tips near the Right Atrium, Pediatr Emerg Care, pp. 130-132, vol. 18 No. 2, Apr. 2002.
Madan, et al. "Right Atrial Electrocardiography: A Technique for the Placement of Central Venous Catheters for Chemotherapy or Intravenous Nutrition." British Journal of Surgery, vol. B1, pp. 1604-1605, 1994.
Madias, John E, Intracardiac (Superior Vena Cava/Right Atrial) ECGs using Saline Solution as the Conductive Medium for the Proper Positioning of the Shiley Hemodialysis Catheter: Is it Not Time to Forego the Postinsertion Chest Radiograph?, pp. 2363-2367, Chest, 2003.
Markovich, Mary B., Central Venous Catheter Tip Placement: Determination of Posterior Malposition—A Case Study, JAVA, vol. 11, No. 2, pp. 85-89, 2006.
Martin, Roy W, An Ultrasoundic Catheter for Intravascular Measurement of Blood Flow: Technical Details, IEEE Transactions on Sonics and Ultrasonics, vol. SU-27, No. 6, pp. 277-286, Nov. 1980.
McDonnall, "Intra-Atrial Electrocardiography (ECG) for Catheter Placement." Literature review prepared for Bard Access Systems, Oct. 2007.
McGee et al., "Accurate Placement of Central Venous Catheters: A Prospective, Randomize, Multicenter Trail." Critical Care Medicine, vol. 21 No. 8, Aug. 1993.
MedGraphics, CardioPerfect® Resting/Stress ECG System, 3 pages, 2001.
Michenfelder, John et al, Air Embolism During Neurosurgery—An Evaluation of Right-Atrial Catheters for Diagnosis and Treatment, JAMA, pp. 1353-1358, vol. 208, No. 8, May 26, 1969.
Michenfelder, John et al, Air Embolism During Neurosurgery. A New Method of Treatment, Anesthesia and Analgesia. Current Researches, pp. 390-395, vol. 45, No. 4, Jul.-Aug. 1966.
MICROBIRD™ Miniaturized DC Magnetic Sensors for Intra-body Navigation and Localization, Specifications, 2005.
MICRONIX CathRite™ Cardiac Access Device Brochure. Jun. 2004.
Micronix Pty Ltd "CathRite" Guiding Styled Core Manufacturing, Jun. 15, 2006.
Murthy, Vrudhula et al, Analysis of Power Spectral Densities of Electrocardiograms, Mathematical Biosciences, pp. 41-51, vol. 12 No. 1-2, Oct. 1971.
Nadroo, AM et al, Changes in Upper Extremity Position Cause Migration of Peripherally Inserted Central Catheters in Neonates, Pediatrics, pp. 131-136, vol. 110, Jul. 2002.
Nakatani, K et al, Accurate Placement of Central Venous Catheters—ECG-guided method vs Patient Height Method, MASUI, pp. 34-38, vol. 51 No. 1, Jan. 2002.
Nazarian, GK et al, Changes in Tunneled Catheter Tip Position when a patient is Upright, J Vasc Intery Radiol, pp. 437-441, vol. 8 No. 3, May-Jun. 1997.
NEUROMETER® CPT, Clinical Applications. Neurotron , Inc. website: www.neurotron.com/CLINAPS.html, last accessed Oct. 23, 2006.
The FloWire Doppler Guide Wire located <http://www.volcanocorp.com/products/flowire-doppler-guide-wire.php>, 2011.
TRAXAL Technologies, Tracking Technology website overview: www.traxal.com/rd/rd_classroom_trackingtechnology.htm, last accessed Dec. 1, 2006.
UAB Health Systems, Arrhythmias, retrieved from http://www.health,uab.edu/14564/ on Nov. 15, 2007, 12 pages.
U.S. Appl. No. 12/900,750, filed Oct. 8, 2010 Final Office Action dated Dec. 3, 2013.
U.S. Appl. No. 12/900,750, filed Oct. 8, 2010 Non-Final Office Action dated Apr. 10, 2014.
U.S. Appl. No. 12/900,750, filed Oct. 8, 2010 Non-Final Office Action dated Jun. 3, 2013.
U.S. Appl. No. 13/206,396, filed Aug. 9, 2011 Non-Final Office Action dated Feb. 27, 2014.
U.S. Appl. No. 13/671,382, filed Nov. 7, 2012 Non-Final Office Action dated Mar. 10, 2014.
U.S. Appl. No. 29/428,649, filed Aug. 1, 2012 Notice of Allowance dated Jul. 5, 2013.
Valdivieso, J.R. Perez, et al., Evaluation of a formula for optimal positioning of a central venous catheter inserted through the right internal jugular vein, Rev. Esp. Anestesiol. Reanim. 2003; 50: 77-79.
VasoNova Inc, Vascular navigation system for accurate placement of PICCs, Start-Up Emerging Medical Ventures, pp. 44-45, vol. 14 No. 7, Jul.-Aug. 2009.
Vesely, Thomas M. et al., Central Venous Catheter Tip Position: A Continuing Controversy, J Vasc Intery Radiol 2003; 14:527-534.
VIASYS Health Care Inc. Cortrak © Fact Sheet, 2005.
VIASYS Healthcare MedSystems, Navigator® Benefits, 2008.
VIASYS Healthcare MedSystems, Navigator® Research in Cost Justification, 2008.
VIASYS MedSystems, Cortrak™ Systems Brochure, 2005.
Volcano ComboMap Features and Benefits/Technical Specifications, 2 pages, 2011.
Watters, et al. "Use of Electrocardiogram to Position Right Atrial Catheters During Surgery." Annals of Surgery, vol. 225, No. 2, pp. 165-171, 1997.
Welch Allyn Cardioperfect® PC-Based Resting ECG, 2003.
Wilson, R. G. et al, Right Atrial Electrocardiography in Placement of Central Venous Catheters, The Lancet, pp. 462-463, Feb. 27, 1988.
Wong, Jeffrey J. et al., Azygos Tip Placement for Hemodialysis Catheters in Patients with Superior Vena Cava Occlusion, Cardiovasc Intervent Radiol (2006) 29:143-146.
Worley, Seth J. "Use of a Real-Time Three-Dimensional Magenetic Navigation System for Radiofrequency Ablation of Accessory Pathways." PACE, vol. 21 pp. 1636-1643, Aug. 1998.
Yilmazlar A et al, Complications of 1303 Central Venous Cannulations, J R Soc Med, pp. 319-321, vol. 90 No. 6, Jun. 1997 (Abstract only).
Yoon, SZ et al, Usefulness of the Carina as a Radiographic Landmark for Central Venous Catheter Placement in Paediatric Patients, Br J Anaesth, Jul. 2005.
Yoshida, Teruhisa et al, Detection of Concealed Left Sided Accessory Atrioventricular Pathway by P Wave Signal Averaged Electrocardiogram, J Am Coll Cardiol, pp. 55-62, 1999.
Zaaroor, et al. "Novel Magnetic Technology for Intraoperative Intracranial Frameless Navigation: In Vivo and in Vitro Results." Neurosurgery, vol. 48, No. 5. pp. 1100-1107, May 2001.
Zachariou, Zacharias et al., Intra-atrial ECG recording: a new and safe method for implantation of Broviac catheters in children, Pediatr Surg Int (1994) 9: 457-458.
CN 201180048882.3 filed Apr. 9, 2013 First Office Action dated Jun. 30, 2014.
CN 201180048882.3 filed Apr. 9, 2013 Second Office Action dated Mar. 18, 2015.

(56) References Cited

OTHER PUBLICATIONS

JP 2013-524183 filed Feb. 8, 2015 First Office Action dated Jun. 24, 2015.
U.S. Appl. No. 12/900,750, filed Oct. 8, 2010 Final Office Action dated Sep. 4, 2014.
U.S. Appl. No. 12/900,750, filed Oct. 8, 2010 Non-Final Office Action dated Jan. 30, 2015.
U.S. Appl. No. 13/206,396, filed Aug. 9, 2011 Final Office Action dated Jul. 31, 2014.
U.S. Appl. No. 13/206,396, filed Aug. 9, 2011 Non-Final Office Action dated Dec. 16, 2014.
U.S. Appl. No. 13/206,396, filed Aug. 9, 2011, Final Office Action dated Jun. 10, 2015.
U.S. Appl. No. 13/671,382, filed Nov. 7, 2012 Advisory Action dated May 27, 2015.
U.S. Appl. No. 13/671,382, filed Nov. 7, 2012 Final Office Action dated Mar. 12, 2015.
U.S. Appl. No. 13/671,382, filed Nov. 7, 2012 Final Office Action dated Sep. 23, 2014.
NEUROMETER® CPT, Frequently Asked Questions. Neurotron, Inc. website: www.neurotron.com/CPTFAQ/html, last accessed Oct. 23, 2006.
NEUROMETER® CPT, Products Page. Neurotron, Inc. website: www.neurotron.com/products.html, last accessed Oct. 23, 2006.
NEUROMETER® Electrodiagnostic Neuroselective Sensory Nerve Evaluation: Charts, Tables, Documents & Downloads. Neurotron, Inc. website: www.neurotron.com/downloads.html, last accessed Oct. 23, 2006.
Odd, De et al, Does Radio-opaque Contrast Improve Radiographic localisation of Percutaneous Central Venous Lines?, Arch Dis Child Fetal Neonatal Ed, pp. 41-43, vol. 89 No. 1, Jan. 2004.
Palesty, JA et al, Routine Chest Radiographs Following Central Venous Recatherization over a Wire are not Justified, Am J Surg, pp. 618-621, vol. 176 No. 6, Dec. 1998.
Paliotti, Roberta P. et al, Intravascular Doppler Technique for Monitoring Renal Venous Blood Flow in Man, J Nephrol, pp. 57-62, 2003.
Parker, K.H. et al, Cardiovascular Fluid Dynamics, Department of Bioengineering, National Heart and Lung Institute, Imperial College of Science, Technology and Medicine, Cardiovascular Haemodynamics, pp. 1-28, Sep. 26, 2005.
Pawlik, et al., "Central Venous Catheter Placement: Comparison of the Intravascular Guidewire and the Fluid Column Electrocardiograms." European Journal of Anaesthesiology, vol. 41, pp. 594-599, 2004.
PCT/US2010/051917 filed Oct. 8, 2010 Search Report dated Nov. 29, 2010.
PCT/US2010/051917 filed Oct. 8, 2010 Written Opinion dated Nov. 29, 2010.
PCT/US2011/047127 filed Aug. 9, 2011 International Preliminary Report on Patentability dated Apr. 18, 2013.
PCT/US2011/047127 filed Aug. 9, 2011 International Search Report dated Feb. 29, 2012.
PCT/US2011/047127 filed Aug. 9, 2011 Written Opinion dated Feb. 29, 2012.
PCT/US2012/063956 filed Nov. 7, 2012 International Seach Report and Written Opinion dated Apr. 1, 2013.
PCT/US2013/045999 filed Jun. 14, 2013 International Search Report and Written Opinion dated Nov. 21, 2013.
PCT/US2014/018681 filed Feb. 26, 2014 International Search Report and Written Opinion dated May 19, 2014.
Pennington, C.R., Right Atrial Thrombus: a Complication of Total Parenteral Nutrition, British Medical Journal, pp. 446-447, vol. 295, Aug. 15, 1987.
Petersen, J et al, Silicone Venous Access Devices Positioned with their Tip High in the Superior Vena Cava are More Likely to Malfunction, Am J Surg, pp. 38-41, vol. 178 No. 1, Jul. 1999.
Pittiruti, et al, Intracavitary EKG Monitoring: A reliable method for controlling tip position during and after PICC Insertion presentation in Catholic University, Rome, Italy in 2008.
Pittiruti, et al. "The EKG Method for Positioning the Tip of PICCs: Results from Two Preliminary Studies." JAVA, vol. 13, No. 4, pp. 179-185, 2008.
Polos, PG et al, Tips for Monitoring the Position of a Central Venous Catheter—How Placement can go awry—even when the anatomy is normal, J Crit Illn, pp. 660-674, vol. 8 No. 6, Jun. 1993 (Abstract only).
Pop, Gheorghe A. et al., Catheter-based impedance measurements in the right atrium for continuously monitoring hematocrit and estimating blood viscosity changes; an in vivo feasibility study in swine, Biosensors and Bioelectronics 19 (2004) 1685-1693.
Popp, M. B. et al., Accuracy of implanted port placement with the use of the electromagnetic CathTracke® catheter locator system, The Journal of Vascular Access 2005; 6: 9-12.
Randolph AG et al, Ultrasound guidance for placement of central venous catheters: a meta-analysis of the literature, Critcal Care Medicine, pp. 2053-2058, vol. 24, Dec. 1996.
Reece, A et al, Posititioning Long Lines: Contrast Versus Plain Radiography, Arch Dis Child Fetal Neonatal Ed, pp. 129-130, vol. 84 No. 2, Mar. 2001.
Reynolds, N et al, Assessment of Distal Tip Position of Long Term Central Venous Feeding Catheters using Transesophageal Echocardiology, JPEN J Parenter Enteral Nutr, pp. 39-41, vol. 25 No. 1, Jan.-Feb. 2001.
Ruschulte, Heiner et al, Prevention of Central Venous Catheter related infections with chlorhex idine gluconate impregnated wound dressings: A randomized controlled trial, presented as an abstract at the Annual meeting of the European Society of Anaesthesiologists (ESA) in Madrid, Spain in Jun. 2006, 12 pages, Annals of Hematology, Jul. 14, 2008.
Rutala, Guideline for Disinfection and Sterilization in Healthcare Facilities, 2008.
Rutherford, J. S. et al., Depth of Central Venous Catheterization: An Audit of Practice in a Cardiac Surgical Unit, Anaesth Intens Care 1994; 22: 267-271.
Sacolick, et al. "Electromagnetically Tracked Placement of a Peripherally Inserted Central Catheter." SPIE Medical Imaging, 2004 Proceedings.
Salem, et al. "A New Peripherally Implanted Subcutaneous Permanent Central Venous Access Device for Patients Requiring Chemotherapy." Journal of Clinical Oncology, vol. 11, No. 11, pp. 2181-2185, Nov. 1993.
Savary, D et al, Intra-atrial Monitoring to Add Insertion of a Central Venous Line in Pre-Hospital Emergency Care Journal Europeen des Urgences, pp. 75-78, vol. 17 No. 2, 2004.
Schafer et al. "Incorrect placement of a vena cava catheter and its prevention by intra-atrial ECG." Anaesthesist. Jan. 1988;37(1):49-51.
Schummer, et al. "Central Venous Catheters—The inability of 'intra-atrial ECG' to prove adequate positioning." British Journal of Anaesthesia, vol. 93, No. 2, pp. 193-198, 2004.
Schummer, W et al, ECG-guided Central Venous Catheter Positioning: Does it detect the Pericardial Reflection rather than the Right Atrium?, Eur J Anaesthesiol, pp. 600-605, vol. 21 No. 8, Aug. 2004 (Abstract only).
Schummer, W et al, Intra-Atrial ECG is not a Reliable Method for Positioning Left Internal Jugular Vein Catheters, Br J Anaesth, pp. 481-486, vol. 91 No. 4, Oct. 2003.
Schummer, W, Central Venous Catheter—the Inability of "Intra-Atrial ECG" to prove Adequate Positioning, Br J Anaesth, pp. 193-198, vol. 93 No. 2, Aug. 2004.
Schuster, M. et al., The carina as a landmark in central venous catheter placement, British Journal of Anaesthesia 85 (2): 192-4 (2000).
Siela, Debra, Using Chest Radiography in the Intensive Care Unit, Crit Care Nurse Aug. 1, 2002 vol. 22 No. 4, pp. 18-27.
Silindir, M. et al., "Sterilization Methods and the Comparison of E-Beam Sterilization with Gamma Radiation Sterilization," FABAD J. Pharm. Sci., 34, 43-53, 2009.
Simon, et al., "Central Venous Catheter Placement in Children: Evaluation of Electrocardiography Using J-Wire." Paediatric Anaesthesia vol. 9, pp. 501-504, 1999.

(56) References Cited

OTHER PUBLICATIONS

Smith, Brigham, et al., Intravenous electrocardiographic guidance for placement of peripherally inserted central catheters, Journal of Electrocardiology 43 (2010) 274-278.
Stark, DD et al, Radiographic Assessment of Venous Catheter Position in Children: Value of the Lateral View, Pediatric Radiology, pp. 76-80, vol. 14 No. 2, 1984.
Starkhammar et al. "Cath-Finder Catheter Tracking System: A New Device for Positioning of Central Venous Catheters. Early Experience from Implantation of Brachial portal Systems." Acta Anaesthesiol Scandinavia, vol. 34, No. 4 pp. 296-300, May 1990.
Starkhammer, H et al, Central Venous Catheter Placement using Electromagnetic Position Sensing: A Clinical Evaluation, Biomed. Instrum Technol, vol. 30 No. 2, pp. 164-170; Mar.-Apr. 1996.
Starr, David S et al, EKG Guided Placement of Subclavian CVP Catheters Using J-Wire, pp. 673-676, Ann. Surg, Dec. 1986.
Stas, M et al, Peroperative Intravasal Electrographic Control of Catheter Tip Position in Access Ports Placed by Venous Cut-Down Technique, EJSO, pp. 316-320, vol. 27, 2001.
Stereotaxis Magetic Navigation System with Navigant™ User Interface, 2005 Brochure.
Stereotaxis, Expanding the Possibilites of Interventional Medicine: Remote Navigation and Automation, pp. 1-8, Apr. 2011.
TEPA® Health Innovation PC based ECG System Introduction and Technical Specifications, EKG Master USB, 2 pages, Nov. 2003.
Butler et al. "Practical Considerations for Analog Operation of Bucket-Brigade Circuits" IEEE Journal of Solid-State Circuits, vol. SC-8, No. 2, Apr. 1973.
CN 201180048882.3 filed Apr. 9, 2013 Third Office Action dated Aug. 19, 2014.
Freeman et al. "Delta-Sigma Oversampled Ultrasound Beamformer with Dynamic Delays" IEEE Transactions on Ultrasonics, Ferroelectrics, and Frequency control, vol. 46, No. 2,—Mar. 1999.
Mo et al. "Front-End Processor Using BBD Distributed Delay-Sum Architecture for Micromachined Ultrasonic Sensor Array" Journal of Microelectromechanical Systems, vol. 12, No. 4, Aug. 2003.
Mo et al. "Integrated analog beam former based on bucket brigade device for micromachined ultrasonic sensor array" Sensors and Actuators A 101 (2002) 203-211—Apr. 22, 2012.
Mo et al. "Pipelined Delay-Sum Architecture Based on Bucket-Brigade Devices for On-Chip Ultrasound Beamforming" IEEE Journal of Solid-State Circuits, vol. 38, No. 10, Oct. 2003.
Mucci, R. A. "A Comparison of Efficient Beamforming Algorithms" IEEE Transactions on Acoustics, Speech, and Signal Processing, vol. ASSP-32, No. 3,—Jun. 1984.
Savord et al. "Fully Sampled Matrix Transducer for Real Time 3D Ultrasonic Imaging" IEEE Ultrasonics Symposium-945—2003.
Tanaka el al. "Development of BBD Adding-Delay Architecture for Utrasonic Micro Array Sensor" IEEJ Trans. SM, vol. 125, No. 4 2005.
Thomenius "Evolution of Ultrasound Beamformers" IEEE Ultrasonics Symposium 1996.
"Ascension to Launch New 3D Guidance™ Tracker at TCT 2006." Press Releases from Ascension website: www.ascension-tech.com/news/press_101106.php, last accessed Dec. 1, 2006.
Acuson—The Value of Vision, AcuNav Diagnostic Ultrasound Catheter, 2000.
Advertising flyer for GAVECELT—The Italian Group for Long Term Venous Access Devices, for program on International Meeting on PICC's, Midline Catheters and Long Term Venous Access Devices in Catholic University, Rome, Italy on Dec. 3, 4, 5, 2008.
Alexander, GD et al, The Role of Nitrous Oxide in Postoperative Nausea and Vomiting, Collection of Abstracts Presented at the International Anesthesia Research Society by various speakers, 58th Congress, Mar. 12-14, 1984, Anesthesia and Analgesia, pp. 175-284, vol. 63, 1984.
Allan, P.L. et al, Role of Ultrsound in the Assessment of Chronic Venous Insufficiency, Ultrasound Quarterly, vol. 17, No. 1, pp. 3-10, 2001.

Andropoulos, et al. "A Controlled Study of the Transesophageal Echocardiography to Guide Central Venous Catheter Placement in Congetital Heart Surgery Patients." The International Anesthesia Research Society, vol. 89, pp. 65-70, 1999.
Anonymous author, Correct Catheter Placement with a low-impact, reliable and economical method, <http://www.cvc-partner.com/index.cfm?103A955CC6844BF58ACFE3C9C1471959>, last accessed Dec. 22, 2011.
Arai, J et al, Detection of Peripherally Inserted Central Catheter Occlusion by in-line Pressure Monitoring, Paediatr Anaesth, pp. 621-624, vol. 12 No. 7, Sep. 2002.
Arrow International, Inc., The Arrow-Johans RAECG Adapter-Making Proper Central Venous Catheter Placement More Reliable (Modle No. EG-04900), Technical Report 1987, USA.
Aslamy, et al. "MRI of Central Venous Anatomy: Implications for Central Venous Catheter Insertion." American College of Chest Physicians, Jun. 8, 2009.
AU 2011289513 filed Jan. 21, 2013 Examiner's Report dated Jul. 5, 2013.
AURORA® System Technical Specifications, Oct. 2003.
B. Braun Website, "The Optimal Position of the Central Venous Catheter." http://www.cvcpartner.com/index.cfm18F1BDEA1310466194960A39F4E90968 (2009).
B. Braun, Certofix Central Venous Catheter for Placement Using the Seldinger Technique with Simultaneous ECG Lead Option, Feb. 2010.
Bailey, SH et al, Is Immediate Chest Radiograph Necessary after Central Venous Catheter Placement in a Surgical Intensive Care Unit?, Am J Surg, pp. 517-522, vol. 180 No. 6, Dec. 2000.
Bankier, Alexander A., Azygos Arch Cannulation by Central Venous Catheters: Radiographic Detection of Malposition and Subsequent Complications, Journal of Thoracic Imaging 12:64-69 (1997).
Barber, JM et al, A Nurse led Peripherally Inserted Central Catheter Line Insertion Service is Effective with Radiological Support, Clin Radiol, pp. 352-354, vol. 57 No. 5, May 2002.
Bard Access Systems, Sherlock Tip Location System, 5 pages, 2006.
Bard Access Systems, Site Rite Vascular Acess Ultrasound System, 4 pages, 2005.
Benchimol, Alberto at al, Right Atrium and Superior Vena Cava Flow Velocity in Man Measured with the Doppler-Catheter Flowmeter-Telemetry System, The Amer Journal of Medicine, pp. 303-309, vol. 48, Mar. 1970.
BioAdvance Lumen Vu, Greenhouse Fund Feb. 2004 Recipient, www.bioadvance.com <http://www.bioadvance.com>, 2005.
Borgobello, Bridget, App allows users to view electrocardiograms on smartphones dated Oct. 15, 2010; printed from http://www.gizmag.com/app-to-view-electrocardiograms-on-smartphones/16664/ on Feb. 4, 2011.
Buehrle, Douglas, PICC Placement in Humans using Electromagnetic Detection, <http://www.corpakmedsystems.com/supplement_material/supplementpages/navigator/navarticle.html>, 2008.
C.R. Bard, CathTrack™ Catheter Location System at www.bardaccess.com <http://www.bardaccess.com>, last accessed Apr. 28, 2011.
C.R. Bard, Inc., Bard Electrophysiology Product Catalogue, Bard Catheters, pp. 74-75 (2002), USA.
Cadman, A et al, To Clot or Not to Clot? That is the question in Central Venous Catheters, Clinical Radiology, pp. 349-355, vol. 59 No. 4, Apr. 2004.
Calvert, N et al, The Effectiveness and Cost-effectiveness of Ultrasound Locating Devices for Central Venous Access: A Systematic Review and Economic Evaluation, Health Technology Assessment, vol. 7, No. 12, 2003.
Cardella, John F. et al., Interventinal Radiologic Placement of Peripherally Inserted Central Catheters, Journal of Vascular and Interventional Radiology 1993; 4:653-660.
Carlon, R et al, Secondary Migration of a Central Venous Catheter—A Case Report, Minerva Anestesiol, pp. 927-931, vol. 69 No. 12, Dec. 2003.
Caruso, LJ et al, A Better Landmark for Positioning a Central Venous Catheter, J Clinical Monitoring and Computing, pp. 331-334, vol. 17 No. 6, Aug. 2002.

(56) References Cited

OTHER PUBLICATIONS

Cavatorta, et al., "Central Venous Catheter Placement in Hemodialysis: Evaluation of Electrocardiography Using a Guidewire." The Journal of Vascular Access, vol. 2, pp. 45-50, 2001.
Chalkiadis, GA et al, Depth of Central Venous Catheter Insertion in Adults: An Audit and Assessment of a Technique to Improve Tip Position, Anaesth Intensive Care, pp. 61-66, vol. 26 No. 1, Feb. 1998.
Chamsi-Pasha, Hassan et al, Cardiac Complications of Total Parenteral Nutrition: The Role of Two-Dimensional Echocardiography in Diagnosis, Annals of the Royal College of Surgeons of England, pp. 120-123, vol. 71, 1989.
Chang, Thomas C. et al., Are Routine Ch Ladiographs Necessary After Image-Guided Placement of Internal Jugular Central Venous Access Devices?, AJR Feb. 1998;170:335-337.
Chaturvedi et al., "Catheter Malplacement During Central Venous Cannulation Through Arm Veins in Pediatric Patients." Journal of Neurosurgical Anesthesiology, vol. 15, No. 3 pp. 170-175, Jan. 2003.
Chen, Zhongping et al, Optical Doppler Tomography: Imaging in vivo Blood Flow Dynamics Following Pharmacological Intervention and Photodynamic Therapy, 7 pages, vol. 67, Photochemistry and Photobiology, 1998.
Cheng, KI et al, A Novel Approach of Intravenous Electrocardiograph Technique in Correct Position the Long-Term Central Venous Catheter, Kaohsiung J Med Sci, pp. 241-247, vol. 16 No. 5, May 2000 (Abstract only).
Cheung, P., et al., The Effect of a Disposable Probe Cover on Pulse Oximetry, Anaesth Intensive Care 2002; 30: 211-214.
Chu, et al., "Accurate Central Venous Port-A Catheter Placement: Intravenous Electrocardiography and Surface Landmark Techniques Compared by Using Transesophageal Echocardiography." The International Anesthesia Research Society, vol. 98, pp. 910-914, 2004.
Claasz, Antonia et al, A Study of the Relationship of the Superior Vena Cava to the Bony Landmarks of the Sternum in the Supine Adult: Implications for Magnetic Guidance Systems, Journal, vol. 12 No. 3, JAVA, Jul. 24, 2007.
Clifford, et al. "Assessment of Hepatic Motion Secondary to Respiration for Computer Assisted Interventions." Computer Aided Surgery, vol. 7, pp. 291-299, 2002.
Colley, Peter S et al, ECG-Guided Placement of Sorenson CVP Catheters via Arm Veins, Anesthesia and Analgesia, pp. 953-956, vol. 63, 1984.
Collier, PE et al, Cardiac Tamponade from Central Venous Catheters, Am J Surg, pp. 212-214, vol. 176 No. 2, Aug. 1998.
ComboWire® Pressure/Flow Guide Wire Ref 9500 Series, Instructions for Use, Apr. 2011.
Corsten, et al., "Central Placement Catheter Placement Using the ECG-Guided Cavafix-Certodyn SD Catheter." Journal of Clinical Anesthesiology, vol. 6, Nov./Dec. 1994.
Cucchiara, Roy et al, Time Required and Success Rate of Percantaneous Right Atrial Catherization: Description of a Technique, Canad. Anaesth. Soc. J., pp. 572-573, vol. 27, No. 6, Nov. 1980.
Cullinane, DC et al, The Futility of Chest Roentgenograms Following Routine Central Venous Line Changes, Am J Surg, pp. 283-285, vol. 176 No. 3, Sep. 1998.
Curet, Myriam J. et al., University and Practice-based Physicians' Input on the Content of a Surgical Curriculum, The American Journal of Surgery® vol. 178 Jul. 1999, 78-84.
David, et al., "Is ECG-Guidance a Helpful Method to Correctly Position a Central Venous Catheter During Prehospital Emergency Care?" ACTA Anaesthesiologica Scandinavica, vol. 49, pp. 1010-1014, 2005.
DELTEC Cath-Finder® Tracking System Operation Manual, 1994.
EP 13804474.8 filed Jan. 7, 2015 Partial European Search Report dated May 23, 2016.
U.S. Appl. No. 12/900,750, filed Oct. 8, 2010 Final Office Action dated Oct. 19, 2015.
CN 201380031663.3 filed Dec. 15, 2014 Office Action dated Jul. 12, 2017.
U.S. Appl. No. 12/900,750, filed Oct. 8, 2010 Final Office Action dated Aug. 4, 2017.
U.S. Appl. No. 13/206,396, filed Aug. 9, 2011, Non-Final Office Action dated May 26, 2017.
U.S. Appl. No. 14/190,591, filed Feb. 26, 2014 Non-Final Office Action dated May 17, 2017.
CN 201380031663.3 filed Dec. 15, 2014 Office Action dated Dec. 21, 2017.
CN 201480010486.5 filed Aug. 25, 2015 Office Action dated Nov. 16, 2017.
U.S. Appl. No. 13/206,396, filed Aug. 9, 2011, Final Office Action dated Jan. 25, 2018.
U.S. Appl. No. 14/190,591, filed Feb. 26, 2014 Final Office Action dated Oct. 30, 2017.
U.S. Appl. No. 14/190,591, filed Feb. 26, 2014 Non-Final Office Action dated Apr. 19, 2018.
U.S. Appl. No. 13/206,396, filed Aug. 9, 2011 Final Office Action dated Oct. 18, 2019.
U.S. Appl. No. 13/206,396, filed Aug. 9, 2011 Notice of Allowance dated Dec. 30, 2019.
U.S. Appl. No. 14/190,591, filed Feb. 26, 2014 Board Decision dated Oct. 17, 2019.
U.S. Appl. No. 13/206,396, filed Aug. 9, 2011 Non-Final Office Action dated Mar. 19, 2019.
CN 201380031663.3 filed Dec. 15, 2014 Office Action dated Jan. 19, 2017.
CN 201380031663.3 filed Dec. 15, 2014 Office Action dated Jun. 1, 2016.
CN 201480010486.5 filed Aug. 25, 2015 Office Action dated Feb. 28, 2017.
EP 13804474.8 filed Jan. 7, 2015 Extended European Search Report dated Aug. 31, 2016.
EP 14756632.7 filed Aug. 24, 2015 Extended European Search Report dated Sep. 30, 2016.
EP 14756632.7 filed Aug. 24, 2015 Partial European Search Report dated Sep. 30, 2016.
U.S. Appl. No. 12/900,750, filed Oct. 8, 2010 Non-Final Office Action dated Jan. 26, 2017.
U.S. Appl. No. 12/900,750 filed Oct. 8, 2010 Advisory Action dated Apr. 9, 2020.
U.S. Appl. No. 161709,664 filed Dec. 10, 2019 Non-Final Office Action dated Jun. 24, 2020.

\* cited by examiner

120

| Zone | Average Image Intensity | ≤ Threshold Intensity |
|---|---|---|
| 1 | $X_1$ | YES |
| 2 | $X_2$ | YES |
| 3 | $X_3$ | NO |
| ⋮ | ⋮ | ⋮ |
| N | $X_n$ | YES |

*FIG. 10*

APPARATUS AND METHODS FOR DETECTION OF A REMOVABLE CAP ON AN ULTRASOUND PROBE

CROSS-REFERENCE TO RELATED APPLICATIONS

This application claims the benefit of U.S. Provisional Patent Application No. 61/660,201, filed Jun. 15, 2012, and titled "Apparatus and Methods for Detection of a Removable Cap on an Ultrasound Probe," which is incorporated herein by reference in its entirety.

BRIEF SUMMARY

Briefly summarized, embodiments of the present invention are directed to an ultrasound imaging device that includes the ability to determine when a component, such as a removable probe cap, is attached to a portion of an ultrasound probe thereof. Such a cap can include a spacer component to provide a standoff for the probe head, which enables relatively shallow subcutaneous structures of the patient's body to be suitably imaged. The spacer component of the probe cap is implemented in one embodiment as an acoustically transparent hydrogel insert that enables the cap to slide easily over the skin of a patient during ultrasound imaging procedures. The probe cap is configured to be removably attachable to the head portion of the probe so as to be disposed of after use, in one embodiment.

Detection of probe cap attachment to the ultrasound probe enables the resultant ultrasound image to be adjusted automatically by the ultrasound imaging system. In one embodiment, adjustment of the image includes removing from the image the portion thereof corresponding to the hydrogel probe cap. By so doing, the top of the ultrasound image displayed by the imaging device will correspond with the surface of the patient's skin, thus facilitating relatively easy interpretation of the image by the clinician performing the imaging procedure.

In one embodiment, an ultrasound imaging system comprises an ultrasound probe, a cap or other component attachable to the probe, and a component attachment detection system for detecting attachment of the component to the probe. Once the cap is detected, an aspect of an ultrasound image produced by the imaging system is modified, including cropping of the image to remove undesired portions of the cap, such as the spacer component.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 10 is a table showing aspects of a method for detecting the attachable cap of the ultrasound imaging system of FIG. 1 according to one embodiment;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to an ultrasound imaging device including an ultrasound probe for ultrasonically imaging subcutaneous tissues of a body of a patient. More particularly, apparatus and methods are disclosed for determining when a component, such as a removable probe cap, is attached to a portion of an ultrasound probe. Such a cap is employed in one embodiment to act as a spacer component to provide a standoff for the probe head, which enables relatively shallow subcutaneous structures of the patient's body to be suitably imaged. The spacer component of the probe cap is implemented in one embodiment as an acoustically transparent hydrogel insert that enables the cap to slide easily over the skin of a patient during ultrasound imaging procedures. The probe cap is configured to be removably attachable to the head portion of the probe so as to be disposed of after use, in one embodiment.

Detection of probe cap attachment to the ultrasound probe enables the resultant ultrasound image to be adjusted automatically by the ultrasound imaging system. In one embodiment, adjustment of the image includes removing from the image the portion thereof corresponding to the hydrogel probe cap. By so doing, the top of the ultrasound image displayed by the imaging device will correspond with the surface of the patient's skin, thus facilitating relatively easy interpretation of the image by the clinician performing the imaging procedure.

Figure 1:
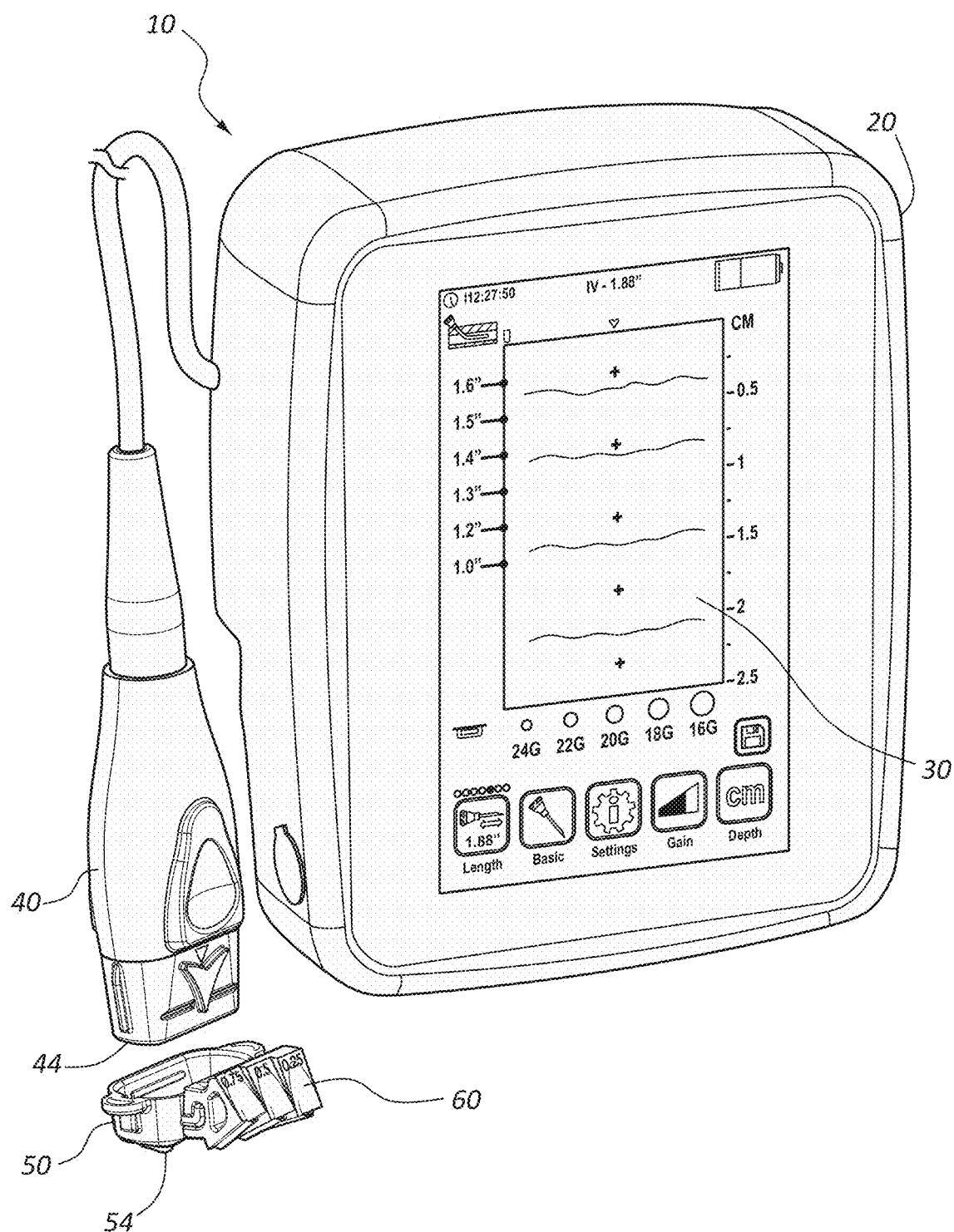
FIG. 1 is a perspective view of an ultrasound imaging system according to one embodiment.

FIG. 1 shows various components of an ultrasound imaging system ("system") 10, according to one embodiment. As shown, the system 10 includes a console 20 housing various electronic and other components necessary for processing and depicting ultrasonic images. The console 20 includes a touchscreen display 30 for depicting ultrasonic images and for enabling touch-based input by a clinician to control the device and its functionality. A probe 40, containing one or more transducer elements in a head 44 thereof for emitting and receiving ultrasonic signals, is operably attached to the console 20 via a cable or other suitable interface.

An optional probe cap ("cap") 50 is shown for removable attachment to the head 44 of the probe 40 so as to cover the transducer elements disposed therein. The cap 50 in one embodiment includes a hydrogel insert 54 or other suitable ultrasonically transparent material, such as silicone, for providing an ultrasonically transparent interface between the probe head 44 and the skin surface. The hydrogel insert 54 also acts as a spacer component to provide a standoff distance between the surface of the probe head 44 and the surface of the patient's skin. Optionally, a needle guide 60 is slidably attached to the cap 50 to assist with guiding needles through the patient's skin and into the vessel being imaged by the system 10. Further details regarding the probe cap, hydrogel insert, and needle guide can be found in: U.S. Pat. Nos. 10,639,008, filed Aug. 9, 2011, and entitled "Support and Cover Structures for an Ultrasound Probe Head;" 9,788,812, filed Jun. 22, 2012, and entitled "Needle Guide with Selectable Aspects;" and 9,211,107, filed Nov. 7, 2012, and entitled "Ruggedized Ultrasound Hydrogel Insert." Each of the foregoing applications is incorporated herein by reference in its entirety. Note that other ultrasound imaging devices and systems that differ from that shown here can also benefit from the embodiments described herein.

Figure 2:
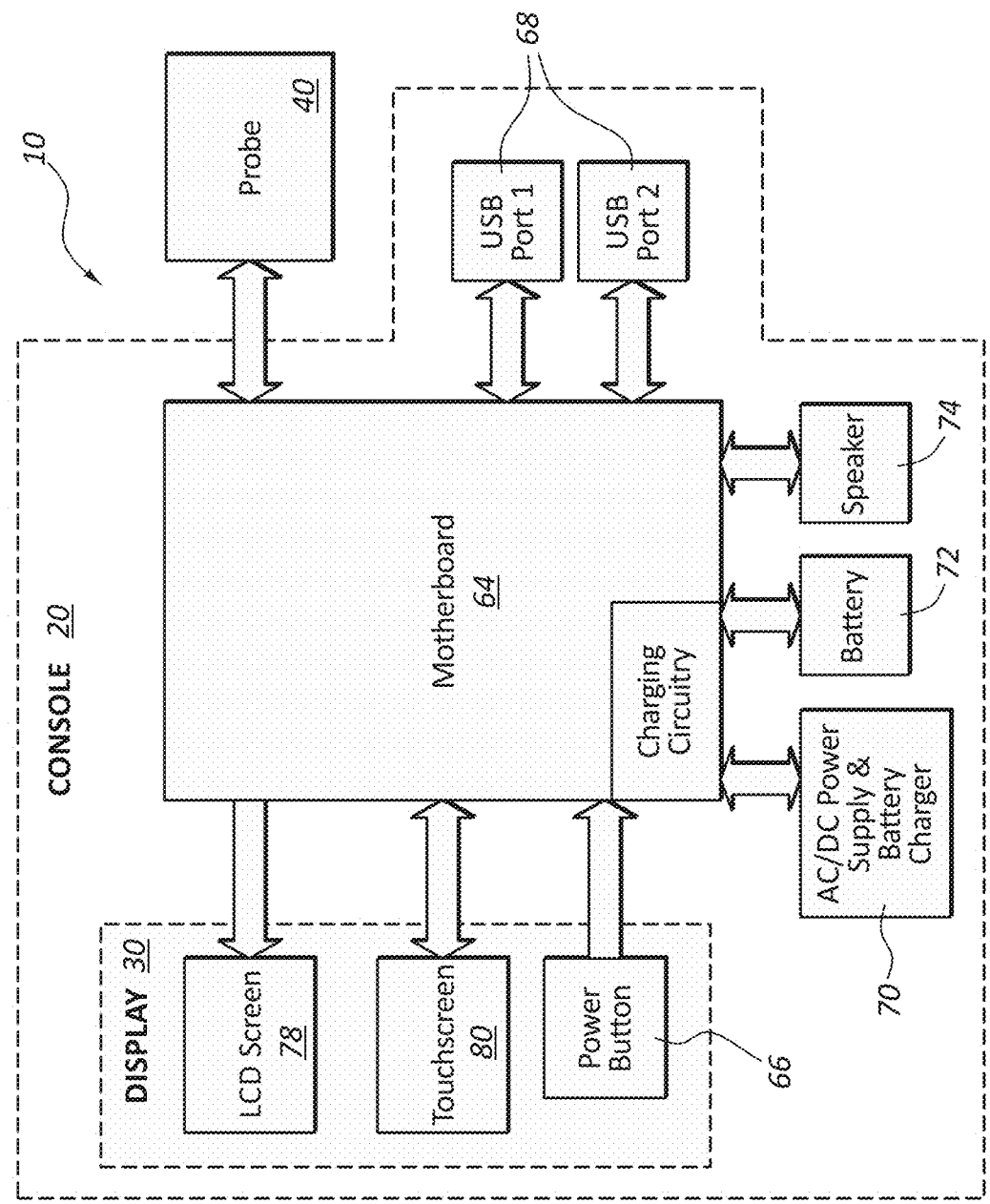
FIG. 2 is a block diagram depicting elements of the ultrasound imaging system of FIG. 1.

FIG. 2 shows a block diagram of the system 10 of FIG. 1, according to one embodiment. In detail, the console 20, display 30, and probe 40 are represented, as in FIG. 1. The console 20 includes therein a motherboard 64 for governing system functionality and includes a processor or other general or special purpose computer, memory, storage locations, and other components for system operation. A power button 66 is included, as are USB ports 68 for interfacing with other devices. An external power supply 70, as well as a battery 72 and speaker 74, are provided for operation. The display 30 in the present embodiment includes an LCD screen 78 or other suitable screen, and a touchscreen 80 to enable touch-based functionality via the display 30. Note that the system 10 can include different, fewer, or more components than those listed here, including those components that enable the system to operate in a networked manner with other local or remote computing or network systems.

Figure 3:
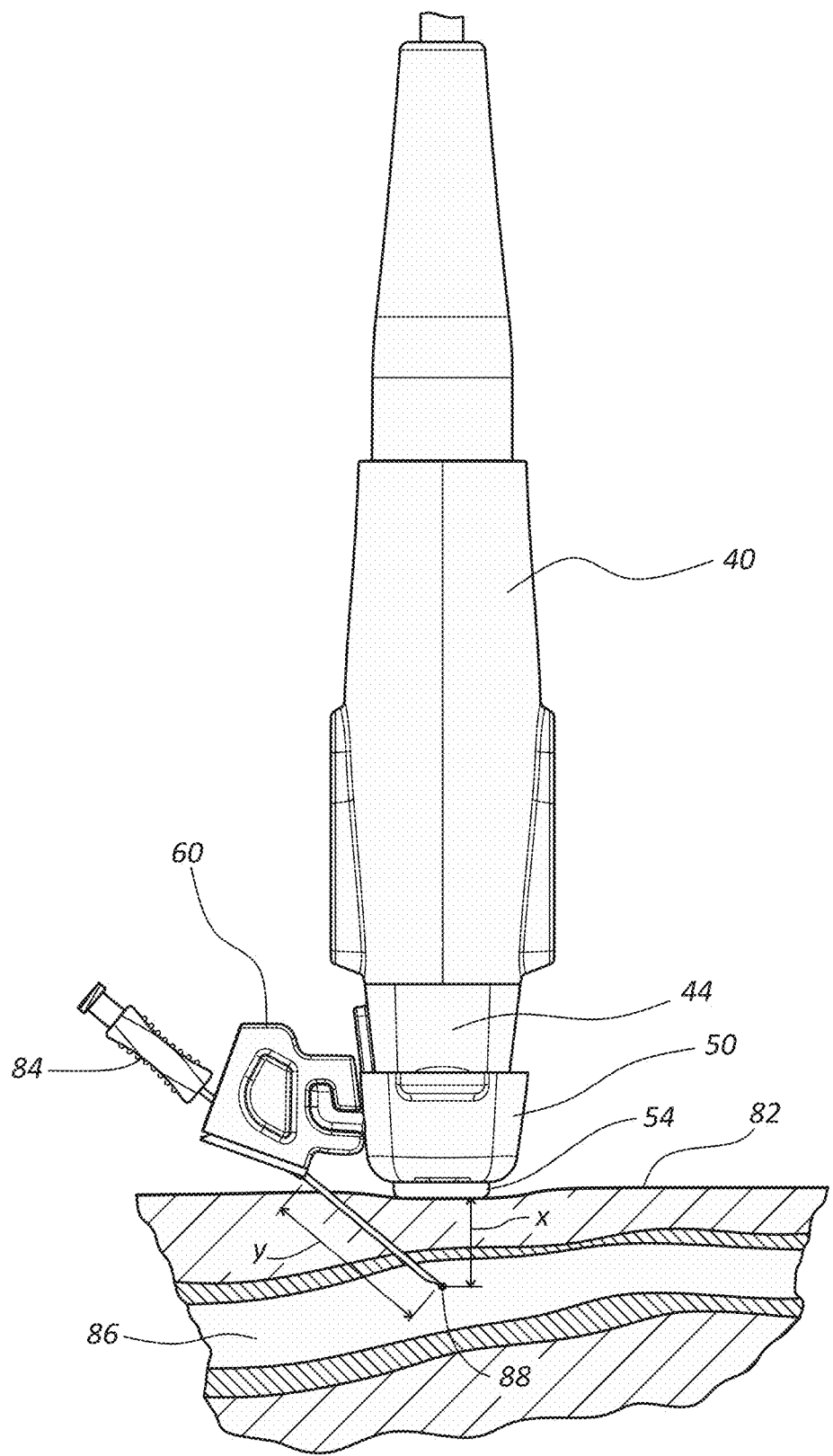
FIG. 3 is partial cross sectional side view showing use of the ultrasound probe of FIG. 1 in accessing a vessel with a needle.

FIG. 3 shows use of the system 10 in accessing a vessel 86 with a needle 84 in preparation for inserting a catheter into the vessel, according to one embodiment. The probe 40, equipped with the head-covering cap 50 and attached needle guide 60, is placed against the skin so as to ultrasonically image a slice of internal body tissue of the patient below the surface of the skin 82. As shown, a target location 88 of the vessel 86 imaged by the probe 40 is disposed a substantially vertical depth "x" below the end of the probe, corresponding to the skin surface 82. An image of the body tissue including the target location 88 is depicted as an ultrasound image on the display 30 of the imaging system 10. Though shown here as a central portion of the vessel 86, the target location 88 can be any one of various subcutaneous locations within the body.

The needle 84, disposed in the needle guide 60, follows an angled catheter insertion path a distance "y" to intercept the target location 88. This catheter insertion path, initially defined by the needle 84, is the same path to be subsequently followed by the catheter in order to gain access to and enter into the vessel 86. The vertical depth x from probe head 44 to the target location 88 can be calculated by a processor or other suitable component of the motherboard 64 of the system 10. Further, the system 10 can be loaded with appropriate data to know the distance y of the catheter insertion path to reach a given target location 88 at a depth x. In the present embodiment, these data are known by virtue of the position of the needle guide with respect to the probe head 44 and the angles in which the needle 84 can be oriented in the needle guide 60 in order to enable the needle to intercept the target location 88. As mentioned, such data can be loaded into the system memory for use by the processor during ultrasonic imaging, as will be described. In another embodiment, the system computes the distance y in real time based on the vertical depth x and other relevant factors.

Figure 4A:
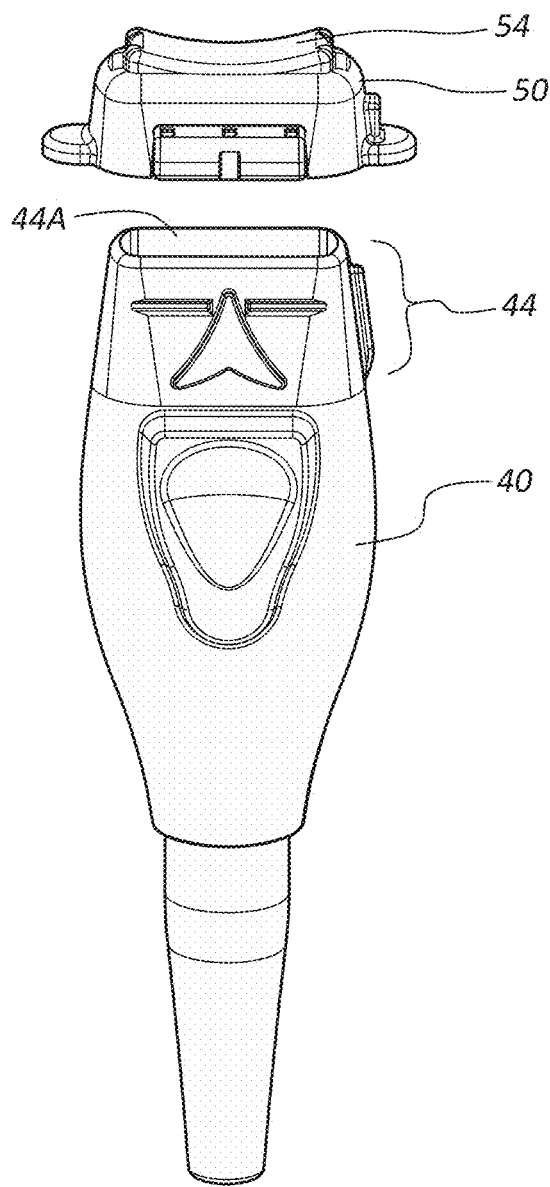
FIGS. 4A and 4B show exploded views of the ultrasound probe of FIG. 1, including an attachable cap and hydrogel insert.
Figure 4B:
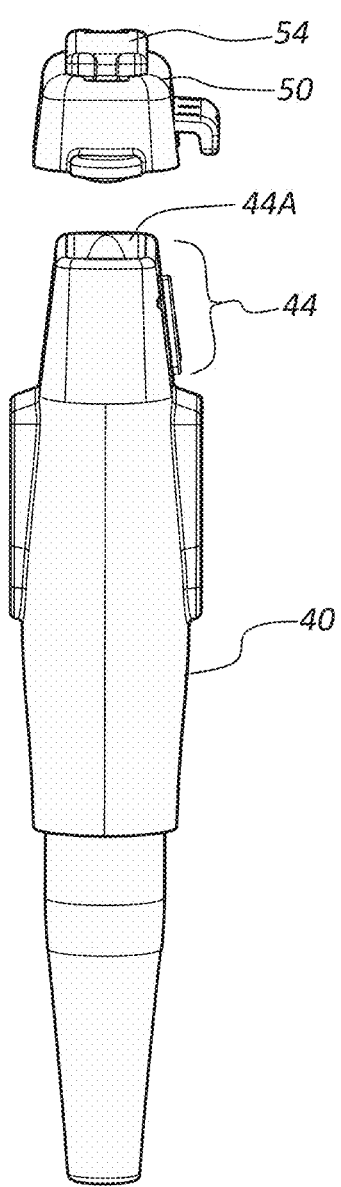

FIGS. 4A and 4B depict further details of the probe 40 and probe cap 50 of the imaging system 10, according to one embodiment. In detail, the removable cap 50 is shown in position for attachment to the probe 40 so as to substantially cover the probe head 44. The cap 50 is secured to the probe 40 via a snap-fit arrangement in the present embodiment. FIGS. 4A and 4B show in greater detail the hydrogel insert 54 that provides both a physical stand-off distance between the patient's skin and a head surface 44A of the probe head 44 as well as a lubricious surface to enable smooth movement of the probe 40 over the skin without further need of lubricating substances. Note that the probe cap can be attached and secured to the probe head by any one of many attachment/securement schemes. Note further that the particular size, shape, and configuration of the probe, probe cap, and hydrogel insert can vary from what is explicitly shown and described herein. In yet another embodiment a separate acoustic standoff is interposed between the ultrasound probe head and the patient's skin. The principles of the present disclosure can therefore be applied to this and other acoustic standoff scenarios.

Figure 5:
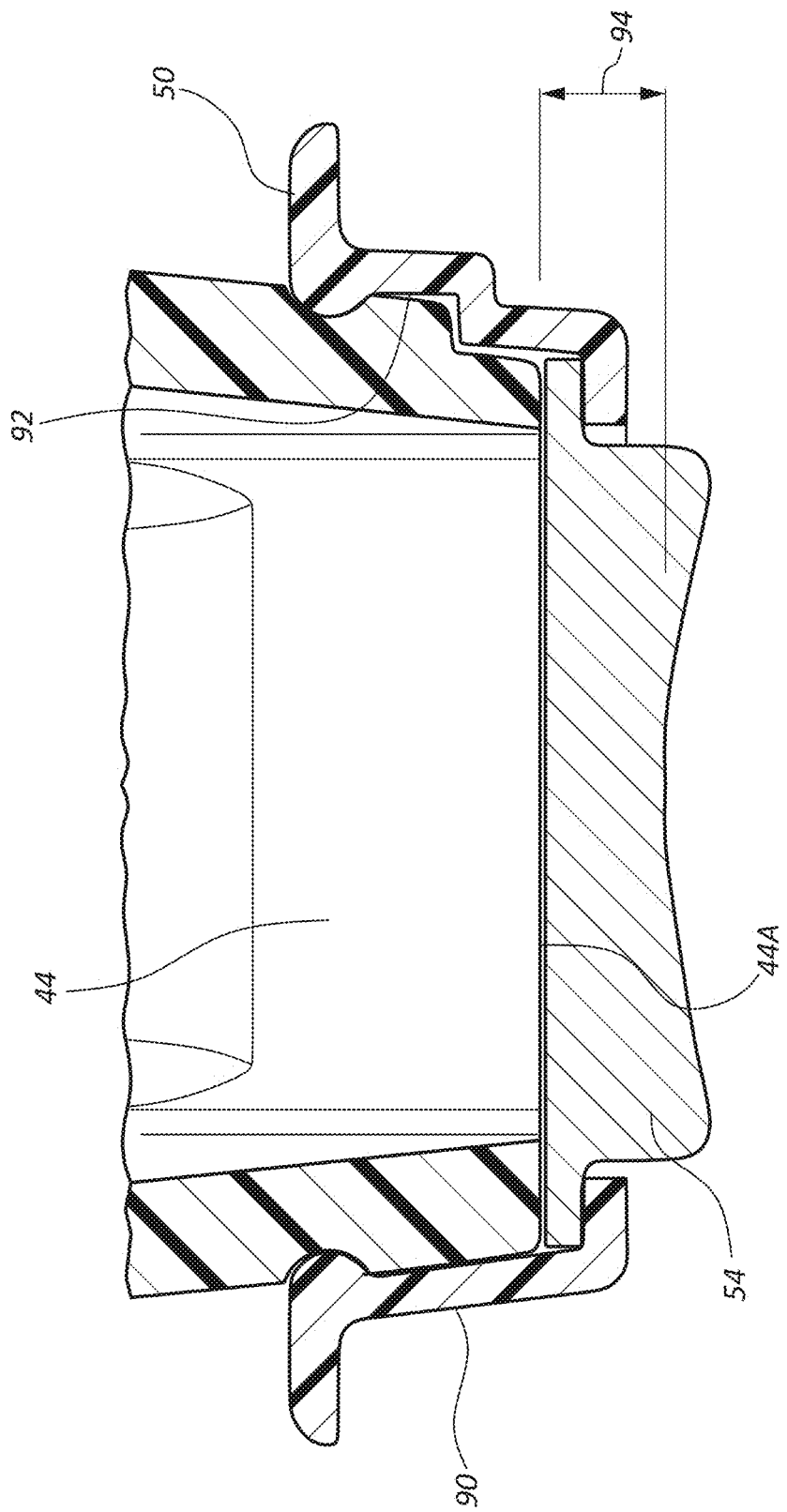
FIG. 5 is a cross sectional side view of a portion of the ultrasound probe and attachable cap of FIG. 1.

FIG. 5 depicts the positional relationship between the probe head surface 44A and the hydrogel insert 54 when the cap 50 is attached to the probe 40 in the manner shown in FIG. 3. In particular, the cap 50 includes a body 90 that defines a cavity 92 into which the probe head 44 is received when the cap is removably mated with the probe 40. Note that a standoff distance 94 exists between the probe head surface 44A and the distal end of the hydrogel insert 54. So configured, the hydrogel insert 54 acts as a spacer component between the head surface 44A and the skin of the patient.

Figure 6A:
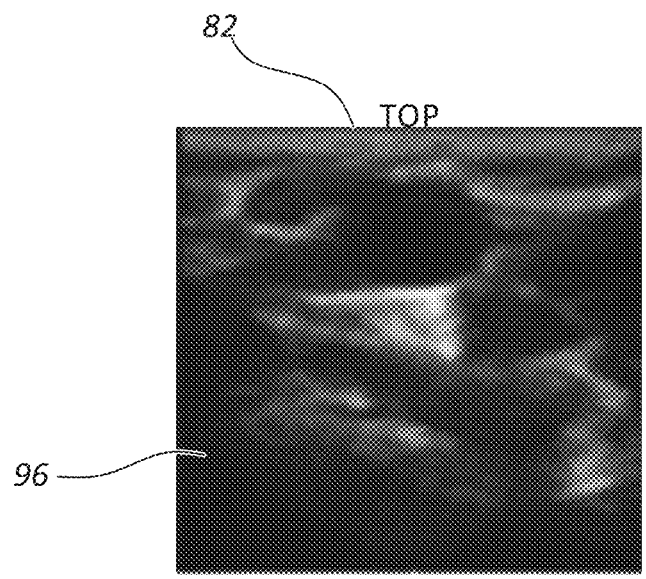
FIGS. 6A and 6B show ultrasound images taken by the ultrasound imaging system of FIG. 1 according to one embodiment.
Figure 6B:
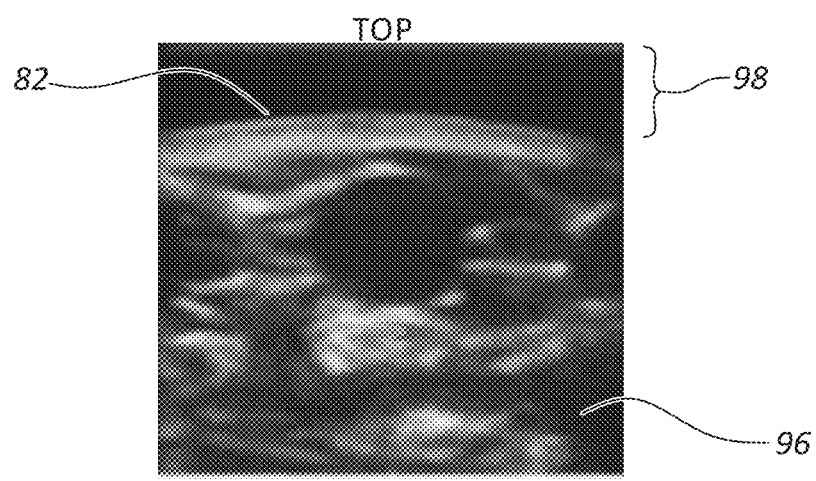

FIGS. 6A and 6B show an ultrasound image 96 produced by the imaging system 10. FIG. 6A shows the image 96 when no cap is attached to the probe 40. In contrast, FIG. 6B shows the image 96 when the cap 50 is attached to the probe 40, as shown in FIG. 5. Because of its standoff distance 94 (FIG. 5), the hydrogel insert 54 of the cap 50 is shown in the image 96, as indicated at 98. The patient's skin surface is also seen at 82. In one embodiment, it is desirable to remove this portion so as to provide an ultrasound image whose top corresponds with the skin surface 82 and not the standoff region 98.

In accordance with one embodiment, a cap detection system ("detection system") is disclosed to enable the imaging system 10 (FIG. 1) to automatically determine whether a cap, such as the probe cap 50 or other component, has been attached to the probe 40. If so, the imaging system can adjust the ultrasound image it produces to desirably remove the standoff region 98 (FIG. 6B) from the image.

Figure 7:
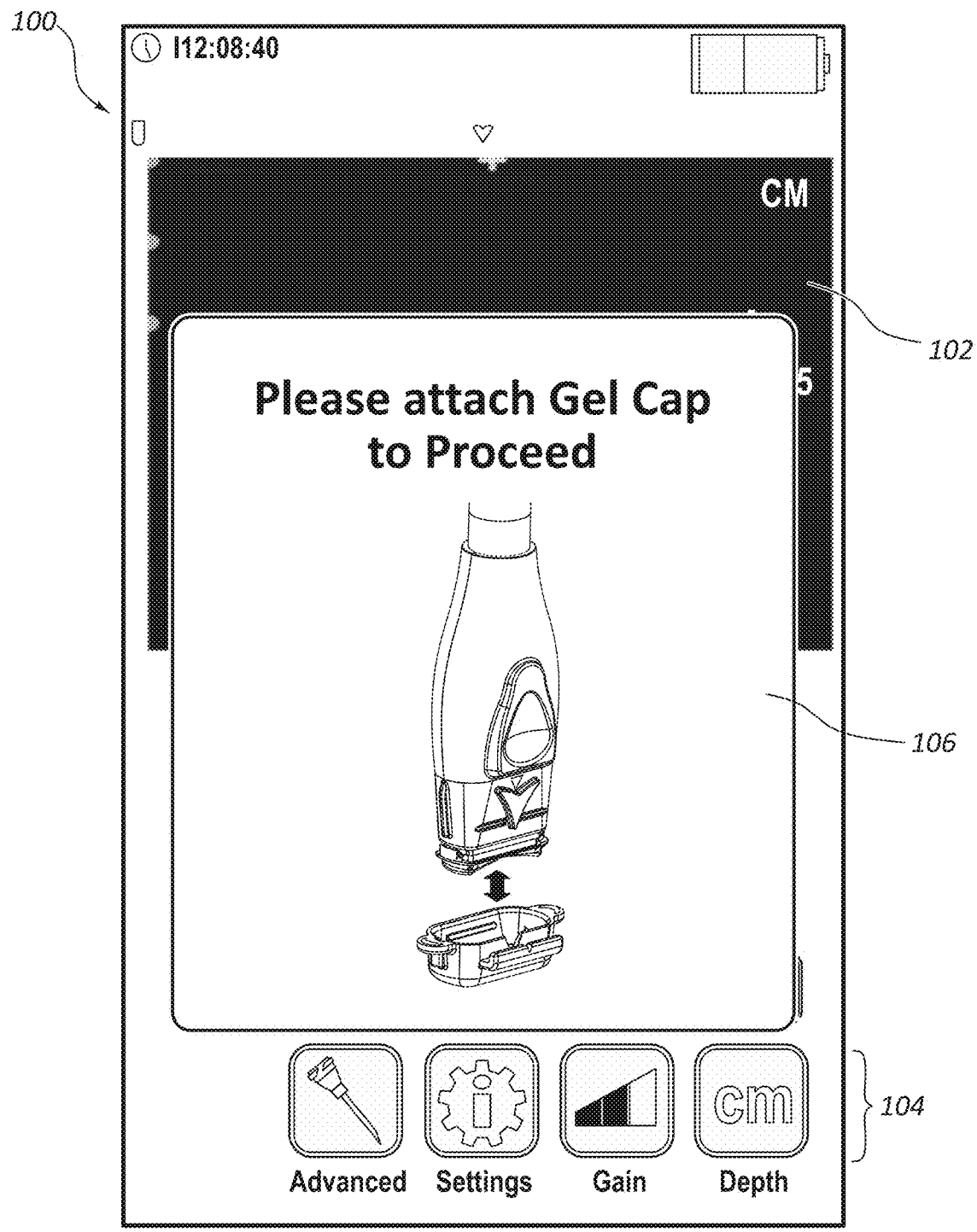
FIG. 7 is a screenshot from the ultrasound imaging system of FIG. 1 according to one embodiment.

In particular, in one embodiment the imaging system 10 can be configured such that full functionality of the imaging system is dependent on the cap 50 being attached to the probe 40. For instance, in the present embodiment and as depicted in FIG. 7, a notification can be presented to alert the user to attach the cap 50 to the probe 40 to enable imaging system functionality. FIG. 7 shows a sample depiction 100 of the display 30 of the imaging system 10. The depiction 100 includes an ultrasound image 102 produced by the probe 40, and a control button field 104. A pop-up window 106 is depicted atop the ultrasound image 102, prompting the user to attach the cap 50 to the probe 40. The pop-up window 106 remains on the display until the detection system detects that the cap 50 has been suitably attached to the probe 40, as depicted in FIG. 3. Once cap attachment is detected by the detection system, the pop-up window 106 is removed and the depiction 100 can include an indicator showing the cap 50 is suitably attached, such as a cap attachment indicator 108, shown in FIG. 8. Of course, other notifications and indicators than the pop-up window 106 and indicator 108, including audio alerts, lights, etc., can be employed. Use of the cap detection system to determine whether the cap 50 has been attached to the probe 40 enables the above functionality.

In other embodiments, functionality of the imaging system to image and display ultrasonic images is not dependent upon whether the cap or other component to be detected is attached to the probe. In yet other embodiments, imaging system functionality is affected in other ways according to whether the cap is attached, such as changing the orientation of the ultrasound image when the cap is detected as being attached. These and other variations are therefore contemplated.

Figure 8:
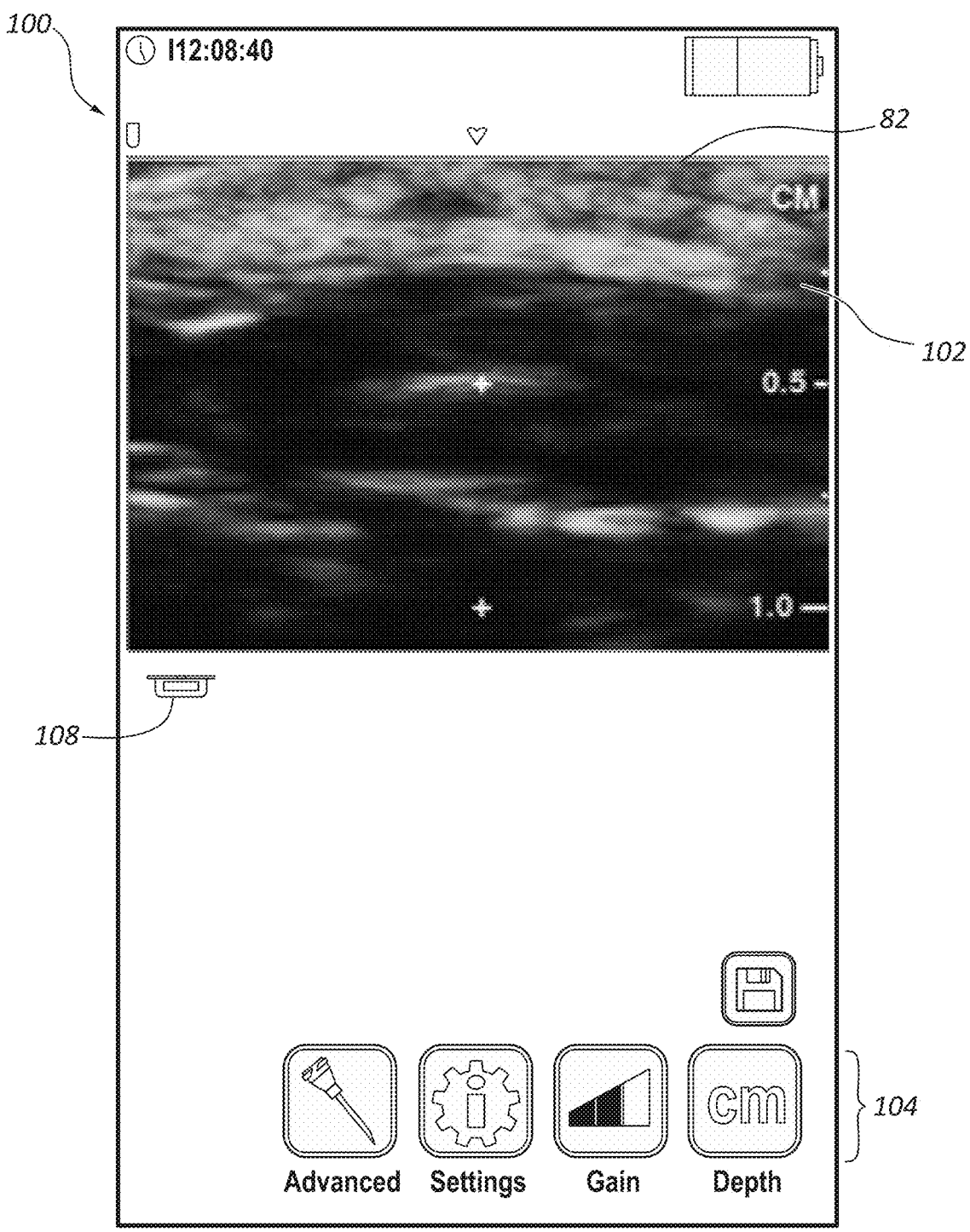
FIG. 8 is a screenshot from the ultrasound imaging system of FIG. 1 according to one embodiment.

Inspection of the screenshot depiction 100 of FIG. 8 will indicate that the ultrasound image 102 has been adjusted such that the top of the image substantially corresponds with the patient's skin. In other words, the portion of the image corresponding to the cap 50 and hydrogel insert 54 has been removed. As discussed above, in one embodiment it is desirable to remove this portion so as to provide the ultrasound image beginning at the surface of the patient's skin.

Figure 9:
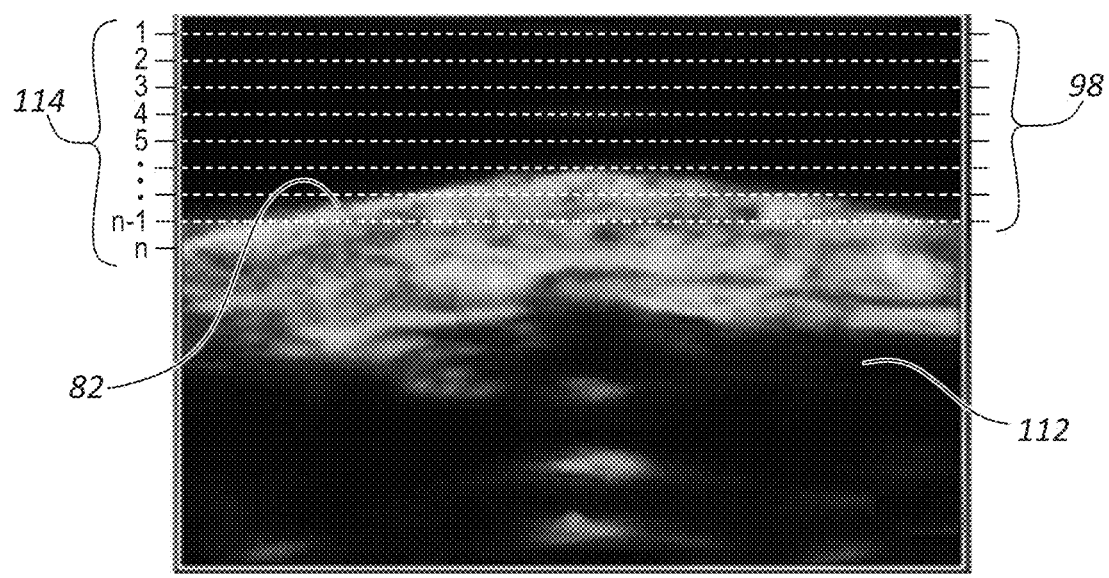
FIG. 9 is an ultrasound image showing sampling zones according to one embodiment.
Figure 18:
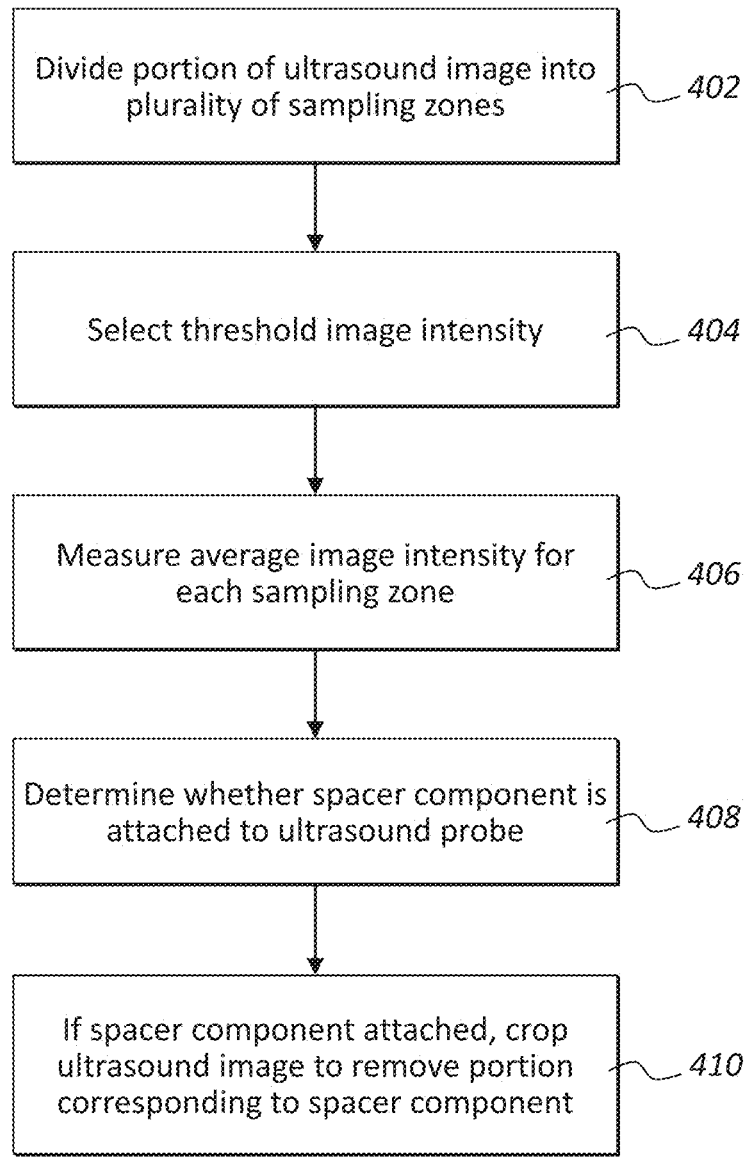
FIG. 18 shows various stages of a method for detecting attachment of a spacer component to an ultrasound probe according to one embodiment.

FIGS. 9 and 18 depict various details regarding a method 400 employed by a cap detection system for detecting attachment of the cap 50 to the probe 40 so as to cover the head 44 according to one embodiment. In the present embodiment the cap detection system employs various components of the imaging system, including a motherboard processor or other suitable component of the imaging system 10 (FIG. 2) and the probe 40 to execute an algorithm for automatic cap detection.

In the present embodiment, and with continuing reference to FIGS. 9 and 18, the above-mentioned algorithm performs the method 400 for detecting whether the cap 50 is suitably attached to the probe 40 by first, at stage 402, dividing a predetermined portion of an ultrasound image 112 into a plurality of sampling zones 114, here shown a series of horizontally extending virtual slices that are vertically stacked atop one another and descending a predetermined distance from the top of the image. The predetermined portion of the image 112 that is covered by the sampling zones corresponds in one embodiment to the expected zone in which the standoff region 98, i.e., the portion of the image that includes the imaged cap 50 and hydrogel insert 54, is expected to be found. The predetermined portion may be pre-programmed into or may be dynamically determined by the system 10. In one embodiment, for example, the standoff distance 94 of the hydrogel insert (FIG. 5) is about 3.9 mm, while the predetermined portion of the ultrasound image that will be covered by sampling zones is about 2.8 mm measured down from the top of the ultrasound image. An example number n of sampling zones 114 is shown in FIG. 9, descending down to and including a portion of the imaged skin surface 82. The number, size, etc. of the sampling zones can vary according to design, user input, etc., and can be dynamically or user-adjustable.

Figure 17:
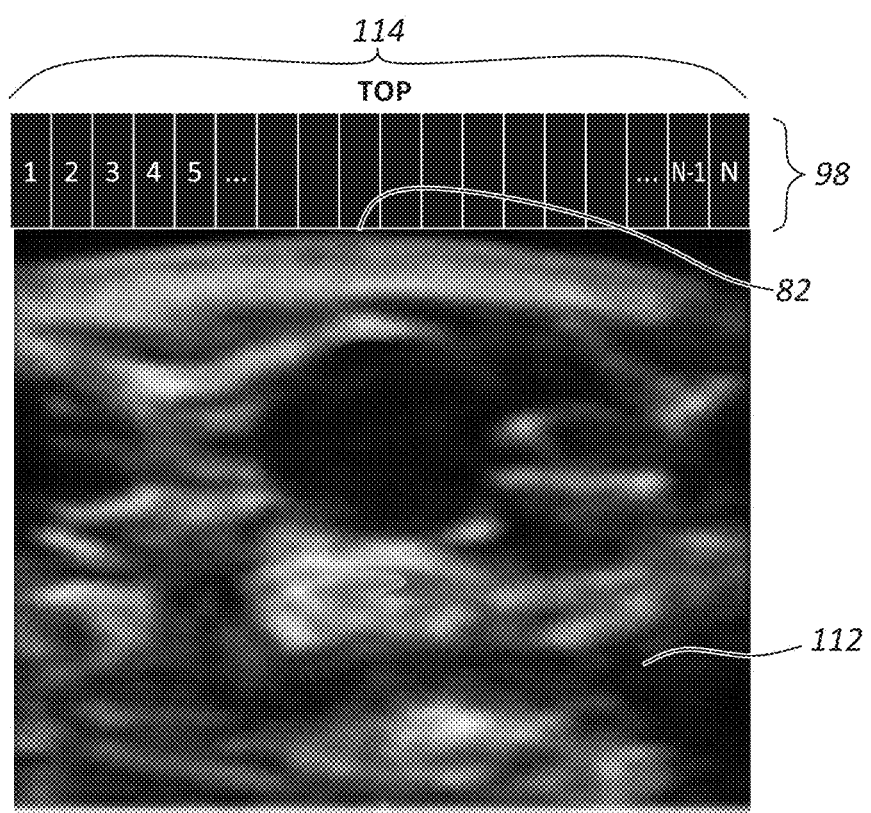
FIG. 17 is an ultrasound image showing sampling zones according to one embodiment.

Another sampling zone configuration that can be employed is depicted in FIG. 17, showing the ultrasound image 112 including a plurality of sampling zones 114 as a series of vertically extending virtual slices that vertically extend downward from the top of the image and are horizontally stacked aside one another across the image to cover the expected or designated standoff region 98. In one embodiment, the number of sampling zones is 20, though other numbers of zones can be employed.

In stage 404, a threshold for image intensity is determined. The image intensity threshold determines the level at which the algorithm considers an ultrasonic signal to represent detected matter. Thus, for each sampling zone 114 an ultrasound signal detected by the probe 40 that includes an image intensity level exceeding the threshold indicates the presence ultrasonically detectable matter for that sampling zone, while those zones having image intensities below the threshold are considered to have no ultrasonically detectable material in them. As the hydrogel insert 54 that forms the standoff region 98 is ultrasonically transparent, sampling zones that include a sufficient portion of the insert will have image intensities below the determined threshold. Note that the image intensity threshold can be pre-programmed into the imaging system 10, user-adjustable, or dynamically determined by the imaging system. In one embodiment, the image intensity can numerically vary between about 0 (low image intensity) and about 255 (high image intensity), and the image intensity threshold is about 5. In another embodiment, the image intensity threshold is about 20. These values, of course, can vary in other embodiments.

In stage 406, an average image intensity for each sampling zone 114 is then measured by the system 10 on the same intensity scale given above. In stage 408, the average image intensities for the sampling zones 114 are then evaluated to determine whether a sufficient number of sampling zones have image intensities equal to or below the threshold image intensity discussed above. Table 120 in FIG. 10 shows the collection of such data by the imaging system 10 in one embodiment. If a sufficient number of sampling zones have image intensities equal to or below the threshold value, it is determined by the system 10 that the standoff region 98 is being detected and thus the probe cap 50 is suitably attached to the probe 40. If an insufficient number of sampling zones have image intensities equal to or below the threshold image intensity, the system 10 determines that no cap is attached to the probe 40.

The number of sampling zones 114 that must have image intensities equal to or below the threshold image intensity can be pre-programmed into the imaging system 10, user-adjustable, or dynamically determined by the imaging system. In one embodiment, if at least 19 sampling zones 114 are found to have image intensities equal to or below the threshold image intensity, the system 10 can determine that the cap 50 is attached to the probe 40. Correspondingly, if less than two sampling zones 114 are found to have to have image intensities equal to or below the threshold image intensity, the system 10 can determine that the cap 50 is not attached to the probe 40. These numbers can vary in other embodiments.

The above process is iterated by the system 10 for each imaging cycle during ultrasound imaging such that evaluations for the presence of the probe cap are repeatedly performed during system operation. Each imaging cycle produces a corresponding ultrasound image, or frame, and multiple frames per second can be produced by the system 10, in one embodiment. In another embodiment, the above process can be iterated at a regular or user-defined interval, if desired.

In one embodiment, a certain number of consecutive ultrasound images frames having a suitable number of sampling zones 114 that are equal to or below the threshold image intensity must be encountered for the system 10 to determine that the cap 50 is attached to the probe 40. For instance, in the present embodiment, at least five ultrasound image frames in a row that are sequentially produced by the system 10 must each have a suitable number of sampling zones 114 that are equal to or below the threshold image intensity for the system 10 to determine that the cap 50 is attached to the probe 40, though this number can vary.

For example, and in light of the above, the system 10 in one embodiment will determine that the cap 50 is suitably attached to the probe 40 if, for five consecutive ultrasound image frames, more than 18 sampling zones 114 are found to have image intensities equal to or below the threshold image intensity. Correspondingly, the system 10 will determine that the cap 50 is not suitably attached to the probe 40 if, for five consecutive ultrasound image frames, less than two sampling zones 114 are found to have to have image intensities equal to or below the threshold image intensity. Once the cap attachment status is set by the system 10 as just described, it will not change unless the above more-than-18 or less-than-two sampling zone conditions are met for five consecutive ultrasound image frames. Should the number of qualifying sampling zones fall within 2-18 for a given ultrasound image frame, the cap attachment status is not changed from its previous setting and the counter for determining five consecutive image frames is reset.

Once it determines that the cap 50 is suitably attached to the probe 40 as described above, the system 10 adjusts the image 112 to crop or remove the region determined to correspond to the standoff region 98 representing the hydrogel insert 54. This results in a view similar to the depiction 100 shown in FIG. 8 wherein the skin surface 82 is positioned proximate the top of the ultrasound image 102.

As mentioned above, during iterative execution of the above process the system 10 can determine that the cap 50 has been removed from or is not currently attached to the probe 40. Once the system 10 determines that the cap 50 is not suitably attached to the probe 40, the cropping of the image described above is not performed, and the full ultrasound image is depicted.

Figure 19:
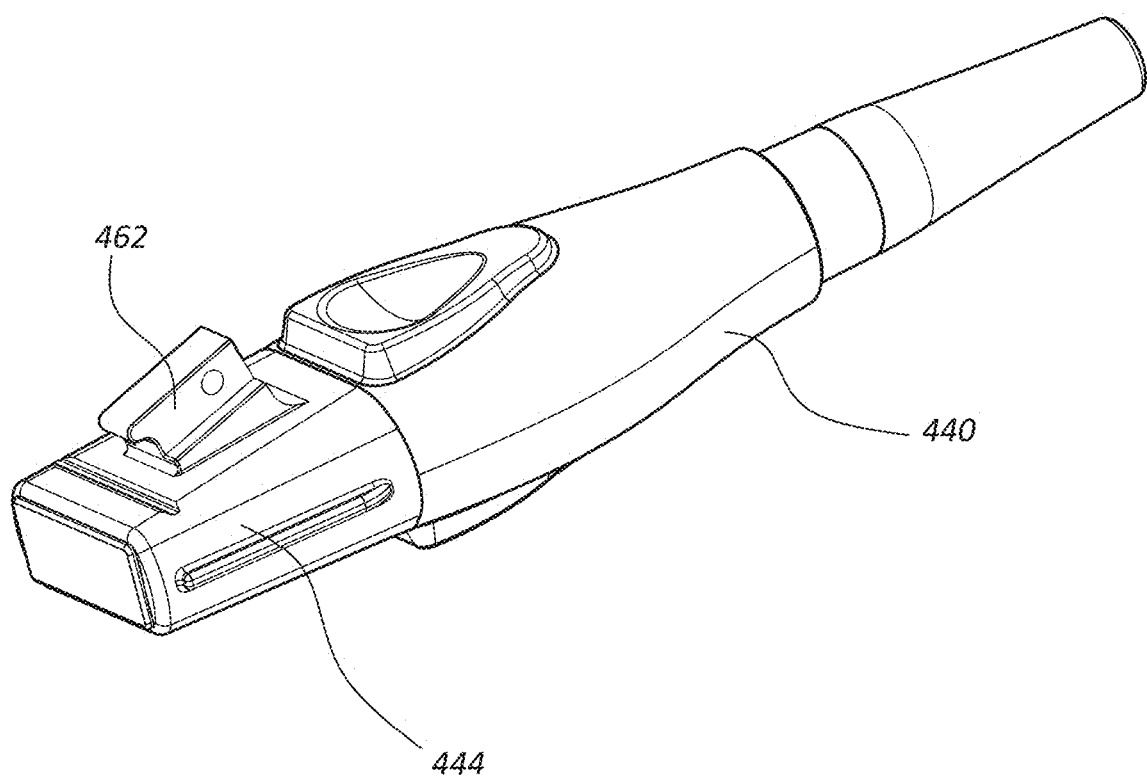
FIG. 19 is a perspective view of an ultrasound probe according to one embodiment.

In addition to ultrasound image cropping, it is appreciated that other/additional actions can be taken by the system 10 once the cap 50 is determined either to be attached or detached from the probe 40. For instance, in one embodiment, the orientation of the ultrasound image can be flipped and image characteristics such as grayscale can be modified when the cap is detected as suitably attached. FIG. 19 shows one example of a probe 440 that can utilize such functionality. As shown, the probe 440 includes a head portion 444 and a fixture 462 for receiving thereon a detachable needle guide. The fixture 462 can be adapted to receive thereon needle guides such as those disclosed in U.S. Pat. No. 5,235,987, entitled "Needle Guide," and U.S. Pat. No. 8,574,160, filed Dec. 18, 2009, and entitled "Needle Guides for a Sonographic Imaging Device." Each of the aforementioned documents is incorporated herein by reference in its entirety.

Note that in addition to the above-described, other algorithms can be executed by the system 10 to determine attachment of the cap to the probe. One possible algorithm employs a Hough transform to identify and locate the interface between the skin surface and the hydrogel insert in the ultrasound image in a predetermined or programmed area of the image. If the interface is detected with sufficient certainty, the system 10 can determine that the cap is suitably attached to the probe.

Figure 11A:
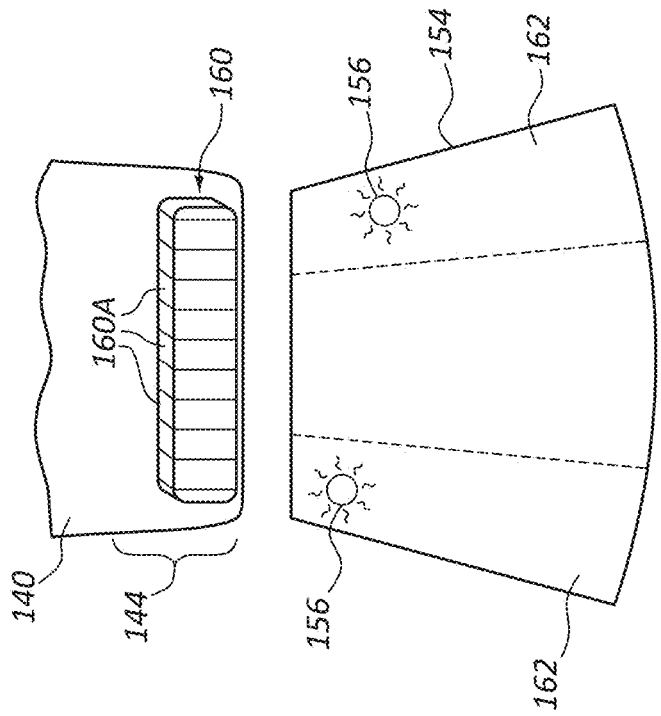
FIGS. 11A and 11B are various views of an ultrasound probe and hydrogel insert according to one embodiment.
Figure 11B:
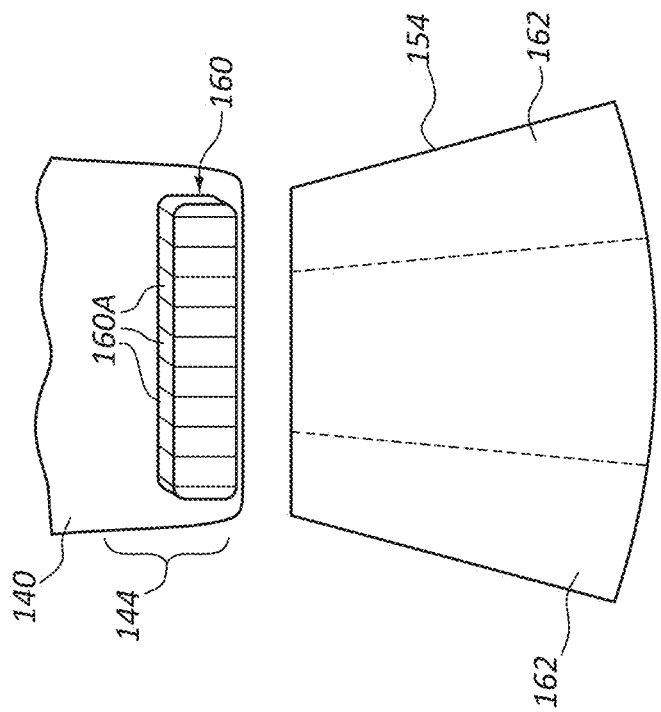

FIGS. 11A and 11B depict details of a cap detection system according to another embodiment, wherein a probe 140 including a head 144 in which a transducer 160 of multiple transducer elements 160A is disposed. A hydrogel insert 154 is shown as operably positioned proximate the probe head 144 such that ultrasonic signals from the transducer 160 can pass through the hydrogel insert 154 to and from the body tissue. In the present embodiment, the hydrogel insert 154 acts as a spacer component and is included in a cap that is removably attachable to the probe 140.

As shown in FIG. 11B, one or more ultrasonically reflective markers 156 can be included in the hydrogel insert 154 in one or more detection regions 162 of the insert. In the present embodiment, two detection regions 162 are longitudinally defined in the hydrogel insert 154 and extend in the direction of travel of ultrasonic signals emitted from the probe head transducer 160. The system 10 is configured to detect the reflective marker(s) 156 when the hydrogel insert-including cap is suitably attached to the probe 140. Thus, if the reflective markers 156 are detected, the imaging system 10 can determine that the cap is suitably attached to the probe 140. No detection of the reflective markers 156 by the imaging system 10 indicates that no cap is attached. The number, types, position, and other configuration of the hydrogel insert and its reflective markers/detection regions can vary from what is explicitly shown and described herein.

Figure 12:
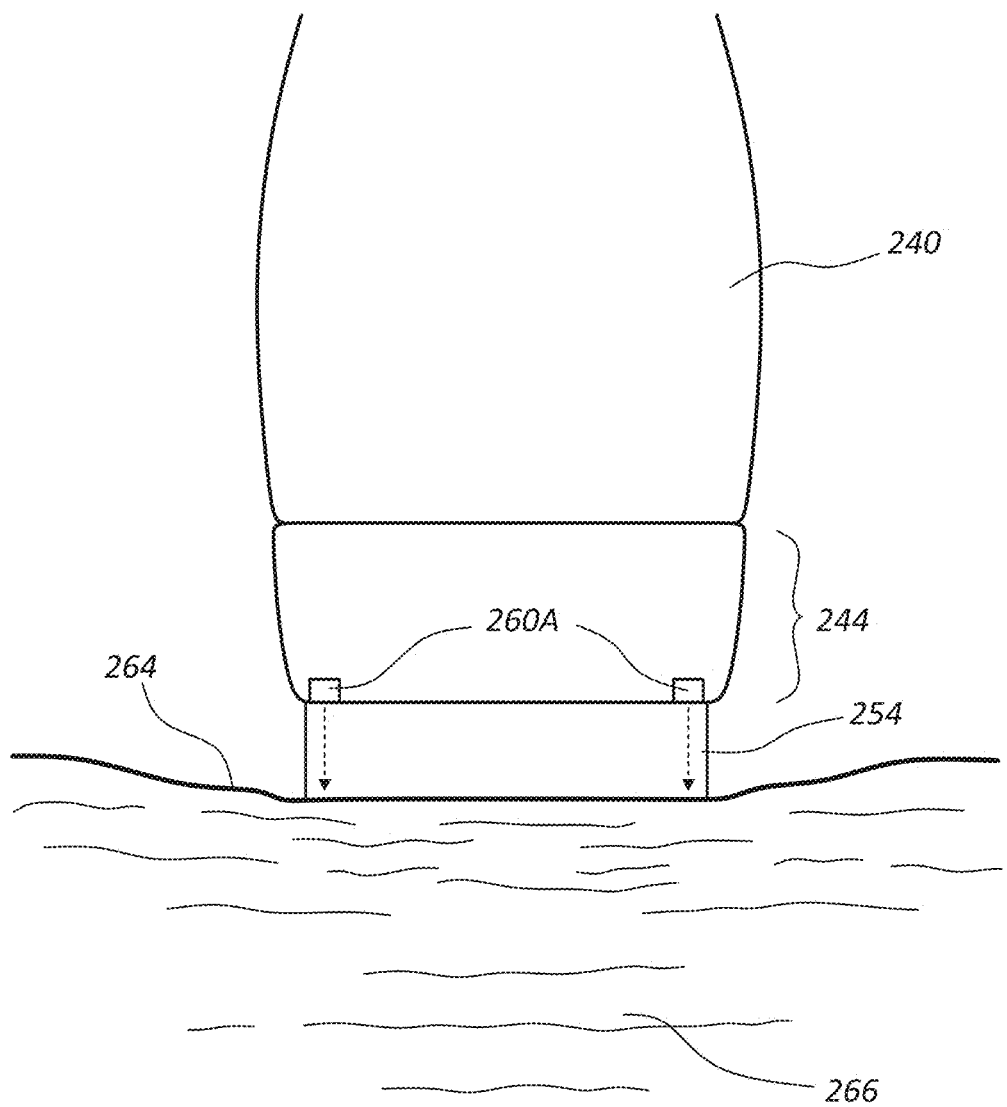
FIG. 12 is a simplified side view of an ultrasound probe and imaged portion of body tissue in accordance with one embodiment.

FIG. 12 depicts details of a cap detection system according to another embodiment, wherein a probe 240 including a head 244 in which a plurality of transducer elements 260A is disposed. Note that, for clarity, only the end transducer elements 260A are shown in FIG. 12. A hydrogel insert 254 is shown as operably positioned proximate the probe head 244 such that ultrasonic signals from the transducer can pass through the hydrogel insert 254 to and from the body tissue. In the present embodiment, the hydrogel insert 154 acts as a spacer component and is included in a cap that is removably attachable to the probe 140.

As shown, one or more transducer elements—in this embodiment, the end transducer elements 260A—can be designated by the imaging system 10 to continuously emit ultrasound signals and monitor the reflected signals. Instead of being used for ultrasonic imaging of tissue, the end transducer elements 260A are used to monitor for the presence of the hydrogel insert, and thus cap attachment. Should no reflection be detected in the standoff region corresponding to the hydrogel insert 254, the system 10 determines that the cap including the hydrogel insert is suitably attached. Correspondingly, a relatively strong ultrasonic reflection within the expected standoff region indicates that no cap and hydrogel insert is present. The region to be monitored for the presence of ultrasonic reflections can be user-defined, dynamically defined, or pre-programmed into the imaging system 10.

In one embodiment, multiple transducer elements along the length of the transducer can be utilized to monitor for the hydrogel insert and associated cap, as just described, in contrast to using only the end transducers. For instance, a transducer element at or near the middle of the transducer can be employed, in addition to the end transducer elements. In another embodiment, the end transducer elements 260A are utilized to identify and locate the hydrogel-skin surface interface, i.e., a depth where a substantially acoustically transparent region transitions abruptly to an acoustically non-transparent region in a region of interest that is pre-programmed, dynamically determined by the system, input by a user, etc. If such an interface is encountered at a depth in accordance with expected values, the imaging system 10 can determine that the cap is suitably attached to the probe.

Note further that, in at least the present embodiment, the imaging system can dynamically determine the height of the hydrogel insert acting as a spacer component. In such cases, the imaging system can alter the ultrasound image once the cap has been detected as being attached to the probe so as to crop only that portion of the image corresponding to the determined height of the hydrogel insert. In other embodiments, a look-up table including the measure of image cropping distances can be stored and accessed by the system once the size of the hydrogel insert or other suitable spacer component has been determined so as to crop a desired portion of the ultrasound image.

Figure 13:
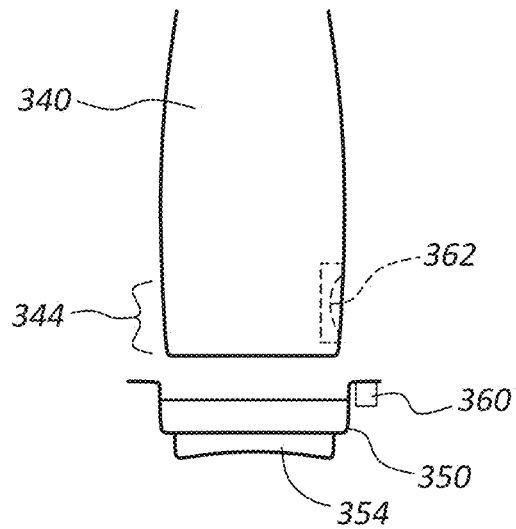
FIG. 13 is a simplified side view of an ultrasound probe and attachable cap according to one embodiment.

FIG. 13 depicts details of a cap detection system according to another embodiment, wherein a probe 340 including a head 344 in which a transducer is disposed. A cap 350 including a hydrogel insert 354 that acts as a spacer component is shown as ready for attachment to the probe 340. A magnetic element, such as a permanent magnet 360, is included with the cap 350. A magnetic sensor 362, such as a Hall Effect sensor, is included with the probe 340 and is configured to detect the magnetic field of the magnet 360 when the cap 350 is attached to probe 340. Note that the type, size, position, and other configuration of the magnetic elements and magnetic sensor can vary from what is shown and described herein.

Figure 14:
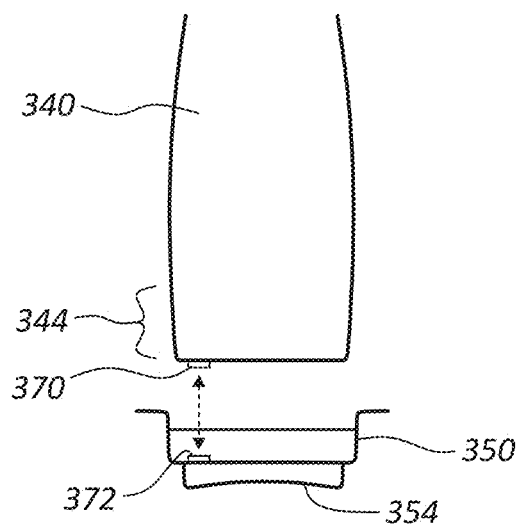
FIG. 14 is a simplified side view of an ultrasound probe and attachable cap according to one embodiment.

FIG. 14 depicts details of a cap detection system according to another embodiment, wherein an infrared or other electromagnetic wave-based transceiver 370 is included with the head 344 of the probe 340. An infrared or other suitable reflector 372 is optionally included on the cap 350 and positioned to reflect infrared signals produced by the transceiver 370 when the cap 350 is suitably attached to probe 340. Note that the type, size, position, and other configuration of the transceiver and reflector can vary from what is shown and described herein.

Figure 15:
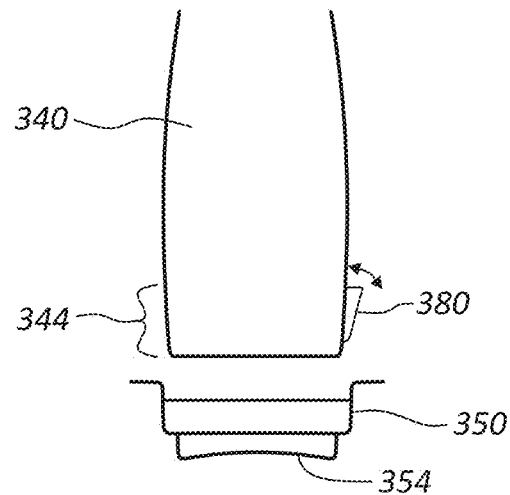
FIG. 15 is a simplified side view of an ultrasound probe and attachable cap according to one embodiment.

FIG. 15 depicts details of a cap detection system according to another embodiment, wherein a mechanical switch 380 is included on the probe such that it is depressed or otherwise actuated when the cap 350 is suitably attached to the probe. This will indicate to the imaging system 10 that the cap is suitably attached. The type, size, position, and other configurations of the switch can vary from what is shown and described here. For instance, in one embodiment an optical switch can be used to indicate when the cap is suitably attached to the probe.

Figure 16:
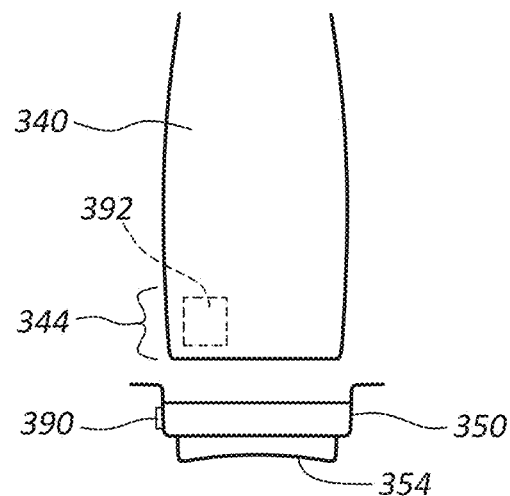
FIG. 16 is a simplified side view of an ultrasound probe and attachable cap according to one embodiment.

FIG. 16 depicts details of a cap detection system according to another embodiment, wherein the cap 350 includes an RFID 390 chip that is detectable by a corresponding RFID reader 392 disposed in the head 344 or other portion of the probe 340 when the cap 350 is suitably attached to the probe. The RFID chip 390 can include one of various types, including active and passive chips, etc.

Figure 20:
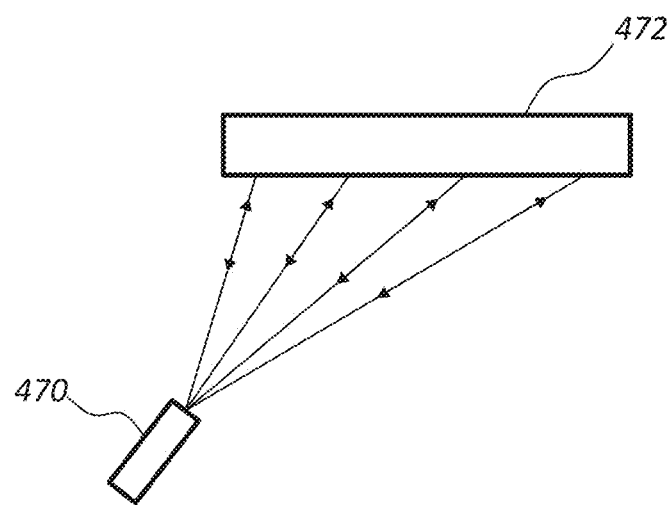
FIG. 20 shows elements of a cap detection system according to one embodiment.
Figure 21:
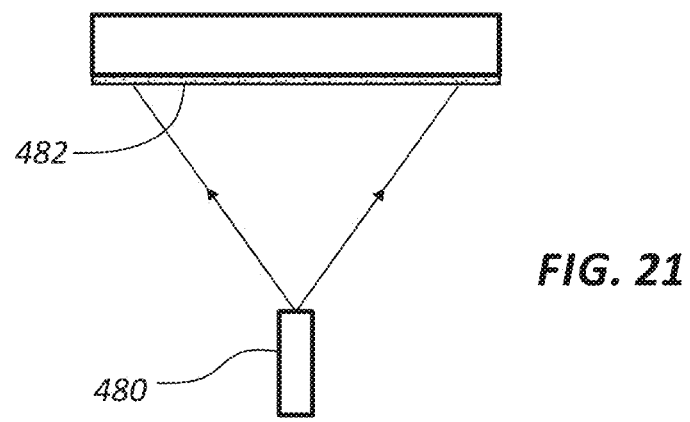
FIG. 21 shows elements of a cap detection system according to one embodiment.
Figure 22:
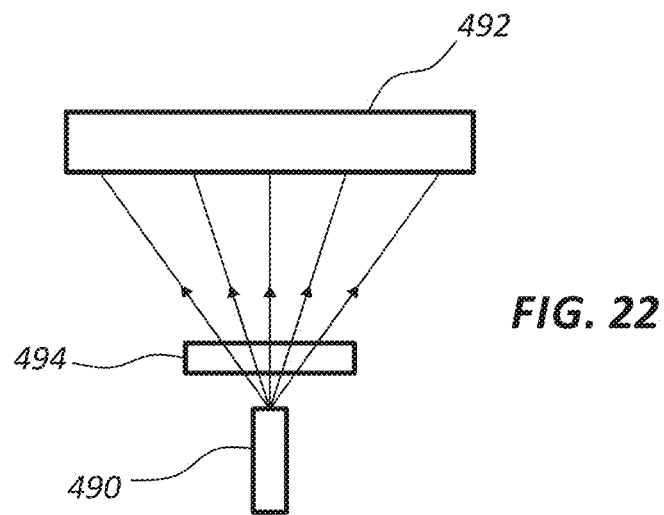
FIG. 22 shows elements of a cap detection system according to one embodiment.

FIGS. 20-22 depict yet other cap detection systems according to other embodiments. In detail, FIG. 20 shows a cap detection system including light source/detector 470 capable of emitting and detecting light or other suitable form of electromagnetic radiation, and a retro reflector 472 configured to reflect light back in the direction of the light impinging upon it. The light source/detector 470 and retro reflector 472 can be respectively placed on the probe and cap in an offset configuration as shown in FIG. 20 to enable cap detection to occur only when both components are suitably positioned with respect to one another. If the light is not reflected back, then the cap is considered not attached.

FIG. 21 shows a cap detection system including light source/detector 480 capable of emitting and detecting light or other suitable form of electromagnetic radiation, and a phosphorous-coated element 482 that is configured to emit light at a particular wavelength and in a predetermined timeframe after the impingement of light from the light source/detector. In operation, light is emitted from the light source/detector 480 and impinges on phosphorous-coated element 482, both components being respectively positioned on the probe and the cap in a suitable configuration. The impinging light causes the phosphorous-coated element 482 to re-emit light of a particular wavelength, which can be detected by the light source/detector 480. Additionally, the re-emitted light can emit from the phosphorous-coated element 482 at a decay rate that can be detected by the light source/detector 480 and analyzed by the system 10 to determine that the cap is suitably attached. If the light re-emission and/or decay rate are not detected, then the cap is considered not attached.

FIG. 22 shows a cap detection system including light source/detector 490 capable of emitting and detecting light or other suitable form of electromagnetic radiation, and a polarizing reflector 492 configured to reflect back polarized light to the light source/detector. A polarizing filter 494 is interposed between the light source/detector 490 and the polarizing reflector 492 and can prevent transmission of light that has a polarization of 90 degrees from that of the filter. By properly orienting the reflector 492 and filter 494 with respect to each other as respectively attached to the probe and cap (or via versa), the system 10 can determine whether the cap is suitably attached to the probe by analyzing the characteristics of the light detected by the light source/detector 490 after reflection by the reflector and passage through the filter. Note that in this and the other embodiments above, the light source/detector can be separate components, in one embodiment. Note also that the embodiments discussed above, including the discussion relating to FIGS. 20-22, can be useful for eliminating false positive detections of cap attachment and for preventing use of non-authorized components with the probe, in one embodiment.

In addition to the foregoing, other cap detection systems can be employed, including manual input to the imaging system 10 by a user after visually determining that the cap or other component is suitably attached to the probe, in one embodiment.

Embodiments described herein may comprise a special purpose or general-purpose computer including computer hardware, as discussed in greater detail below. Embodiments within the scope of the present disclosure also include computer-readable media for carrying or having computer-executable instructions or data structures stored thereon. Such computer-readable media can be any available media that can be accessed by a general purpose or special purpose computer. By way of example, and not limitation, computer-readable media can comprise physical (or recordable-type) computer-readable storage media, such as, RAM, ROM, EEPROM, CD-ROM or other optical disk storage, magnetic disk storage or other magnetic storage devices, or any other medium which can be used to store desired program code means in the form of computer-executable instructions or data structures and which can be accessed by a general purpose or special purpose computer.

A "network" is defined herein as one or more data links that enable the transport of electronic data between computer systems and/or modules. When information is transferred or provided over a network or another communications connection (either hardwired, wireless, or a combination of hardwired or wireless) to a computer, the computer properly views the connection as a computer-readable medium. Thus, by way of example, and not limitation, computer-readable media can also comprise a network or data links which can be used to carry or store desired program code means in the form of computer-executable instructions or data structures and which can be accessed by a general purpose or special purpose computer.

Computer-executable instructions comprise, for example, instructions and data which cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the embodiments herein may be practiced in network computing environments with many types of computer system configurations, including, personal computers, desktop computers, laptop computers, message processors, hand-held or portable devices, multi-processor systems, microprocessor-based or programmable consumer electronics, network PCs, minicomputers, mainframe computers, mobile telephones and devices, PDAs, pagers, and the like. The embodiments may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. An ultrasound imaging system, comprising:
an ultrasound probe, including a head portion;
a cap removably attachable to the ultrasound probe, wherein the cap at least partially covers the head portion, and wherein the cap includes a spacer component interposed between the head portion and skin of a patient during use of the ultrasound probe; and
a cap attachment detection system for detecting attachment of the cap to the ultrasound probe, including:
one or more processors; and
a non-transitory computer-readable storage medium having stored thereon instructions, that when executed by the one or more processors, cause performance of operations including:
responsive to detection of attachment of the cap to the ultrasound probe, modifying an ultrasound image produced by the ultrasound imaging system including removal of a portion of the ultrasound image corresponding to any imaged spacer component of the cap to the ultrasound probe, wherein the cap attachment detection system:
uses the one or more processors to detect image intensity levels of a plurality of sampling zones of the ultrasound image produced by the ultrasound imaging system, the plurality of sampling zones disposed in a region of the ultrasound image where the spacer component is expected to be located, and
determines the cap is attached to the ultrasound probe when a minimum number of sampling zones include image intensity levels below a particular threshold level.

2. The system as defined in claim 1, wherein the spacer component of the cap includes a hydrogel insert.

3. The system as defined in claim 2, wherein the cap attachment detection system includes at least one reflective marker disposed in the hydrogel insert, the at least one reflective marker detectable by at least one transducer element of a transducer array of the ultrasound probe.

4. The system as defined in claim 2, wherein the cap attachment detection system includes at least two transducer elements of a transducer array disposed in the head portion of the ultrasound probe, the at least two transducer elements used by the cap attachment detection system to a detect a transition from an acoustically transparent region to an acoustically non-transparent region in a region of interest.

5. The system as defined in claim 2, wherein the cap attachment detection system includes a magnetic sensor included with the ultrasound probe that detects a magnetic element included with the cap when the cap is attached to the ultrasound probe.

6. The system as defined in claim 2, wherein the cap attachment detection system includes an infrared transceiver included with the ultrasound probe that detects the cap via infrared reflection when the cap is attached to the ultrasound probe.

7. The system as defined in claim 2, wherein the cap attachment detection system includes a mechanical switch included on the ultrasound probe, the mechanical switch actuated when the cap is attached to the ultrasound probe.

8. The system as defined in claim 2, wherein the cap attachment detection system includes a RFID reader included with the ultrasound probe that detects an RFID chip included with the cap when the cap is attached to the ultrasound probe.

9. The system as defined in claim 1, wherein the cap attachment detection system includes a light source, a light detector, and at least one of a retro reflector, a phosphorus element, and a polarizing reflector.

10. A method for using an ultrasound imaging system, the ultrasound imaging system including an ultrasound probe having a head portion, a display for depicting ultrasound images produced by the ultrasound probe, and a cap that is attachable to the ultrasound probe and including a spacer component interposed between the head portion and skin of a patient during use of the ultrasound probe, the method comprising:
by a cap attachment detection system of the ultrasound imaging system, detecting whether the cap is attached to the ultrasound probe; and
responsive to detecting the cap as attached to the ultrasound probe, altering an ultrasound image produced by the ultrasound imaging system including removal of a portion of the ultrasound image corresponding to any imaged spacer component of the cap of the ultrasound probe, wherein altering the ultrasound image includes changing an orientation of the ultrasound image from a first image orientation to a second image orientation.

11. The method as defined in claim 10, further comprising cropping a first portion of the ultrasound image and adjusting a grayscale or other image characteristic of the ultrasound image when the ultrasound image is oriented in the second image orientation.

12. The method as defined in claim 10, wherein the spacer component includes a hydrogel-based spacer portion.

13. The method as defined in claim 10, wherein the cap attaches to the ultrasound probe so as to cover the head portion of the ultrasound probe, and wherein the method further comprises:
when the cap is not attached to the ultrasound probe, a message is conveyed to a user of the ultrasound imaging system.

14. The method as defined in claim 13, wherein the message includes a popup window depicted on the display.

15. The method as defined in claim 10, wherein the method is implemented by a processor executing computer executable instructions, and wherein uninhibited use of the ultrasound imaging system is enabled after the cap is detected as being attached to the ultrasound probe.

16. The method as defined in claim 10, wherein the method is implemented by a processor executing a Hough transform algorithm.

17. The method as defined in claim 10, wherein the cap attachment detection system includes a light source, a light detector, and at least one of a retro reflector, a phosphorus element, and a polarizing reflector.

18. An ultrasound imaging system, comprising:
an ultrasound probe, including a head portion;
a cap removably attachable to the ultrasound probe, wherein the cap at least partially covers the head portion, and wherein the cap includes a spacer component interposed between the head portion and skin of a patient during use of the ultrasound probe, the spacer component including a hydrogel insert; and
a cap attachment detection system for detecting attachment of the cap to the ultrasound probe, including:
a magnetic sensor included with the ultrasound probe that detects a magnetic element included with the cap when the cap is attached to the ultrasound probe;
one or more processors; and
a non-transitory computer-readable storage medium having stored thereon instructions, that when executed by the one or more processors, cause performance of operations including:
responsive to detection of attachment of the cap to the ultrasound probe, modifying an ultrasound image produced by the ultrasound imaging system including removal of a portion of the ultrasound image corresponding to any imaged spacer component of the cap to the ultrasound probe.

19. An ultrasound imaging system, comprising:
an ultrasound probe, including a head portion;
a cap removably attachable to the ultrasound probe, wherein the cap at least partially covers the head portion, and wherein the cap includes a spacer component interposed between the head portion and skin of a patient during use of the ultrasound probe, the spacer component including a hydrogel insert; and
a cap attachment detection system for detecting attachment of the cap to the ultrasound probe, including:
an infrared transceiver included with the ultrasound probe that detects the cap via infrared reflection when the cap is attached to the ultrasound probe;
one or more processors; and
a non-transitory computer-readable storage medium having stored thereon instructions, that when executed by the one or more processors, cause performance of operations including:
responsive to detection of attachment of the cap to the ultrasound probe, modifying an ultrasound image produced by the ultrasound imaging system including removal of a portion of the ultrasound image corresponding to any imaged spacer component of the cap to the ultrasound probe.

20. An ultrasound imaging system, comprising:
an ultrasound probe, including a head portion;
a cap removably attachable to the ultrasound probe, wherein the cap at least partially covers the head portion, and wherein the cap includes a spacer component interposed between the head portion and skin of a patient during use of the ultrasound probe, the spacer component including a hydrogel insert; and
a cap attachment detection system for detecting attachment of the cap to the ultrasound probe, including:

a mechanical switch included on the ultrasound probe, the mechanical switch actuated when the cap is attached to the ultrasound probe;

one or more processors; and a non-transitory computer-readable storage medium having stored thereon instructions, that when executed by the one or more processors, cause performance of operations including:

responsive to detection of attachment of the cap to the ultrasound probe, modifying an ultrasound image produced by the ultrasound imaging system including removal of a portion of the ultrasound image corresponding to any imaged spacer component of the cap to the ultrasound probe.

* * * * *